United States Patent
Jenkins et al.

(10) Patent No.: US 8,962,547 B2
(45) Date of Patent: *Feb. 24, 2015

(54) COMPOSITIONS COMPRISING ENZYME-CLEAVABLE OXYCODONE PRODRUG

(71) Applicant: Signature Therapeutics, Inc., Palo Alto, CA (US)

(72) Inventors: Thomas E. Jenkins, Half Moon Bay, CA (US); Craig O. Husfeld, San Mateo, CA (US)

(73) Assignee: Signature Therapeutics, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/035,871

(22) Filed: Sep. 24, 2013

(65) Prior Publication Data

US 2014/0162935 A1    Jun. 12, 2014

Related U.S. Application Data

(63) Continuation of application No. 13/346,062, filed on Jan. 9, 2012, now Pat. No. 8,569,228.

(60) Provisional application No. 61/431,781, filed on Jan. 11, 2011.

(51) Int. Cl.
| | | |
|---|---|---|
| *A61K 38/00* | (2006.01) | |
| *A61K 47/48* | (2006.01) | |
| *A61K 31/485* | (2006.01) | |
| *A61K 45/06* | (2006.01) | |
| *C07D 489/08* | (2006.01) | |
| *C12Q 1/37* | (2006.01) | |
| *A61K 31/155* | (2006.01) | |
| *A61K 31/195* | (2006.01) | |
| *A61K 31/245* | (2006.01) | |
| *A61K 31/445* | (2006.01) | |
| *A61K 31/4965* | (2006.01) | |
| *A61K 38/05* | (2006.01) | |

(52) U.S. Cl.
CPC ......... *A61K 47/48246* (2013.01); *A61K 31/485* (2013.01); *A61K 45/06* (2013.01); *C07D 489/08* (2013.01); *C12Q 1/37* (2013.01); *A61K 31/155* (2013.01); *A61K 31/195* (2013.01); *A61K 31/245* (2013.01); *A61K 31/445* (2013.01); *A61K 31/4965* (2013.01); *A61K 38/05* (2013.01)
USPC .......................................................... 514/1.1

(58) Field of Classification Search
CPC . A61K 45/06; A61K 31/485; A61K 39/3955; A61K 38/00
See application file for complete search history.

(56) References Cited

U.S. PATENT DOCUMENTS

| | | |
|---|---|---|
| 4,454,338 A | 6/1984 | Fujii et al. |
| 4,532,255 A | 7/1985 | Fujii et al. |
| 5,352,704 A | 10/1994 | Okuyama et al. |
| 6,388,122 B1 | 5/2002 | Kido et al. |
| 6,586,196 B1 | 7/2003 | Bronstein et al. |
| 7,060,290 B1 | 6/2006 | Morimoto et al. |
| 7,189,414 B2 | 3/2007 | Rubinstein et al. |
| 7,893,105 B2 | 2/2011 | Xiang et al. |
| 8,569,228 B2 | 10/2013 | Jenkins et al. |
| 2003/0180352 A1 | 9/2003 | Patel et al. |
| 2004/0063628 A1 | 4/2004 | Piccariello et al. |
| 2005/0176644 A1 | 8/2005 | Mickle et al. |
| 2007/0082929 A1 | 4/2007 | Gant et al. |
| 2007/0123468 A1 | 5/2007 | Jenkins et al. |
| 2007/0203055 A1 | 8/2007 | Mickle et al. |
| 2009/0136980 A1 | 5/2009 | Bebbington et al. |
| 2009/0137618 A1 | 5/2009 | Jenkins et al. |
| 2009/0192093 A1 | 7/2009 | Mickle et al. |
| 2009/0209569 A1 | 8/2009 | Arnelle et al. |
| 2010/0035826 A1 | 2/2010 | Jenkins et al. |
| 2010/0080797 A1 | 4/2010 | Yeomans et al. |
| 2010/0092562 A1 | 4/2010 | Hollenbeck et al. |
| 2010/0286186 A1 | 11/2010 | Franklin et al. |

FOREIGN PATENT DOCUMENTS

| | | |
|---|---|---|
| WO | 2007140272 | 12/2007 |
| WO | 2008101187 | 8/2008 |
| WO | 2008101202 | 8/2008 |
| WO | 2010045599 | 4/2010 |

(Continued)

OTHER PUBLICATIONS

Berkop-Schnurch "The use of inhibitory agents to overcome the enzymatic barrier to perorally administered therapeutic peptides and proteins" J. Control. Release (1998), vol. 50, No. 1-2, pp. 1-16.

(Continued)

*Primary Examiner* — Marcela M Cordero Garcia
*Assistant Examiner* — Kaipeen Yang
(74) *Attorney, Agent, or Firm* — Carol L. Francis; Bozicevic, Field & Francis LLP

(57) ABSTRACT

The embodiments provide Compound KC-8, N-1-[3-(oxycodone-6-enol-carbonyl-methyl-amino)-2,2-dimethyl-propylamine]-arginine-glycine-malonic acid, or acceptable salts, solvates, and hydrates thereof. The present disclosure also provides compositions, and their methods of use, where the compositions comprise a prodrug, Compound KC-8, that provides controlled release of oxycodone. Such compositions can optionally provide a trypsin inhibitor that interacts with the enzyme that mediates the controlled release of oxycodone from the prodrug so as to attenuate enzymatic cleavage of the prodrug.

12 Claims, 9 Drawing Sheets

(56) References Cited

FOREIGN PATENT DOCUMENTS

| WO | WO 2011031350 A1 * | 3/2011 |
| WO | 2011133346 | 4/2011 |

OTHER PUBLICATIONS

Birk et al., "Trypsin and chymotrypsin inhibitors from soybeans" Methods in Enzymology (1976) vol. 45, pp. 700-707.

Geratz et al., "Novel bis(benzamidine) compounds with an aromatic central link. Inhibitors of thrombin, pancreatic kallikrein, trypsin, and complement" J. Med. Chem. (1976), vol. 19, pp. 634-639.

Göke et al., "Effect of a Specific Serine Protease Inhibitor on the Rat Pancreas: Systemic Administration of Camostate and Exocrine" Digestion (1984) vol. 30, pp. 171-178.

Gomes et al., "Cyclization-activated prodrugs" Molecules, (2007), vol. 12, pp. 2484-2506.

Hijikata et al., "Selective Inhibition of Trypsin by (2R,4R)-4-Phenyl-1-[Nα-(7-methoxy-2-naphthalenesulfonyl)-L-arginyl]-2-piperidinecarboxylic Acid" J. Biochem. (2000), vol. 275, pp. 18995-18999.

Kunze et al., "Effects of the serine protease inhibitors FOY and FOY 305 on phospholipase A I (EC 3.1.1.32) activity in rat-liver lysosomes" Pharm. Research Com. (1983), vol. 15, pp. 451-459.

Lin et al., "The 0.25-nm X-ray structure of the Bowman-Birk type inhibitor from mung bean in ternary complex with porcine trypsin" Eur. J. Biochem., (1993), vol. 212, pp. 549-555.

Markwardt et al., "Comparative studies on the inhibition of trypsin, plasmin, and thrombin by derivatives of benzylamine and benzylamidine" Eur. J. Biochem, (1968), vol. 6, pp. 502-506.

Ozawa et al., "The reactive site of trypsin inhibitors" J. Biol. Chem. (1966), vol. 241, pp. 3955-3961.

Ramjee et al. "The Kinetic and Structural Characterization of the Reaction of Nafamostat with Bovine Pancreatic Trypsin" Thrmb Res. (2000), vol. 98, No. 6, pp. 559-569.

Renatus et al. "Structural and Functional Analyses of Benzamidine-Based Inhibitors in Complex with Trypsin: Implications for the Inhibition of Factor Xa, tPA, and Urokinase" j. Med. Chem., (1998), vol. 41, No. 27 pp. 5445-5456.

Tanizawa et al. "Inverse Substrates for Tryspin and Tryspin-like Enzymes" Acc. Chem. Res., (1987), vol. 20, pp. 337-343.

Testa et al, "Hydrolysis in Drug and Prodrug Metabolism" Verlag Helvetica Chimica Acta, Postfach, CH-8042, Switzerland (2003) pp. 420-534.

Tirkkonen et al., "Drug interactions with the potential to prevent prodrug activation as a common source of irrational prescribing in hospital inpatients" Clinical Pharmacology and Therapeutics, (2004) vol. 76, No. 6, pp. 639-647.

Umezawa et al., "Structure and activities of protease inhibitors of microbial origin" Methods in Enzymology (1976) vol. 45, pp. 678-695.

* cited by examiner

COMPOSITIONS COMPRISING ENZYME-CLEAVABLE OXYCODONE PRODRUG

CROSS REFERENCE TO RELATED APPLICATIONS

This application is a continuation of U.S. patent application Ser. No. 13/346,062, filed Jan. 9, 2012, now U.S. Pat. No. 8,569,228 which claims the benefit of U.S. Provisional Application No. 61/431,781 filed Jan. 11, 2011.

Ketone-containing opioids, such as hydrocodone and oxycodone, are susceptible to misuse, abuse, or overdose. Use of and access to these drugs therefore needs to be controlled. The control of access to the drugs is expensive to administer and can result in denial of treatment for patients that are not able to present themselves for dosing. For example, patients suffering from acute pain may be denied treatment with an opioid unless they have been admitted to a hospital. Furthermore, control of use is often ineffective, leading to substantial morbidity and deleterious social consequences.

SUMMARY

The embodiments provide Compound KC-8, N-1-[3-(oxycodone-6-enol-carbonyl-methyl-amino)-2,2-dimethyl-propylamine]-arginine-glycine-malonic acid, shown below:

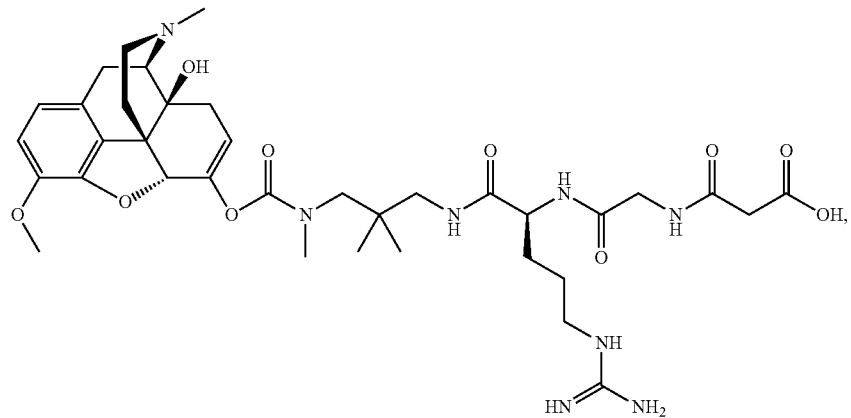

(KC-8)

or acceptable salts, solvates, and hydrates thereof. Compound KC-8 is a prodrug that provides controlled release of oxycodone.

The embodiments provide a composition, which comprises N-1-[3-(oxycodone-6-enol-carbonyl-methyl-amino)-2,2-dimethyl-propylamine]-arginine-glycine-malonic acid, Compound KC-8, shown below:

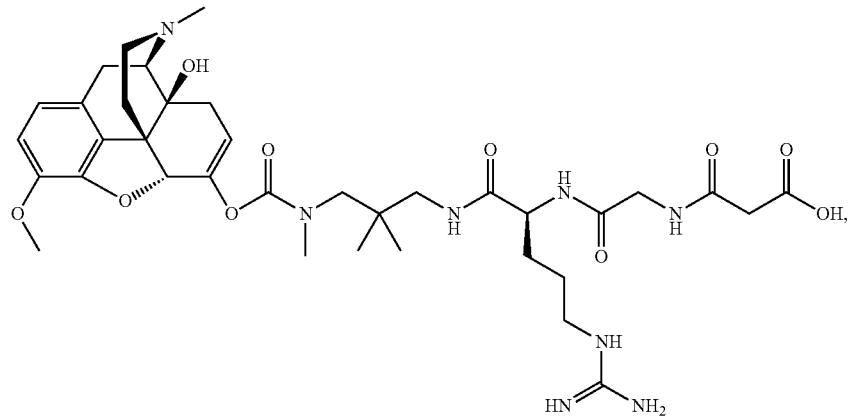

(KC-8)

or pharmaceutically acceptable salts, solvates, and hydrates thereof.

The disclosure provides Compound KC-8, a ketone-modified opioid prodrug that provides controlled release of oxycodone. In a ketone-modified opioid prodrug, a promoiety is attached to oxycodone through the enolic oxygen atom of oxycodone. In a ketone-modified opioid prodrug, the hydrogen atom of the corresponding enolic group of oxycodone is replaced by a covalent bond to a promoiety. The promoiety comprises an enzyme-cleavable moiety and a cyclizable spacer leaving group such that Compound KC-8 provides controlled release of oxycodone via enzyme cleavage followed by intramolecular cyclization. Compound KC-8 provides efficient delivery of oxycodone when ingested.

The present disclosure also provides pharmaceutical compositions, and their methods of use, where the pharmaceutical compositions comprise a prodrug, Compound KC-8, that provides controlled release of oxycodone via enzyme cleavage followed by intramolecular cyclization. Such compositions can optionally provide an inhibitor, such as a trypsin inhibitor, that interacts with the enzyme that mediates the controlled release of oxycodone from the prodrug so as to attenuate enzymatic cleavage of the prodrug. The disclosure provides for the enzyme being a gastrointestinal (GI) enzyme, such as trypsin.

TERMS

Figure 1:
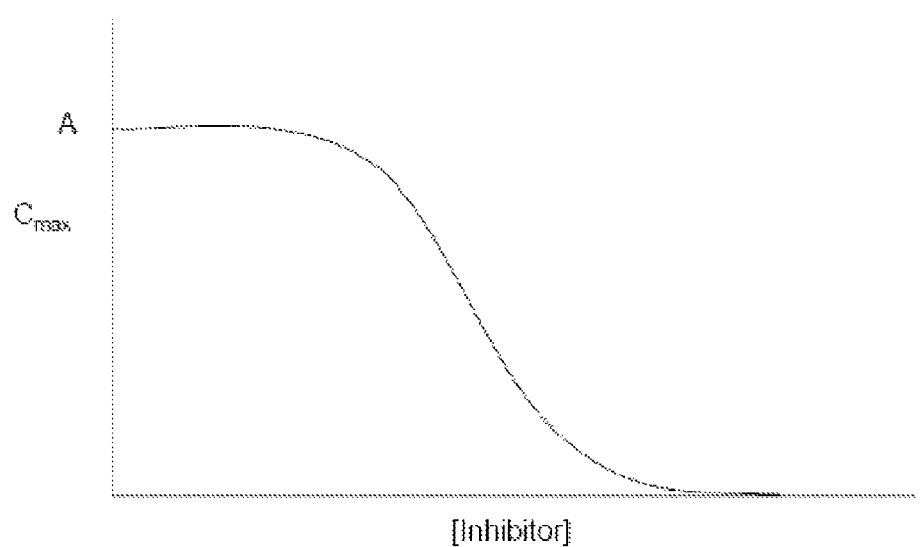
FIG. 1 is a schematic representing the effect of increasing the level of a trypsin inhibitor ("inhibitor", X axis) on a PK parameter (e.g., drug Cmax) (Y axis) for a fixed dose of prodrug. The effect of inhibitor upon a prodrug PK parameter can range from undetectable, to moderate, to complete inhibition (i.e., no detectable drug release).

The following terms have the following meaning unless otherwise indicated. Any undefined terms have their art recognized meanings.

"Dose unit" as used herein refers to a combination of a trypsin-cleavable prodrug (e.g., trypsin-cleavable prodrug) and a trypsin inhibitor. A "single dose unit" is a single unit of a combination of a trypsin-cleavable prodrug (e.g., trypsin-cleavable prodrug) and a trypsin inhibitor, where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

"Gastrointestinal enzyme" or "GI enzyme" refers to an enzyme located in the gastrointestinal (GI) tract, which encompasses the anatomical sites from mouth to anus. Trypsin is an example of a GI enzyme.

"Gastrointestinal enzyme-cleavable moiety" or "GI enzyme-cleavable moiety" refers to a group comprising a site susceptible to cleavage by a GI enzyme. For example, a "trypsin-cleavable moiety" refers to a group comprising a site susceptible to cleavage by trypsin.

"Gastrointestinal enzyme inhibitor" or "GI enzyme inhibitor" refers to any agent capable of inhibiting the action of a gastrointestinal enzyme on a substrate. The term also encompasses salts of gastrointestinal enzyme inhibitors. For example, a "trypsin inhibitor" refers to any agent capable of inhibiting the action of trypsin on a substrate.

"Patient" includes humans, and also other mammals, such as livestock, zoo animals and companion animals, such as a cat, dog or horse.

"Pharmaceutical composition" refers to at least one compound and can further comprise a pharmaceutically acceptable carrier, with which the compound is administered to a patient.

"Pharmaceutically acceptable carrier" refers to a diluent, adjuvant, excipient or vehicle with, or in which a compound is administered.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethane-sulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"PK parameter" refers to a measure of drug concentration in blood or plasma, such as: 1) "drug Cmax", the maximum concentration of drug achieved in blood or plasma; 2) "drug $T_{max}$", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. In certain embodiments, the transformation is a cyclization transformation. In certain embodiments, the transformation is a combination of an enzymatic transformation and a cyclization reaction. Prodrugs are frequently, although not necessarily, pharmacologically inactive until converted to the active agent.

"Promoiety" refers to a form of protecting group that, when used to mask a functional group within an active agent, converts the active agent into a prodrug. Typically, the promoiety will be attached to the drug via bond(s) that are cleaved by enzymatic or non-enzymatic means in vivo.

"Solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Therapeutically effective amount" means the amount of a compound (e.g., prodrug) that, when administered to a patient for preventing or treating a condition such as pain, is sufficient to effect such treatment. The "therapeutically effective amount" will vary depending on the compound, the condition and its severity and the age, weight, etc., of the patient.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a compound refers to one or more compounds. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. In certain instances, this nomenclature is derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds.

The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Representative Embodiments

Reference will now be made in detail to various embodiments. It will be understood that the invention is not limited to these embodiments. To the contrary, it is intended to cover alternatives, modifications, and equivalents as may be included within the spirit and scope of the allowed claims.

The embodiments provide Compound KC-8, N-1-[3-(oxycodone-6-enol-carbonyl-methyl-amino)-2,2-dimethyl-propylamine]-arginine-glycine-malonic acid, shown below:

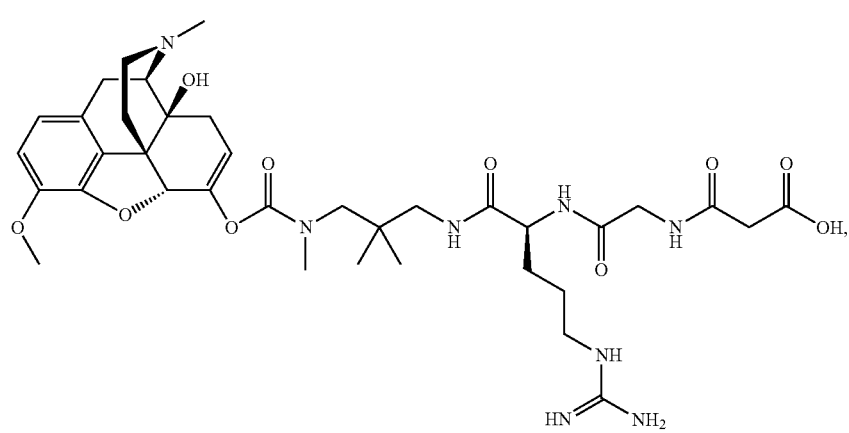

(KC-8)

or acceptable salts, solvates, and hydrates thereof.

The embodiments provide a composition, which comprises N-1-[3-(oxycodone-6-enol-carbonyl-methyl-amino)-2,2-dimethyl-propylamine]-arginine-glycine-malonic acid, Compound KC-8, shown below:

(KC-8)

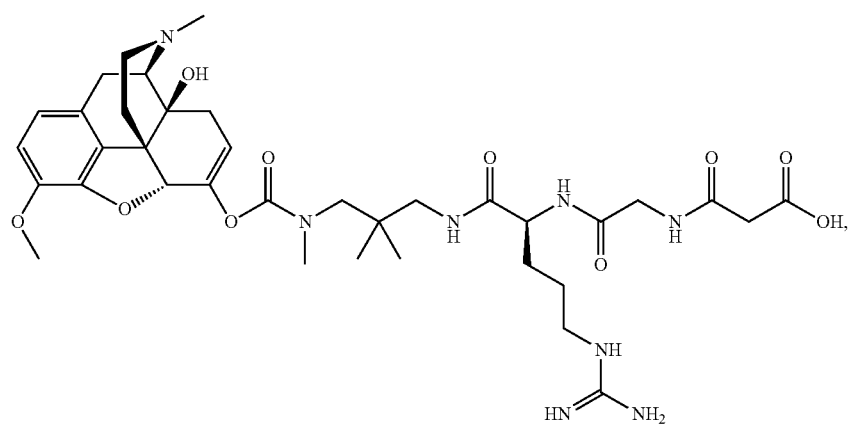

or pharmaceutically acceptable salts, solvates, and hydrates thereof.

The disclosure provides Compound KC-8, a ketone-modified opioid prodrug that provides controlled release of oxycodone. In a ketone-modified opioid prodrug, a promoiety is attached to oxycodone through the enolic oxygen atom of oxycodone. In a ketone-modified opioid prodrug, the hydrogen atom of the corresponding enolic group of oxycodone is replaced by a covalent bond to a promoiety.

In Compound KC-8, the promoiety comprises a cyclizable spacer leaving group and a cleavable moiety. In Compound KC-8, the ketone-modified oxycodone prodrug is a corresponding compound in which the enolic oxygen atom has been substituted with a spacer leaving group bearing a nitrogen nucleophile that is protected with an enzyme-cleavable moiety, the configuration of the spacer leaving group and nitrogen nucleophile being such that, upon enzymatic cleavage of the cleavable moiety, the nitrogen nucleophile is capable of forming a cyclic urea, liberating the compound from the spacer leaving group so as to provide oxycodone.

The enzyme capable of cleaving the enzyme-cleavable moiety may be a peptidase, also referred to as a protease—the promoiety comprising the enzyme-cleavable moiety being linked to the nucleophilic nitrogen through an amide (e.g. a peptide: —NHC(O)—) bond. In some embodiments, the enzyme is a digestive enzyme of a protein. The disclosure provides for the enzyme being a GI enzyme, such as trypsin and for the enzyme-cleavable moiety being a GI enzyme-cleavable moiety, such as a trypsin-cleavable moiety.

The corresponding prodrug provides post administration-activated, controlled release of oxycodone. The prodrug requires enzymatic cleavage to initiate release of oxycodone, and thus the rate of release of oxycodone depends upon both the rate of enzymatic cleavage and the rate of cyclization. Compound KC-8 provides efficient controlled release of oxycodone due to a combination of a rapid enzyme cleavage rate and a rapid intramolecular cyclization rate. The prodrug is configured so that it will not provide excessively high plasma levels of the active drug if it is administered inappropriately, and cannot readily be decomposed to afford the active drug other than by enzymatic cleavage followed by controlled cyclization.

The cyclic group formed when oxycodone is released is conveniently pharmaceutically acceptable, in particular a pharmaceutically acceptable cyclic urea. It will be appreciated that cyclic ureas are generally very stable and have low toxicity.

General Synthetic Procedures for Compounds

Representative synthetic schemes for compounds disclosed herein are shown below. Compound KC-8 can be synthesized by using the disclosed methods.

Representative Synthetic Schemes

A representative synthesis for Compound S-104 is shown in Scheme 1. In Scheme 1, for Compound KC-8, n is 3; the first and third geminal $R^1$ and $R^2$ are hydrogen; the second geminal $R^1$ and $R^2$ are methyl; $R^5$ is methyl; and $PG^1$ is an amino protecting group.

Scheme 1

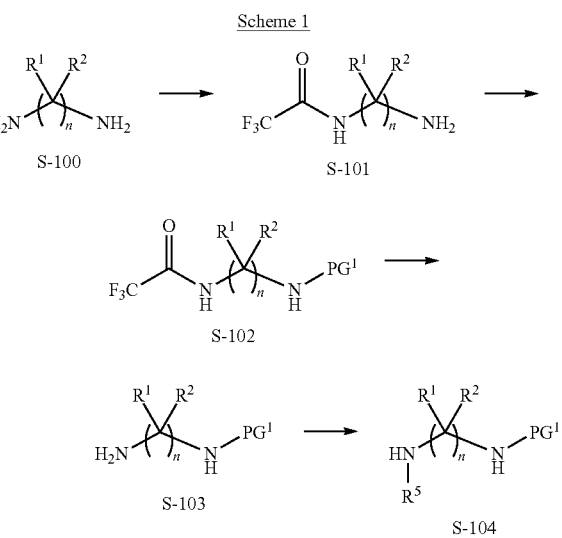

In Scheme 1, Compound S-100 is a commercially available starting material. Alternatively, Compound S-100 can be synthesized via a variety of different synthetic routes using commercially available starting materials and/or starting materials prepared by conventional synthetic methods.

With continued reference to Scheme 1, Compound S-100 is protected at the amino group with a trifluoroacetyl group to form Compound S-101. A trifluoroacetyl group can be formed with reaction using reagents, such as ethyl trifluoroacetate, trifluoroacetyl chloride, or 1,1,1-trichloro-3,3,3-trifluoroacetone.

Compound S-101 is protected at the other amino group to form Compound S-102, wherein $PG^1$ is an amino protecting group. Amino protecting groups can be found in T. W Greene and P. G. M. Wuts, "*Protective Groups in Organic Synthesis*", Fourth edition, Wiley, New York 2006. Representative amino-protecting groups include, but are not limited to, formyl groups; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

In certain embodiments, $PG^1$ is Boc. Conditions for forming Boc groups on Compound S-102 can be found in Greene and Wuts. One method is reaction of Compound S-101 with di-tert-butyl dicarbonate. The reaction can optionally be run in the presence of an activating agent, such as DMAP. In Scheme 1, in certain embodiments, the trifluoroacetyl protecting group and $PG^1$, such as Boc, are orthogonal protecting groups.

With continued reference to Scheme 1, the trifluoroacetyl group on Compound S-102 is deprotected to form Compound S-103. Conditions to remove the trifluoroacetyl group can be found in Greene and Wuts. Methods to remove the trifluoroacetyl group include hydrolysis of Compound S-102. Certain conditions for hydrolysis include reaction with sodium hydroxide or lithium hydroxide.

With continued reference to Scheme 1, the $R^5$ group is added onto Compound S-103 to form Compound S-104. The addition of the $R^5$ group onto the amino group of Compound S-103 can be facilitated with the use of protecting/activating groups. In certain embodiments, a nosyl group is added onto the amino group of Compound S-103 before addition of the $R^5$ group. A nosyl group can be added with use of nosyl chloride.

In certain embodiments, the $R^5$ group is methyl and is added through use of methyl iodide. After addition of the $R^5$ group, the protecting/activating group can be removed to yield Compound S-104. For example, removal of the nosyl group can be performed with thiophenol.

A representative synthesis for Compound S-202 is shown in Scheme 2. In Scheme 2, for Compound KC-8, $R^a$ is hydroxyl; n is 3; the first and third geminal $R^1$ and $R^2$ are hydrogen; the second geminal $R^1$ and $R^2$ are methyl; $R^5$ is methyl; and $PG^1$ is an amino protecting group.

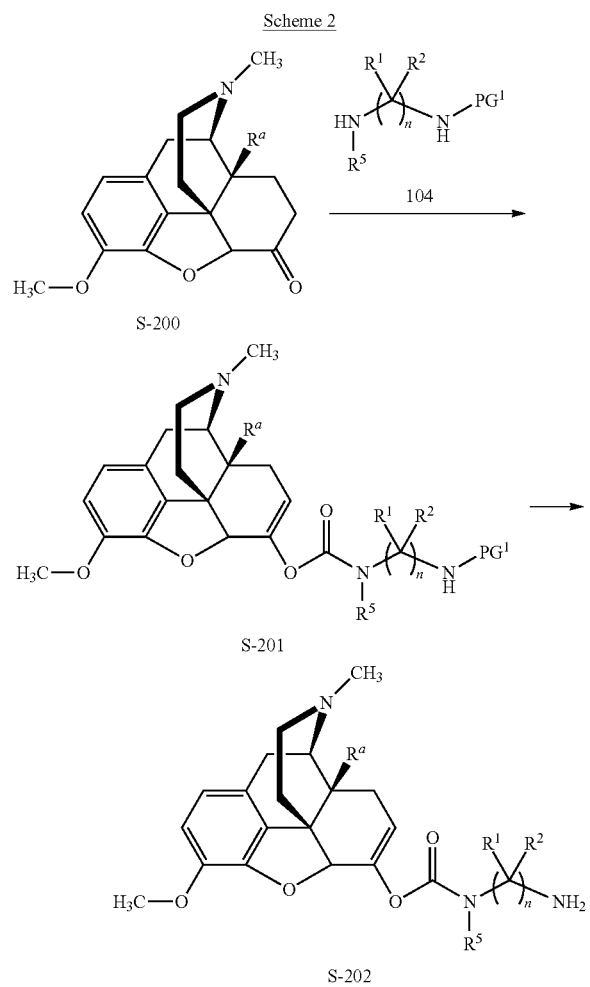

In Scheme 2, Compound S-200 is a commercially available starting material. Alternatively, Compound S-200 can be semi-synthetically derived from natural materials or synthesized via a variety of different synthetic routes using commercially available starting materials and/or starting materials prepared by conventional synthetic methods.

With continued reference to Scheme 2, Compound S-200 is reacted with Compound S-104 to form Compound S-201. In this reaction, Compound S-200 reacts with the amino group of Compound S-104 with a carbamate-forming reagent to yield Compound S-201. Suitable carbamate-forming reagents include chloroformates, such as 4-nitrophenyl chloroformate.

With continued reference to Scheme 2, the protecting group $PG^1$ is removed from Compound S-201 to form Compound S-202. Conditions to remove amino groups can be found in Greene and Wuts. When $PG^1$ is a Boc group, the protecting group can be removed with acidic conditions, such as treatment with hydrochloric acid or trifluoroacetic acid.

A representative synthesis for Compound S-303 is shown in Scheme 3. In Scheme 3, for Compound KC-8, $R^a$ is hydroxyl; n is 3; the first and third geminal $R^1$ and $R^2$ are hydrogen; the second geminal $R^1$ and $R^2$ are methyl; $R^5$ is methyl; $R^6$ is the side chain of arginine; and $PG^2$ is an optional amino protecting group.

Scheme 3

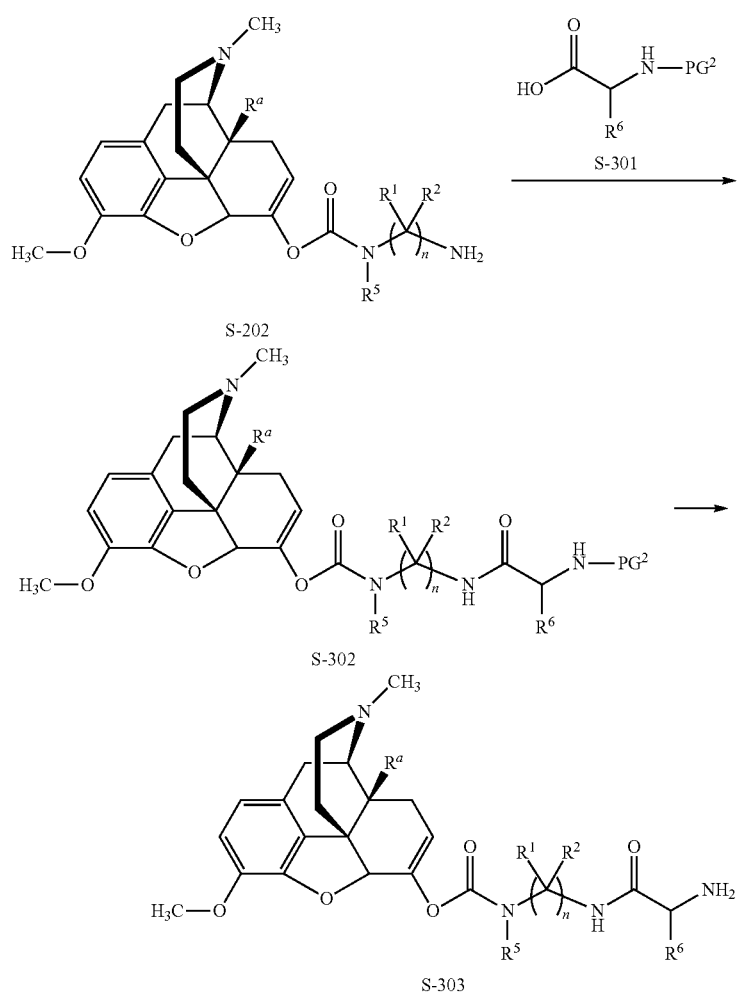

With reference to Scheme 3, Compound S-202 reacts with Compound S-301 to form Compound S-302 in a peptide coupling reaction. In certain embodiments, $R^6$ is the side chain of arginine and is optionally protected. Protecting groups for the side chain of arginine are known to those skilled in art and can be found in Greene and Wuts. In certain instances, the protecting group for the side chain of arginine is a sulfonyl-type protecting group, such as 2,2,4,6,7-pentamethyldihydrobenzofurane (Pbf). Other protecting groups include 2,2,5,7,8-pentamethylchroman (Pmc) and 1,2-dimethylindole-3-sulfonyl (MIS).

A peptide coupling reaction typically employs a conventional peptide coupling reagent and is conducted under conventional coupling reaction conditions, typically in the presence of a trialkylamine, such as ethyldiisopropylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris (dimethylamino)phosphonium hexafluorophosphate (BOP), O-(7-azabenzotriazol-1-yl)-N,N,N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound S-202 reacts with Compound S-301 to form Compound S-302 in the presence of HATU.

With continued reference to Scheme 3, Compound S-302 is transformed into Compound S-303 with removal of the amino protecting group. Conditions to remove amino groups can be found in Greene and Wuts. When $PG^2$ is a Boc group, the protecting group can be removed with acidic conditions, such as treatment with hydrochloric acid or trifluoroacetic acid.

A representative synthesis for Compound S-401 is shown in Scheme 4. In Scheme 4, for Compound KC-8, $R^a$ is hydroxyl; n is 3; the first and third geminal $R^1$ and $R^2$ are hydrogen; the second geminal $R^1$ and $R^2$ are methyl; $R^5$ is methyl; $R^6$ is the side chain of arginine; $R^7$ is the side chain of glycine; and $R^8$ is malonyl group.

Scheme 4

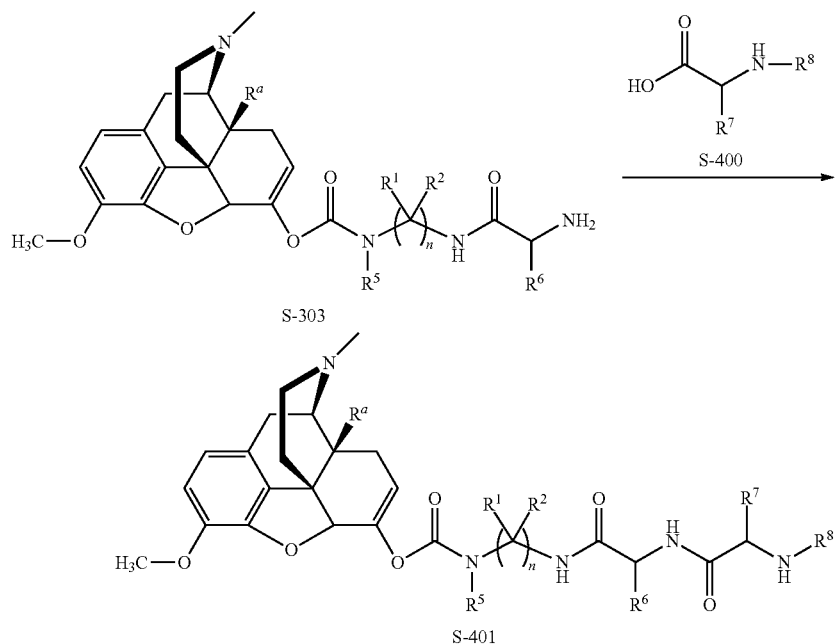

In Scheme 4, Compound S-400 is a commercially available starting material. Alternatively, Compound S-400 can be synthesized via a variety of different synthetic routes using commercially available starting materials and/or starting materials prepared by conventional synthetic methods.

With reference to Scheme 4, Compound S-303 reacts with Compound S-400 to form Compound S-401 in a peptide coupling reaction. A peptide coupling reaction typically employs a conventional peptide coupling reagent and is conducted under conventional coupling reaction conditions, typically in the presence of a trialkylamine, such as ethyldiisopropylamine or diisopropylethylamine (DIEA). Suitable coupling reagents for use include, by way of example, carbodiimides, such as ethyl-3-(3-dimethylamino)propylcarbodiimide (EDC), dicyclohexylcarbodiimide (DCC), diisopropylcarbodiimide (DIC) and the like, and other well-known coupling reagents, such as N,N'-carbonyldiimidazole, 2-ethoxy-1-ethoxycarbonyl-1,2-dihydroquinoline (EEDQ), benzotriazol-1-yloxy-tris(dimethylamino)phosphonium hexafluorophosphate (BOP), 0-(7-azabenzotriazol-1-yl)-N,N,N',N'-tetramethyluronium hexafluorophosphate (HATU) and the like. Optionally, well-known coupling promoters, such N-hydroxysuccinimide, 1-hydroxybenzotriazole (HOBT), 1-hydroxy-7-azabenzotriazole (HOAT), N,N-dimethylaminopyridine (DMAP) and the like, can be employed in this reaction. Typically, this coupling reaction is conducted at a temperature ranging from about 0° C. to about 60° C. for about 1 to about 72 hours in an inert diluent, such as THF or DMF. In certain instances, Compound S-303 reacts with Compound S-400 to form Compound S-401 in the presence of HATU.

In certain instances in Scheme 4, when Compound S-400 is reacted with Compound S-303 with $R^8$ as hydrogen, the $R^8$ group as a malonyl group is added after the amino acid coupling reaction. A malonyl group can be attached via a reaction with mono-tert-butyl malonate. Reaction using mono-tert-butyl malonate can be aided with use of activation reagents, such as symmetric anhydrides, O-(benzotriazol-1-yl)-N,N,N',N'-tetramethyluronium hexafluorophosphate (HBTU), dicyclohexylcarbodiimide (DCC) diisopropylcarbodiimide (DIC)/1-hydroxybenzotriazole (HOBt), and benzotriazole-1-yl-oxytris(dimethylamino)phosphonium hexafluorophosphate (BOP). A malonyl group can also be attached using N-carboxymethylmalonic acid tert-butyl ester.

With continued reference to Scheme 4, removal of other protecting groups can be performed if other protecting groups were used, such as protecting groups present on the $R^6$ moiety. Conditions for removal of other protecting groups depend on the identity of the protecting group and are known to those skilled in the art. The conditions can also be found in Greene and Wuts.

Further Representative Synthetic Schemes

A representative synthesis for Compound S-503 is shown in Scheme 5. In Scheme 5, for Compound KC-8, n is 3; the first and third geminal $R^1$ and $R^2$ are hydrogen; the second geminal $R^1$ and $R^2$ are methyl; $R^5$ is methyl; and $PG^1$ and $PG^2$ are optional amino protecting groups.

Scheme 5

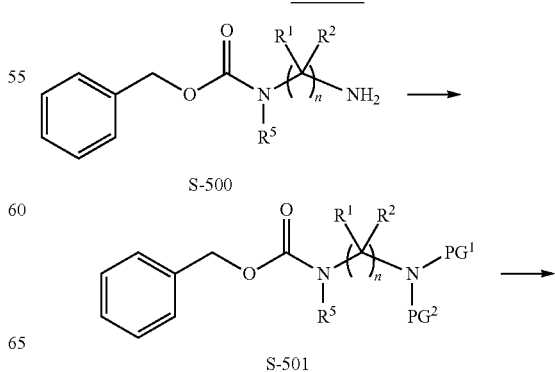

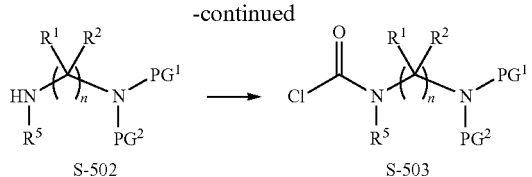

In Scheme 5, Compound S-500 is a commercially available starting material. Alternatively, Compound S-500 can be synthesized via a variety of different synthetic routes using commercially available starting materials and/or starting materials prepared by conventional synthetic methods.

With continued reference to Scheme 5, Compound S-500 is protected at the amino group to form Compound S-501, wherein $PG^1$ and $PG^2$ are amino protecting groups. Amino protecting groups can be found in T. W. Greene and P. G. M. Wuts, "*Protective Groups in Organic Synthesis*", Fourth edition, Wiley, New York 2006. Representative amino-protecting groups include, but are not limited to, formyl groups; acyl groups, for example alkanoyl groups, such as acetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

In certain embodiments, $PG^1$ and $PG^2$ are Boc groups. Conditions for forming Boc groups on Compound S-501 can be found in Greene and Wuts. One method is reaction of Compound S-500 with di-tert-butyl dicarbonate. The reaction can optionally be run in the presence of an activating agent, such as DMAP.

With continued reference to Scheme 5, the carboxybenzyl group on Compound S-501 is deprotected to form Compound S-502. Conditions to remove the carboxybenzyl group can be found in Greene and Wuts. Methods to remove the carboxybenzyl group include hydrogenolysis of Compound S-501 or treatment of Compound S-501 with HBr. One method to remove the carboxybenzyl group is reaction of Compound S-501 with hydrogen and palladium.

With continued reference to Scheme 5, Compound S-502 is reacted with phosgene to form Compound S-503. Reaction with phosgene forms an acyl chloride on the amino group of Compound S-502. Other reagents can act as substitutes for phosgene, such as diphosgene or triphosgene.

A representative synthesis for Compound S-602 is shown in Scheme 6. In Scheme 6, for Compound KC-8, $R^a$ is hydroxyl; n is 3; the first and third geminal $R^1$ and $R^2$ are hydrogen; the second geminal $R^1$ and $R^2$ are methyl; $R^5$ is methyl; and $PG^1$ and $PG^2$ are optional amino protecting groups.

Scheme 6

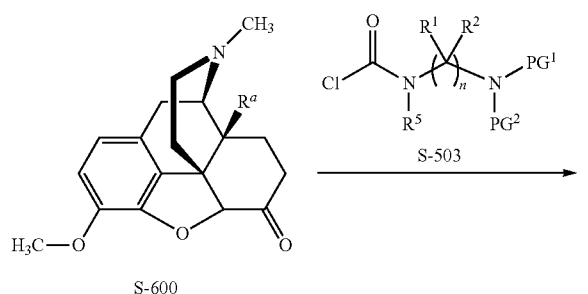

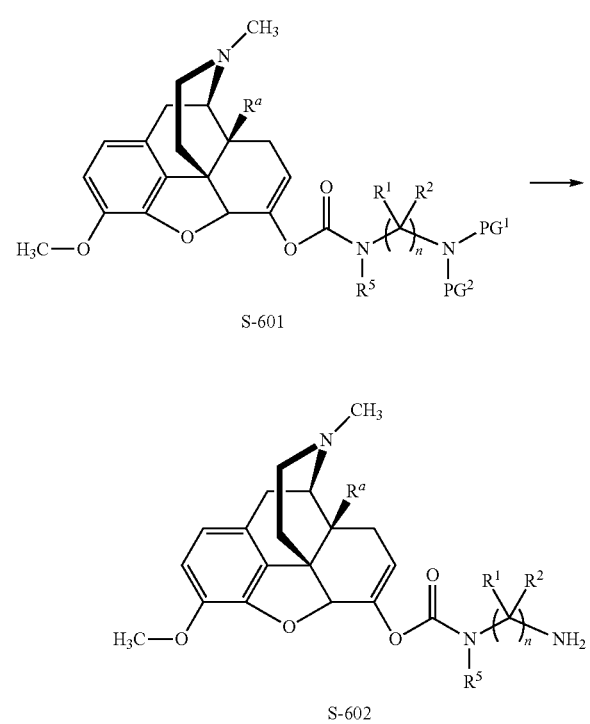

In Scheme 6, Compound S-600 is a commercially available starting material. Alternatively, Compound S-600 can be semi-synthetically derived from natural materials or synthesized via a variety of different synthetic routes using commercially available starting materials and/or starting materials prepared by conventional synthetic methods.

With continued reference to Scheme 6, Compound S-600 is reacted with Compound S-503 to form Compound S-601. In this reaction, the enolate of Compound S-600 reacts with the acyl chloride of Compound S-503 to form a carbamate.

With continued reference to Scheme 6, the optional protecting groups $PG^1$ and $PG^2$ are removed from Compound S-601 to form Compound S-602. Conditions to remove amino groups can be found in Greene and Wuts. When $PG^1$ and/or $PG^2$ are Boc groups, the protecting groups can be removed with acidic conditions, such as treatment with hydrochloric acid or trifluoroacetic acid.

Compound S-602 can be used as in the above schemes, such as Schemes 3 and 4, to prepare Compound KC-8.

As described in more detail herein, the disclosure provides processes and intermediates useful for preparing compounds of the present disclosure or a salt or solvate or stereoisomer thereof. Accordingly, the present disclosure provides a process of preparing a compound of the present disclosure, the process involves:

contacting a compound of formula:

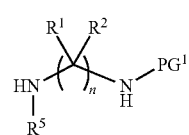

with a compound of formula

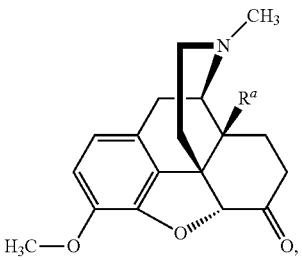

wherein $R^a$ is hydroxyl; n is 3; the first and third geminal $R^1$ and $R^2$ are hydrogen; the second geminal $R^1$ and $R^2$ are methyl; $R^5$ is methyl; and $PG^1$ is an amino protecting group, in the presence of a carbamate-forming reagent.

Accordingly and as described in more detail herein, the present disclosure provides a process of preparing a compound of the present disclosure, the process involves:
contacting a compound of formula:

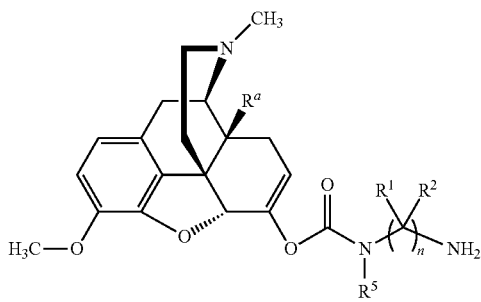

with a compound of formula

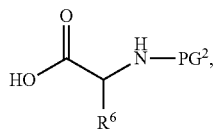

wherein $R^a$ is hydroxyl; n is 3; the first and third geminal $R^1$ and $R^2$ are hydrogen; the second geminal $R^1$ and $R^2$ are methyl; $R^5$ is methyl; $R^6$ is the side chain of arginine; and $PG^2$ is an amino protecting group.

Accordingly and as described in more detail herein, the present disclosure provides a process of preparing a compound of the present disclosure, the process involves: contacting a compound of formula:

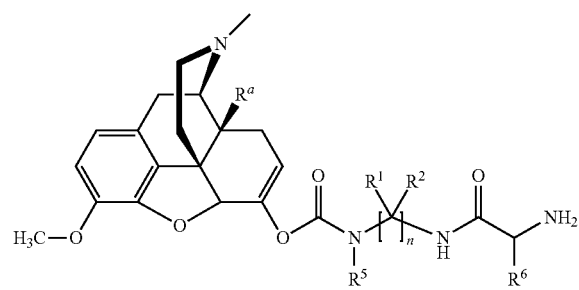

with a compound of formula

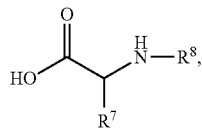

wherein $R^a$ is hydroxyl; n is 3; the first and third geminal $R^1$ and $R^2$ are hydrogen; the second geminal $R^1$ and $R^2$ are methyl; $R^5$ is methyl; $R^6$ is the side chain of arginine; $R^7$ is the side chain of glycine; and $R^8$ is malonyl.

In one instance, the above process can further involve a step of forming a salt of a compound of the present disclosure. Embodiments are directed to the other processes described herein; and to the product prepared by any of the processes described herein.

Trypsin Inhibitors

As disclosed herein, the present disclosure also provides pharmaceutical compositions, and their methods of use, where the pharmaceutical compositions comprise a prodrug, Compound KC-8, that provides controlled release of oxycodone via enzyme cleavage followed by intramolecular cyclization, and a trypsin inhibitor that interacts with the enzyme that mediates the enzymatically-mediated release of oxycodone from the prodrug so as to attenuate enzymatic cleavage of the prodrug. Such disclosure provides for the enzyme being trypsin.

As used herein, the term "trypsin inhibitor" refers to any agent capable of inhibiting the action of trypsin on a substrate. The term "trypsin inhibitor" also encompasses salts of trypsin inhibitors. The ability of an agent to inhibit trypsin can be measured using assays well known in the art. For example, in a typical assay, one unit corresponds to the amount of inhibitor that reduces the trypsin activity by one benzoyl-L-arginine ethyl ester unit (BAEE-U). One BAEE-U is the amount of enzyme that increases the absorbance at 253 nm by 0.001 per minute at pH 7.6 and 25° C. See, for example, K. Ozawa, M. Laskowski, 1966, J. Biol. Chem. 241, 3955 and Y. Birk, 1976, Meth. Enzymol. 45, 700. In certain instances, a trypsin inhibitor can interact with an active site of trypsin, such as the S1 pocket and the S3/4 pocket. The S1 pocket has an aspartate residue which has affinity for a positively charged moiety. The S3/4 pocket is a hydrophobic pocket. The disclosure provides for specific trypsin inhibitors and non-specific serine protease inhibitors.

There are many trypsin inhibitors known in the art, both those specific to trypsin and those that inhibit trypsin and other proteases such as chymotrypsin. The disclosure provides for trypsin inhibitors that are proteins, peptides, and small molecules. The disclosure provides for trypsin inhibitors that are irreversible inhibitors or reversible inhibitors. The disclosure provides for trypsin inhibitors that are competitive inhibitors, non-competitive inhibitors, or uncompetitive inhibitors. The disclosure provides for natural, synthetic or semi-synthetic trypsin inhibitors.

Trypsin inhibitors can be derived from a variety of animal or vegetable sources: for example, soybean, corn, lima and other beans, squash, sunflower, bovine and other animal pancreas and lung, chicken and turkey egg white, soy-based infant formula, and mammalian blood. Trypsin inhibitors can also be of microbial origin: for example, antipain; see, for example, H. Umezawa, 1976, Meth. Enzymol. 45, 678. A trypsin inhibitor can also be an arginine or lysine mimic or other synthetic compound: for example arylguanidine, benzamidine, 3,4-dichloroisocoumarin, diisopropylfluorophosphate, gabexate mesylate, phenylmethanesulfonyl fluoride, or substituted versions or analogs thereof. In certain embodiments, trypsin inhibitors comprise a covalently modifiable group, such as a chloroketone moiety, an aldehyde moiety, or an epoxide moiety. Other examples of trypsin inhibitors are aprotinin, camostat and pentamidine.

As used herein, an arginine or lysine mimic is a compound that is capable of binding to the $P^1$ pocket of trypsin and/or interfering with trypsin active site function. The arginine or lysine mimic can be a cleavable or non-cleavable moiety.

In one embodiment, the trypsin inhibitor is derived from soybean. Trypsin inhibitors derived from soybean (*Glycine max*) are readily available and are considered to be safe for human consumption. They include, but are not limited to, SBTI, which inhibits trypsin, and Bowman-Birk inhibitor, which inhibits trypsin and chymotrypsin. Such trypsin inhibitors are available, for example from Sigma-Aldrich, St. Louis, Mo., USA.

It will be appreciated that the pharmaceutical composition according to the embodiments may further comprise one or more other trypsin inhibitors.

As stated above, a trypsin inhibitor can be an arginine or lysine mimic or other synthetic compound. In certain embodiments, the trypsin inhibitor is an arginine mimic or a lysine mimic, wherein the arginine mimic or lysine mimic is a synthetic compound.

Certain trypsin inhibitors include compounds of formula:

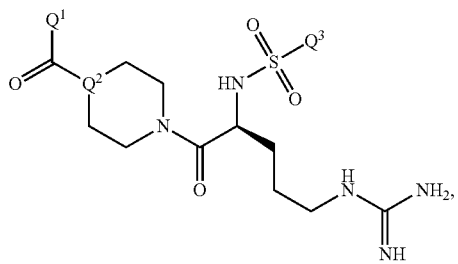

wherein:

$Q^1$ is selected from —O-$Q^4$ or -$Q^4$-COOH, where $Q^4$ is $C_1$-$C_4$ alkyl;

$Q^2$ is N or CH; and $Q^3$ is aryl or substituted aryl.

Certain trypsin inhibitors include compounds of formula:

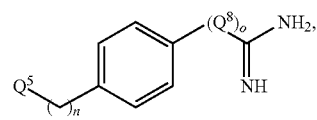

wherein:

$Q^5$ is —C(O)—COOH or —NH-$Q^6$-$Q^7$-SO$_2$—C$_6$H$_5$, where $Q^6$ is —(CH$_2$)$_p$—COOH;

$Q^7$ is —(CH$_2$)—C$_6$H$_5$;

$Q^8$ is NH;

n is a number from zero to two;

o is zero or one;

p is an integer from one to three; and r is an integer from one to three.

Certain trypsin inhibitors include compounds of formula:

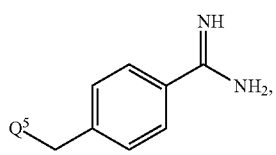

wherein:

$Q^5$ is —C(O)—COOH or —NH-$Q^6$-$Q^7$-SO$_2$—C$_6$H$_5$, where $Q^6$ is —(CH$_2$)$_p$—COOH;

$Q^7$ is —(CH$_2$), C$_6$H$_5$; and p is an integer from one to three; and r is an integer from one to three.

Certain trypsin inhibitors include the following:

| Compound 101 | 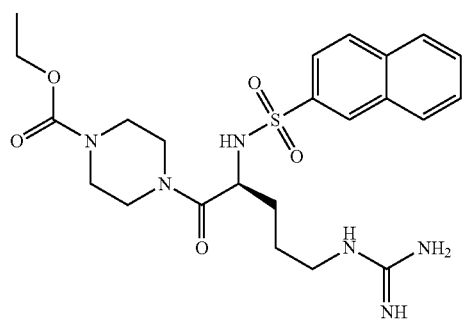 [SMILES: CCOC(=O)N1CCN(C(=O)[C@H](CCCNC(=N)N)NS(=O)(=O)c2ccc3ccccc3c2)CC1] | (S)-ethyl 4-(5-guanidino-2-(naphthalene-2-sulfonamido)pentanoyl)piperazine-1-carboxylate |
| --- | --- | --- |

-continued

| | | |
|---|---|---|
| Compound 102 | 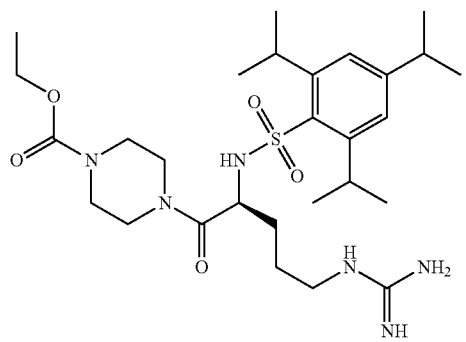 [SMILES: CCOC(=O)N1CCN(C(=O)[C@H](CCCNC(=N)N)NS(=O)(=O)c2c(C(C)C)cc(C(C)C)cc2C(C)C)CC1] | (S)-ethyl 4-(5-guanidino-2-(2,4,6-triisopropylphenylsulfonamido)pentanoyl)piperazine-1-carboxylate |
| Compound 103 | 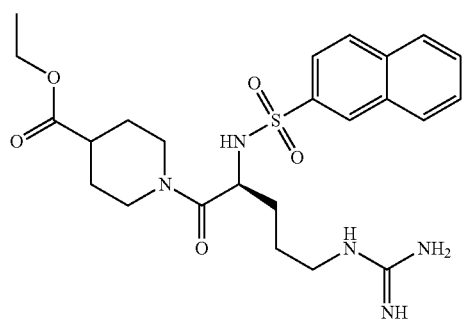 | (S)-ethyl 1-(5-guanidino-2-(naphthalene-2-sulfonamido)pentanoyl)piperidine-4-carboxylate |
| Compound 104 | 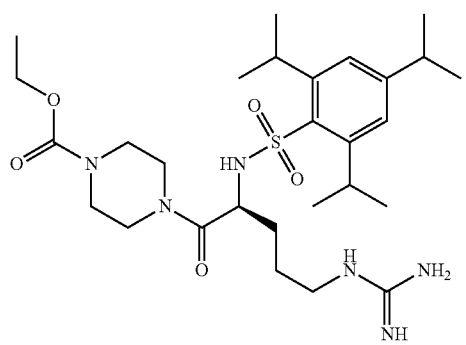 [SMILES: CCOC(=O)N1CCN(C(=O)[C@H](CCCNC(=N)N)NS(=O)(=O)c2c(C(C)C)cc(C(C)C)cc2C(C)C)CC1] | (S)-ethyl 1-(5-guanidino-2-(2,4,6-triisopropylphenylsulfonamido)pentanoyl)piperidine-4-carboxylate |
| Compound 105 | 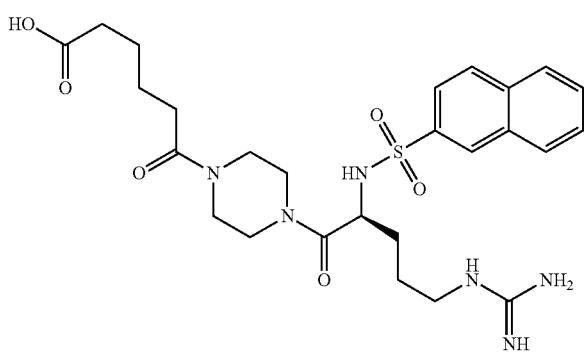 [SMILES: N=C(N)NCCC[C@H](NS(=O)(=O)c1ccc2ccccc2c1)C(=O)N1CCN(C(=O)CCCCC(=O)O)CC1] | (S)-6-(4-(5-guanidino-2-(naphthalene-2-sulfonamido)pentanoyl)piperazin-1-yl)-6-oxohexanoic acid |
| Compound 106 | 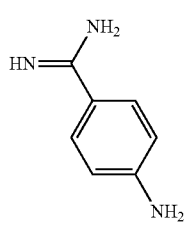 | 4-aminobenzimidamide (also 4-aminobenzamidine) |

-continued

| Compound 107 | 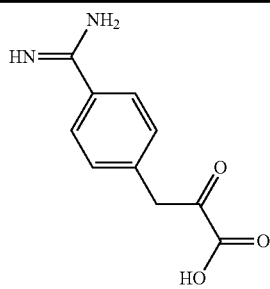 | 3-(4-carbamimidoylphenyl)-2-oxopropanoic acid |
| Compound 108 | 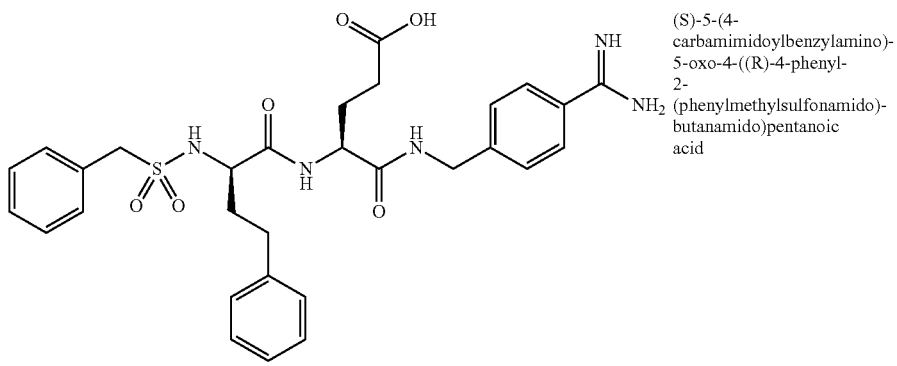 | (S)-5-(4-carbamimidoylbenzylamino)-5-oxo-4-((R)-4-phenyl-2-(phenylmethylsulfonamido)-butanamido)pentanoic acid |
| Compound 109 | 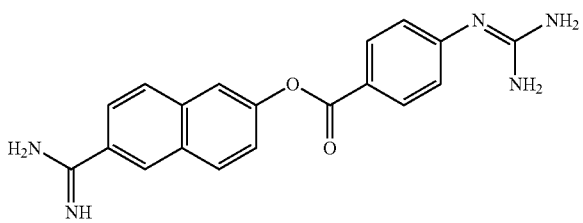 [SMILES: N=C(N)c1ccc2cc(OC(=O)c3ccc(N=C(N)N)cc3)ccc2c1] | 6-carbamimidoylnaphthalen-2-yl 4-(diaminomethyleneamino)benzoate |
| Compound 110 | 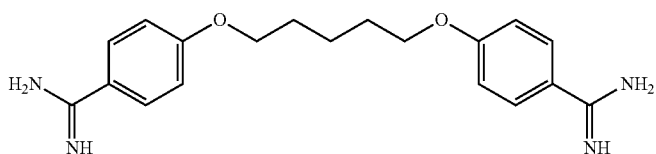 [SMILES: N=C(N)c1ccc(OCCCCCOc2ccc(C(=N)N)cc2)cc1] | 4,4'-(pentane-1,5-diylbis(oxy))dibenzimidamide |

A description of methods to prepare Compound 101, Compound 102, Compound 103, Compound 104, Compound 105, Compound 107, and Compound 108 is provided in PCT International Publication Number WO 2010/045599A1, published 22 Apr. 2010, which is incorporated herein by reference in its entirety. Compound 106, Compound 109, and Compound 110 are commercially available, e.g., from Sigma-Aldrich, St. Louis, Mo., USA.

In certain embodiments, the trypsin inhibitor is SBTI, BBSI, Compound 101, Compound 106, Compound 108, Compound 109, or Compound 110. In certain embodiments, the trypsin inhibitor is camostat.

In certain embodiments, the trypsin inhibitor is a compound of formula T-I:

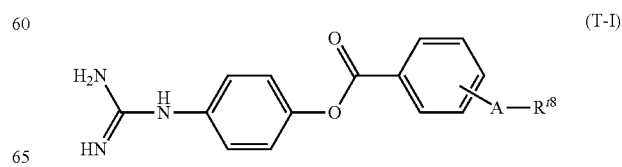

(T-I)

wherein

A represents a group of the following formula:

$$-\underset{R^{t9}}{C}=\underset{R^{t10}}{C}-$$

$R^{t9}$ and $R^{t10}$ each represents independently a hydrogen atom or a $C_{1-4}$ alkyl group, $R^{t8}$ represents a group selected from the following formulae:

$$\text{CON}\begin{matrix}R^{t11}\\R^{t12}\end{matrix},\quad \text{CON}\begin{matrix}R^{t11}\\R^{t13}\end{matrix}R^{t12},\quad \text{or}\quad \text{CON}\!\!\bigcirc\!\!-R^{t14}$$

wherein R each represents independently
(1) a hydrogen atom,
(2) a phenyl group,
(3) a $C_{1-4}$ alkyl group substituted by a phenyl group,
(4) a $C_{1-10}$ alkyl group,
(5) a $C_{1-10}$ alkoxyl group,
(6) a $C_{2-10}$ alkenyl group having 1 to 3 double bonds,
(7) a $C_{2-10}$ alkynyl group having 1 to 2 triple bonds,
(8) a group of formula: $R^{t15}$—C(O)X$R^{t16}$,
wherein $R^{t15}$ represents a single bond or a $C_{1-8}$ alkylene group,
X represents an oxygen atom or an NH-group, and
$R^{t16}$ represents a hydrogen atom, a $C_{1-4}$ alkyl group, a phenyl group or a $C_{1-4}$ alkyl group substituted by a phenyl group, or
(9) a $C_{3-7}$ cycloalkyl group;
the structure represents a 4-7 membered monocyclic hetero-ring containing 1 to 2 nitrogen or oxygen atoms, $R^{t14}$ represents a hydrogen atom, a $C_{1-4}$ alkyl group substituted by a phenyl group or a group of formula: COOR$^{t17}$, wherein $R^{t17}$ represents a hydrogen atom, a $C_{1-4}$ alkyl group or a $C_{1-4}$ alkyl group substituted by a phenyl group;

provided that $R^{t11}$, $R^{t12}$ and $R^{t13}$ do not represent simultaneously hydrogen atoms;

or nontoxic salts, acid addition salts or hydrates thereof.

In certain embodiments, the trypsin inhibitor is a compound selected from the following:

In certain embodiments, the trypsin inhibitor is a compound of formula T-II:

(T-II)

wherein
X is NH;
n is zero or one; and
$R^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH$_2$)$_m$—C(O)—O—(CH$_2$)$_m$—C(O)—N—R$^{n1}$R$^{n2}$, wherein each m is independently zero to 2; and R$^{n1}$ and R$^{n2}$ are independently selected from hydrogen and $C_{1-4}$ alkyl.

In certain embodiments, in formula T-II, $R^{t1}$ is guanidino or amidino.

In certain embodiments, in formula T-II, $R^{t1}$ is —(CH$_2$)$_m$—C(O)—O—(CH$_2$)$_m$—C(O)—N—R$^{n1}$R$^{n2}$, wherein m is one and R$^{n1}$ and R$^{n2}$ are methyl.

In certain embodiments, the trypsin inhibitor is a compound of formula T-III:

(T-III)

wherein
X is NH;
n is zero or one;
$L^{t1}$ is selected from —C(O)—O—; —O—C(O)—; —O—(CH$_2$)$_m$—O—; —OCH$_2$—Ar$^{t2}$—CH$_2$O—; —C(O)—NR$^{t3}$—; and —NR$^{t3}$—C(O)—;
$R^{t3}$ is selected from hydrogen, $C_{1-6}$ alkyl, and substituted $C_{1-6}$ alkyl;
Ar$^{t1}$ and Ar$^{t2}$ are independently a substituted or unsubstituted aryl group;
m is a number from 1 to 3; and
$R^{t2}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH$_2$)$_m$—C(O)—O—(CH$_2$)$_m$—C(O)_N_R$^{n1}$R$^{n2}$, wherein each m is independently zero to 2; and R$^{n1}$ and R$^{n2}$ are independently selected from hydrogen and C$_{1-4}$ alkyl.

In certain embodiments, in formula T-III, R$^{t2}$ is guanidino or amidino.

In certain embodiments, in formula T-III, R$^{t2}$ is —(CH$_2$)$_m$—C(O)—O—(CH$_2$)$_m$—C(O)—N—R$^{n1}$R$^{n2}$, wherein m is one and R$^{n1}$ and R$^{n2}$ are methyl.

In certain embodiments, the trypsin inhibitor is a compound of formula T-IV:

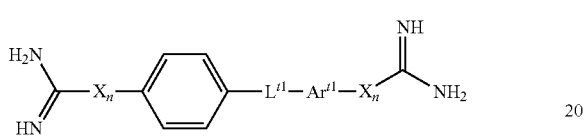

(T-IV)

wherein
each X is NH;
each n is independently zero or one;
L$^{t1}$ is selected from —C(O)—O—; —O—C(O)—; —O—(CH$_2$)$_m$—O—; —OCH$_2$—Ar$^{t2}$—CH$_2$O—; —C(O)—NR$^{t3}$—; and —NR$^{t3}$—C(O)—;
R$^{t3}$ is selected from hydrogen, C$_{1-6}$ alkyl, and substituted C$_{1-6}$ alkyl;
Ar$^{t1}$ and Ar$^{t2}$ are independently a substituted or unsubstituted aryl group; and
m is a number from 1 to 3.

In certain embodiments, in formula T-IV, Ar$^{t1}$ or Ar$^{t2}$ is phenyl.

In certain embodiments, in formula T-IV, Ar$^{t1}$ or Ar$^{t2}$ is naphthyl.

In certain embodiments, the trypsin inhibitor is Compound 109.

In certain embodiments, the trypsin inhibitor is

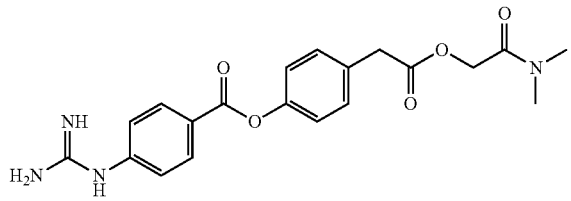 [SMILES: CN(C)C(=O)COC(=O)Cc1ccc(OC(=O)c2ccc(NC(=N)N)cc2)cc1]

In certain embodiments, the trypsin inhibitor is Compound 110 or a bis-arylamidine variant thereof; see, for example, J. D. Geratz, M. C.-F. Cheng and R. R. Tidwell (1976) J. Med. Chem. 19, 634-639.

It is to be appreciated that the invention also includes inhibitors of other enzymes involved in protein assimilation that can be used in combination with Compound KC-8 to attenuate release of oxycodone from the prodrug.

Combinations of Prodrug and Trypsin Inhibitor

As discussed above, the present disclosure provides pharmaceutical compositions which comprise a trypsin inhibitor and Compound KC-8, a ketone-modified oxycodone prodrug, that comprises a promoiety comprising a trypsin-cleavable moiety that, when cleaved, facilitates release of oxycodone. Examples of compositions containing Compound KC-8 and a trypsin inhibitor are described below.

The embodiments provide a pharmaceutical composition, which comprises a compound of Formulae T-I to T-IV and Compound KC-8, or a pharmaceutically acceptable salt thereof. The embodiments provide a pharmaceutical composition, which comprises Compound 109 and Compound KC-8, or a pharmaceutically acceptable salt thereof.

Certain embodiments provide for a combination of Compound KC-8 and a trypsin inhibitor, in which the trypsin inhibitor is shown in the following table.

| Prodrug | Trypsin inhibitor |
|---|---|
| Compound KC-8 | SBTI |
| Compound KC-8 | BBSI |
| Compound KC-8 | Compound 101 |
| Compound KC-8 | Compound 106 |
| Compound KC-8 | Compound 108 |
| Compound KC-8 | Compound 109 |
| Compound KC-8 | Compound 110 |
| Compound KC-8 | camostat |

Combinations of Compound KC-8 and Other Drugs

The disclosure provides for Compound KC-8 and a further prodrug or drug included in a pharmaceutical composition. Such a prodrug or drug would provide additional analgesia or other benefits. Examples include opioids, acetaminophen, non-steroidal anti-inflammatory drugs (NSAIDs) and other analgesics. In one embodiment, Compound KC-8 would be combined with an opioid antagonist prodrug or drug. Other examples include drugs or prodrugs that have benefits other than, or in addition to, analgesia. The embodiments provide a pharmaceutical composition, which comprises Compound KC-8 and acetaminophen, or a pharmaceutically acceptable salt thereof.

Such compositions can also comprise a trypsin inhibitor. In certain embodiments, the trypsin inhibitor is selected from SBTI, BBSI, Compound 101, Compound 106, Compound 108, Compound 109, and Compound 110. In certain embodiments, the trypsin inhibitor is Compound 109. In certain embodiments, the trypsin inhibitor is camostat.

In certain embodiments, a pharmaceutical composition can comprise Compound KC-8, a non-opioid drug and at least one opioid or opioid prodrug.

Pharmaceutical Compositions and Methods of Use

As disclosed herein, the embodiments provide a composition, which comprises N-1-[3-(oxycodone-6-enol-carbonyl-methyl-amino)-2,2-dimethyl-propylamine]-arginine-glycine-malonic acid, Compound KC-8. The pharmaceutical composition according to the embodiments can further comprise a pharmaceutically acceptable carrier. The composition is conveniently formulated in a form suitable for oral (including buccal and sublingual) administration, for example as a tablet, capsule, thin film, powder, suspension, solution, syrup, dispersion or emulsion. The composition can contain components conventional in pharmaceutical preparations, e.g. one or more carriers, binders, lubricants, excipients (e.g., to impart controlled release characteristics), pH modifiers, sweeteners, bulking agents, coloring agents or further active agents.

Patients can be humans, and also other mammals, such as livestock, zoo animals and companion animals, such as a cat, dog or horse.

In another aspect, the embodiments provide a pharmaceutical composition as described hereinabove for use in the treatment of pain. The pharmaceutical composition according to the embodiments is useful, for example, in the treatment of a patient suffering from, or at risk of suffering from, pain. Accordingly, the present disclosure provides methods of treating or preventing pain in a subject, the methods involving administering to the subject a disclosed composition. The present disclosure provides for a disclosed composition for use in therapy or prevention or as a medicament. The present disclosure also provides the use of a disclosed composition for the manufacture of a medicament, especially for the manufacture of a medicament for the treatment or prevention of pain.

The compositions of the present disclosure can be used in the treatment or prevention of pain including, but not limited to include, acute pain, chronic pain, neuropathic pain, acute traumatic pain, arthritic pain, osteoarthritic pain, rheumatoid arthritic pain, muscular skeletal pain, post-dental surgical pain, dental pain, myofascial pain, cancer pain, visceral pain, diabetic pain, muscular pain, post-herpetic neuralgic pain, chronic pelvic pain, endometriosis pain, pelvic inflammatory pain and child birth related pain. Acute pain includes, but is not limited to, acute traumatic pain or post-surgical pain. Chronic pain includes, but is not limited to, neuropathic pain, arthritic pain, osteoarthritic pain, rheumatoid arthritic pain, muscular skeletal pain, dental pain, myofascial pain, cancer pain, diabetic pain, visceral pain, muscular pain, post-herpetic neuralgic pain, chronic pelvic pain, endometriosis pain, pelvic inflammatory pain and back pain.

The present disclosure also provides use of Compound KC-8 in the treatment of pain. The present disclosure also provides use of Compound KC-8 in the prevention of pain.

The present disclosure provides use of Compound KC-8 in the manufacture of a medicament for treatment of pain. The present disclosure provides use of Compound KC-8 in the manufacture of a medicament for prevention of pain.

In another aspect, the embodiments provide a method of treating pain in a patient in need thereof, which comprises administering an effective amount of a pharmaceutical composition as described hereinabove. In another aspect, the embodiments provide a method of preventing pain in a patient in need thereof, which comprises administering an effective amount of a pharmaceutical composition as described hereinabove.

The amount of composition disclosed herein to be administered to a patient to be effective (i.e. to provide blood levels of oxycodone sufficient to be effective in the treatment or prophylaxis of pain) will depend upon the bioavailability of the particular composition, the susceptibility of the particular composition to enzyme activation in the gut, as well as other factors, such as the species, age, weight, sex, and condition of the patient, manner of administration and judgment of the prescribing physician. If the composition also comprises a trypsin inhibitor, the amount of composition disclosed herein to be administered to a patient would also depend on the amount and potency of trypsin inhibitor present in the composition. In general, the composition dose can be such that Compound KC-8 is in the range of from 0.01 milligrams prodrug per kilogram to 20 milligrams prodrug per kilogram (mg/kg) body weight. For example, a composition comprising Compound KC-8 can be administered at a dose equivalent to administering free oxycodone in the range of from 0.02 to 0.5 mg/kg body weight or 0.01 mg/kg to 10 mg/kg body weight or 0.01 to 2 mg/kg body weight. In one embodiment, the composition can be administered at a dose such that the level of oxycodone achieved in the blood is in the range of from 0.5 ng/ml to 10 ng/ml.

As disclosed above, the present disclosure also provides pharmaceutical compositions which comprise a trypsin inhibitor and Compound KC-8, a phenol-modified oxycodone prodrug, that comprises a promoiety comprising a trypsin-cleavable moiety that, when cleaved, facilitates release of oxycodone. In such pharmaceutical compositions, the amount of a trypsin inhibitor to be administered to the patient to be effective (i.e. to attenuate release of oxycodone when administration of Compound KC-8 alone would lead to overexposure of oxycodone) will depend upon the effective dose of Compound KC-8 and the potency of the particular trypsin inhibitor, as well as other factors, such as the species, age, weight, sex and condition of the patient, manner of administration and judgment of the prescribing physician. In general, the dose of trypsin inhibitor can be in the range of from 0.05 mg to 50 mg per mg of Compound KC-8. In a certain embodiment, the dose of trypsin inhibitor can be in the range of from 0.001 mg to 50 mg per mg of Compound KC-8. In one embodiment, the dose of trypsin inhibitor can be in the range of from 0.01 nanomoles to 100 micromoles per micromole of Compound KC-8.

Representative Embodiments of Dose Units of Prodrug Compound KC-8 and Trypsin Inhibitor Having a Desired Pharmacokinetic Profile The embodiments include a composition that comprises (a) a prodrug comprising oxycodone covalently bound through the enolic oxygen to a promoiety comprising a trypsin-cleavable moiety, wherein cleavage of the trypsin-cleavable moiety by trypsin mediates release of oxycodone, wherein the prodrug is Compound KC-8 and (b) a trypsin inhibitor that interacts with the trypsin that mediates enzymatically-controlled release of oxycodone from the prodrug following ingestion of the composition.

The embodiments include a dose unit comprising a composition, such as a pharmaceutical composition, comprising Compound KC-8, a ketone-modified prodrug, and a trypsin inhibitor, where Compound KC-8 and trypsin inhibitor are present in the dose unit in an amount effective to provide for a pre-selected pharmacokinetic (PK) profile following ingestion. In further embodiments, the pre-selected PK profile comprises at least one PK parameter value that is less than the PK parameter value of oxycodone released following ingestion of an equivalent dosage of Compound KC-8 in the absence of inhibitor. In further embodiments, the PK parameter value is selected from an oxycodone Cmax value, an oxycodone exposure value, and a (1/oxycodone Tmax) value.

In certain embodiments, the dose unit provides for a pre-selected PK profile following ingestion of at least two dose units. In related embodiments, the pre-selected PK profile of such dose units is modified relative to the PK profile following ingestion of an equivalent dosage of Compound KC-8 without inhibitor. In related embodiments, such a dose unit provides that ingestion of an increasing number of the dose units provides for a linear PK profile. In related embodiments, such a dose unit provides that ingestion of an increasing number of the dose units provides for a nonlinear PK profile. In related embodiments, the PK parameter value of the PK profile of such a dose unit is selected from an oxycodone Cmax value, a (1/oxycodone Tmax) value, and an oxycodone exposure value.

The embodiments include methods for treating a patient comprising administering any of the compositions, such as pharmaceutical compositions, comprising Compound KC-8 and a trypsin inhibitor or dose units described herein to a patient in need thereof. The embodiments include methods to reduce side effects of a therapy comprising administering any of such compositions, e.g., pharmaceutical compositions, or dose units described herein to a patient in need thereof. The embodiments include methods of improving patient compliance with a therapy prescribed by a clinician comprising directing administration of any of such compositions, e.g., pharmaceutical compositions, or dose units described herein to a patient in need thereof. Such embodiments can provide for improved patient compliance with a prescribed therapy as compared to patient compliance with a prescribed therapy using drug and/or using prodrug without inhibitor as compared to prodrug with inhibitor.

The embodiments include methods of reducing risk of unintended overdose of oxycodone comprising directing administration of any of such compositions, e.g., pharmaceutical compositions, or dose units described herein to a patient in need of treatment.

The embodiments include methods of making a dose unit comprising combining Compound KC-8 and a trypsin inhibitor in a dose unit, wherein Compound KC-8 and trypsin inhibitor are present in the dose unit in an amount effective to attenuate release of oxycodone from Compound KC-8.

The embodiments include methods of deterring misuse or abuse of multiple dose units of Compound KC-8 comprising combining Compound KC-8 and a trypsin inhibitor in a dose unit, wherein Compound KC-8 and trypsin inhibitor are present in the dose unit in an amount effective to attenuate release of oxycodone from Compound KC-8 such that ingestion of multiples of dose units by a patient does not provide a proportional release of oxycodone. In further embodiments, release of drug is decreased compared to release of drug by an equivalent dosage of prodrug in the absence of inhibitor.

One embodiment is a method for identifying a trypsin inhibitor and prodrug Compound KC-8 suitable for formulation in a dose unit. Such a method can be conducted as, for example, an in vitro assay, an in vivo assay, or an ex vivo assay.

The embodiments include methods for identifying a trypsin inhibitor and prodrug Compound KC-8 suitable for formulation in a dose unit comprising combining prodrug Compound KC-8, a trypsin inhibitor, and trypsin in a reaction mixture, and detecting prodrug conversion, wherein a decrease in prodrug conversion in the presence of the trypsin inhibitor as compared to prodrug conversion in the absence of the trypsin inhibitor indicates the trypsin inhibitor and prodrug Compound KC-8 are suitable for formulation in a dose unit.

The embodiments include methods for identifying a trypsin inhibitor and prodrug Compound KC-8 suitable for formulation in a dose unit comprising administering to an animal a trypsin inhibitor and prodrug Compound KC-8 and detecting prodrug conversion, wherein a decrease in oxycodone conversion in the presence of the trypsin inhibitor as compared to oxycodone conversion in the absence of the trypsin inhibitor indicates the trypsin inhibitor and prodrug Compound KC-8 are suitable for formulation in a dose unit. In certain embodiments, administering comprises administering to the animal increasing doses of inhibitor co-dosed with a selected fixed dose of prodrug. Detecting prodrug conversion can facilitate identification of a dose of inhibitor and a dose of prodrug that provides for a pre-selected pharmacokinetic (PK) profile. Such methods can be conducted as, for example, an in vivo assay or an ex vivo assay.

The embodiments include methods for identifying a trypsin inhibitor and prodrug Compound KC-8 suitable for formulation in a dose unit comprising administering to an animal tissue a trypsin inhibitor and prodrug Compound KC-8 and detecting prodrug conversion, wherein a decrease in prodrug conversion in the presence of the trypsin inhibitor as compared to prodrug conversion in the absence of the trypsin inhibitor indicates the trypsin inhibitor and prodrug Compound KC-8 are suitable for formulation in a dose unit.

Dose Units of Prodrug Compound KC-8 and Trypsin Inhibitor Having a Desired Pharmacokinetic Profile The present disclosure provides dose units of prodrug and inhibitor that can provide for a desired pharmacokinetic (PK) profile. Dose units can provide a modified PK profile compared to a reference PK profile as disclosed herein. It will be appreciated that a modified PK profile can provide for a modified pharmacodynamic (PD) profile. Ingestion of multiples of such a dose unit can also provide a desired PK profile.

Unless specifically stated otherwise, "dose unit" as used herein refers to a combination of a trypsin-cleavable prodrug and a trypsin inhibitor. A "single dose unit" is a single unit of a combination of a trypsin-cleavable prodrug and a trypsin inhibitor, where the single dose unit provide a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

As used herein, a "PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile".) A PK profile is characterized by PK parameters.

As used herein, a "PK parameter" refers to a measure of drug concentration in blood or plasma, such as: 1) "drug Cmax", the maximum concentration of drug achieved in blood or plasma; 2) "drug $T_{max}$", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

For purposes of describing the features of dose units of the present disclosure, "PK parameter values" that define a PK profile include drug Cmax (e.g., oxycodone Cmax), total drug exposure (e.g., area under the curve) (e.g., oxycodone exposure) and 1/(drug Tmax) (such that a decreased 1/Tmax is indicative of a delay in Tmax relative to a reference Tmax) (e.g., 1/oxycodone Tmax). Thus a decrease in a PK parameter value relative to a reference PK parameter value can indicate, for example, a decrease in drug Cmax, a decrease in drug exposure, and/or a delayed $T_{max}$.

Dose units of the present disclosure can be adapted to provide for a modified PK profile, e.g., a PK profile that is different from that achieved from dosing a given dose of prodrug in the absence of inhibitor (i.e., without inhibitor). For example, dose units can provide for at least one of decreased drug Cmax, delayed drug Tmax and/or decreased drug exposure compared to ingestion of a dose of prodrug in the same amount but in the absence of inhibitor. Such a modification is due to the inclusion of an inhibitor in the dose unit.

As used herein, "a pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax), and side effects.

FIG. 1 is a schematic illustrating an example of the effect of increasing inhibitor concentrations upon the PK parameter drug Cmax for a fixed dose of prodrug. At low concentrations of inhibitor, there may be no detectable effect on drug release, as illustrated by the plateau portion of the plot of drug Cmax (Y axis) versus inhibitor concentration (X axis). As inhibitor concentration increases, a concentration is reached at which drug release from prodrug is attenuated, causing a decrease in, or suppression of, drug Cmax. Thus, the effect of inhibitor upon a prodrug PK parameter for a dose unit of the present disclosure can range from undetectable, to moderate, to complete inhibition (i.e., no detectable drug release).

A dose unit can be adapted to provide for a desired PK profile (e.g., a concentration-time PK profile) following ingestion of a single dose. A dose unit can be adapted to provide for a desired PK profile (e.g., a concentration-dose PK profile) following ingestion of multiple dose units (e.g., at least 2, at least 3, at least 4 or more dose units).

Dose Units Providing Modified PK Profiles

A combination of a prodrug and an inhibitor in a dose unit can provide a desired (or "pre-selected") PK profile (e.g., a concentration-time PK profile) following ingestion of a single dose. The PK profile of such a dose unit can be characterized by one or more of a pre-selected drug Cmax, a pre-selected drug Tmax or a pre-selected drug exposure. The PK profile of the dose unit can be modified compared to a PK profile achieved from the equivalent dosage of prodrug in the absence of inhibitor (i.e., a dose that is the same as the dose unit except that it lacks inhibitor).

A modified PK profile can have a decreased PK parameter value relative to a reference PK parameter value (e.g., a PK parameter value of a PK profile following ingestion of a dosage of prodrug that is equivalent to a dose unit except without inhibitor). For example, a dose unit can provide for a decreased drug Cmax, decreased drug exposure, and/or delayed drug Tmax.

Figure 2:
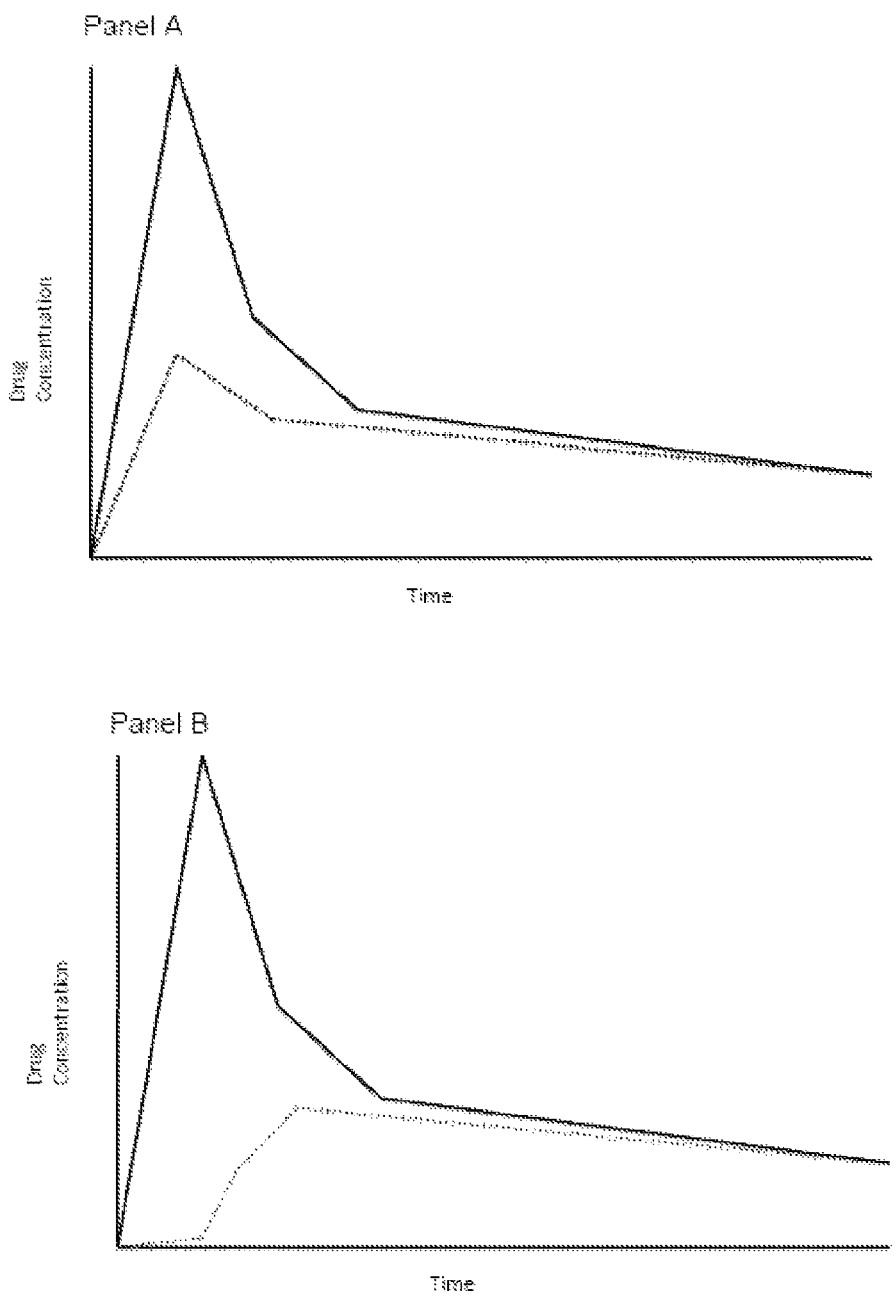
FIG. 2 provides schematics of drug concentration in plasma (Y axis) over time. Panel A is a schematic of a pharmacokinetic (PK) profile following ingestion of prodrug with a trypsin inhibitor (dashed line) where the drug Cmax is modified relative to that of prodrug without inhibitor (solid line). Panel B is a schematic of a PK profile following ingestion of prodrug with inhibitor (dashed line) where drug Cmax and drug Tmax are modified relative to that of prodrug without inhibitor (solid line). Panel C is a schematic of a PK profile following ingestion of prodrug with inhibitor (dashed line) where drug Tmax is modified relative to that of prodrug without inhibitor (solid line).
Figure 2:
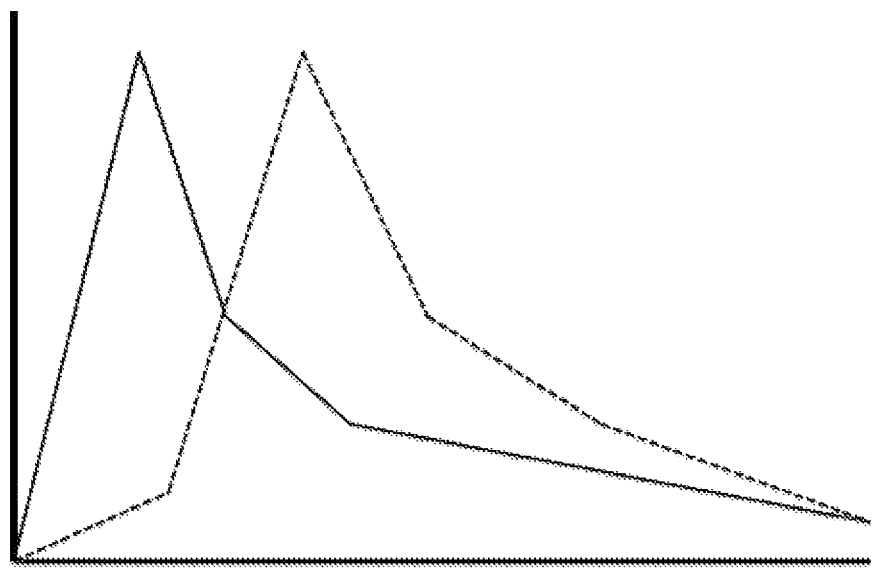

FIG. 2 presents schematic graphs showing examples of modified concentration-time PK profiles of a single dose unit. Panel A is a schematic of drug concentration in blood or plasma (Y axis) following a period of time (X axis) after ingestion of prodrug in the absence or presence of inhibitor. The solid, top line in Panel A provides an example of drug concentration following ingestion of prodrug without inhibitor. The dashed, lower line in Panel A represents drug concentration following ingestion of the same dose of prodrug with inhibitor. Ingestion of inhibitor with prodrug provides for a decreased drug Cmax relative to the drug Cmax that results from ingestion of the same amount of prodrug in the absence of inhibitor. Panel A also illustrates that the total drug exposure following ingestion of prodrug with inhibitor is also decreased relative to ingestion of the same amount of prodrug without inhibitor.

Panel B of FIG. 2 provides another example of a dose unit having a modified concentration-time PK profile. As in Panel A, the solid top line represents drug concentration over time in blood or plasma following ingestion of prodrug without inhibitor, while the dashed lower line represents drug concentration following ingestion of the same amount of prodrug with inhibitor. In this example, the dose unit provides a PK profile having a decreased drug Cmax, decreased drug exposure, and a delayed drug Tmax (i.e., decreased (1/drug Tmax) relative to ingestion of the same dose of prodrug without inhibitor.

Panel C of FIG. 2 provides another example of a dose unit having a modified concentration-time PK profile. As in Panel A, the solid line represents drug concentration over time in blood or plasma following ingestion of prodrug without inhibitor, while the dashed line represents drug concentration following ingestion of the same amount of prodrug with inhibitor. In this example, the dose unit provides a PK profile having a delayed drug Tmax (i.e., decreased (1/drug Tmax) relative to ingestion of the same dose of prodrug without inhibitor.

Dose units that provide for a modified PK profile (e.g., a decreased drug Cmax and/or delayed drug Tmax as compared to, a PK profile of drug or a PK profile of prodrug without inhibitor), find use in tailoring of drug dose according to a patient's needs (e.g., through selection of a particular dose unit and/or selection of a dosage regimen), reduction of side effects, and/or improvement in patient compliance (as compared to side effects or patient compliance associated with drug or with prodrug without inhibitor). As used herein, "patient compliance" refers to whether a patient follows the direction of a clinician (e.g., a physician) including ingestion of a dose that is neither significantly above nor significantly below that prescribed. Such dose units also reduce the risk of misuse, abuse or overdose by a patient as compared to such risk(s) associated with drug or prodrug without inhibitor. For example, dose units with a decreased drug Cmax provide less reward for ingestion than does a dose of the same amount of drug, and/or the same amount of prodrug without inhibitor.

Dose Units Providing Modified PK Profiles Upon Ingestion of Multiple Dose Units

A dose unit of the present disclosure can be adapted to provide for a desired PK profile (e.g., a concentration-time PK profile or concentration-dose PK profile) following ingestion of multiples of a dose unit (e.g., at least 2, at least 3, at least 4, or more dose units). A concentration-dose PK profile refers to the relationship between a selected PK parameter and a number of single dose units ingested. Such a profile can be dose proportional, linear (a linear PK profile) or nonlinear (a nonlinear PK profile). A modified concentration-dose PK profile can be provided by adjusting the relative amounts of prodrug and inhibitor contained in a single dose unit and/or by using a different prodrug and/or inhibitor.

Figure 3:
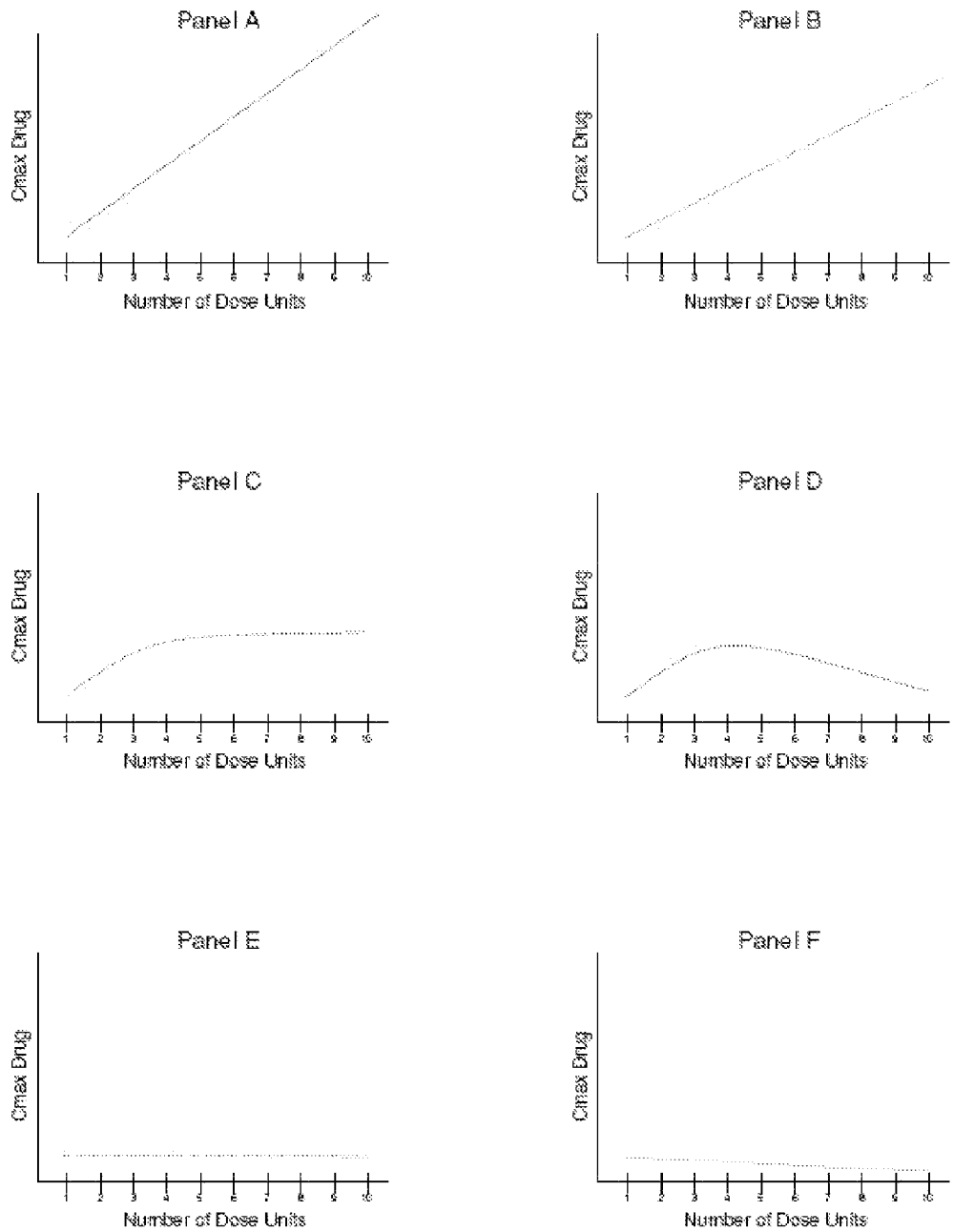
FIG. 3 provides schematics representing differential concentration-dose PK profiles that can result from the dosing of multiples of a dose unit (X axis) of the present disclosure. Different PK profiles (as exemplified herein for a representative PK parameter, drug Cmax (Y axis)) can be provided by adjusting the relative amount of prodrug and trypsin inhibitor contained in a single dose unit or by using a different prodrug or inhibitor in the dose unit.

FIG. 3 provides schematics of examples of concentration-dose PK profiles (exemplified by drug Cmax, Y axis) that can be provided by ingestion of multiples of a dose unit (X axis) of the present disclosure. Each profile can be compared to a concentration-dose PK profile provided by increasing doses of drug alone, where the amount of drug in the blood or plasma from one dose represents a therapeutically effective amount equivalent to the amount of drug released into the blood or plasma by one dose unit of the disclosure. Such a "drug alone" PK profile is typically dose proportional, having a forty-five degree angle positive linear slope. It is also to be appreciated that a concentration-dose PK profile resulting from ingestion of multiples of a dose unit of the disclosure can also be compared to other references, such as a concentration-dose PK profile provided by ingestion of an increasing number of doses of prodrug without inhibitor wherein the amount of drug released into the blood or plasma by a single dose of prodrug in the absence of inhibitor represents a therapeutically effective amount equivalent to the amount of drug released into the blood or plasma by one dose unit of the disclosure.

As illustrated by the relationship between prodrug and inhibitor concentration in FIG. 1, a dose unit can include inhibitor in an amount that does not detectably affect drug release following ingestion. Ingestion of multiples of such a dose unit can provide a concentration-dose PK profile such that the relationship between number of dose units ingested and PK parameter value is linear with a positive slope, which is similar to, for example, a dose proportional PK profile of increasing amounts of prodrug alone. Panel A of FIG. 3 depicts such a profile. Dose units that provide a concentration-dose PK profile having such an undetectable change in drug Cmax in vivo compared to the profile of prodrug alone can find use in thwarting enzyme conversion of prodrug from a dose unit that has sufficient inhibitor to reduce or prevent in vitro cleavage of the enzyme-cleavable prodrug by its respective enzyme.

Panel B in FIG. 3 represents a concentration-dose PK profile such that the relationship between the number of dose units ingested and a PK parameter value is linear with positive slope, where the profile exhibits a reduced slope relative to panel A. Such a dose unit provides a profile having a decreased PK parameter value (e.g., drug Cmax) relative to a reference PK parameter value exhibiting dose proportionality.

Concentration-dose PK profiles following ingestion of multiples of a dose unit can be non-linear. Panel C in FIG. 3 represents an example of a non-linear, biphasic concentration-dose PK profile. In this example, the biphasic concentration-dose PK profile contains a first phase over which the concentration-dose PK profile has a positive rise, and then a second phase over which the relationship between number of dose units ingested and a PK parameter value (e.g., drug Cmax) is relatively flat (substantially linear with zero slope). For such a dose unit, for example, drug Cmax can be increased for a selected number of dose units (e.g., 2, 3, or 4 dose units). However, ingestion of additional dose units does not provide for a significant increase in drug Cmax.

Panel D in FIG. 3 represents another example of a non-linear, biphasic concentration-dose PK profile. In this example, the biphasic concentration-dose PK profile is characterized by a first phase over which the concentration-dose PK profile has a positive rise and a second phase over which the relationship between number of dose units ingested and a PK parameter value (e.g., drug Cmax) declines. Dose units that provide this concentration-dose PK profile provide for an increase in drug Cmax for a selected number of ingested dose units (e.g., 2, 3, or 4 dose units). However, ingestion of further additional dose units does not provide for a significant increase in drug Cmax and instead provides for decreased drug Cmax.

Panel E in FIG. 3 represents a concentration-dose PK profile in which the relationship between the number of dose units ingested and a PK parameter (e.g., drug Cmax) is linear with zero slope. Such dose units do not provide for a significant increase or decrease in drug Cmax with ingestion of multiples of dose units.

Panel F in FIG. 3 represents a concentration-dose PK profile in which the relationship between number of dose units ingested and a PK parameter value (e.g., drug Cmax) is linear with a negative slope. Thus drug Cmax decreases as the number of dose units ingested increases.

Dose units that provide for concentration-dose PK profiles when multiples of a dose unit are ingested find use in tailoring of a dosage regimen to provide a therapeutic level of released drug while reducing the risk of overdose, misuse, or abuse. Such reduction in risk can be compared to a reference, e.g., to administration of drug alone or prodrug alone. In one embodiment, risk is reduced compared to administration of a drug or prodrug that provides a proportional concentration-dose PK profile. A dose unit that provides for a concentration-dose PK profile can reduce the risk of patient overdose through inadvertent ingestion of dose units above a prescribed dosage. Such a dose unit can reduce the risk of patient misuse (e.g., through self-medication). Such a dose unit can discourage abuse through deliberate ingestion of multiple dose units. For example, a dose unit that provides for a biphasic concentration-dose PK profile can allow for an increase in drug release for a limited number of dose units ingested, after which an increase in drug release with ingestion of more dose units is not realized. In another example, a dose unit that provides for a concentration-dose PK profile of zero slope can allow for retention of a similar drug release profile regardless of the number of dose units ingested.

Ingestion of multiples of a dose unit can provide for adjustment of a PK parameter value relative to that of ingestion of multiples of the same dose (either as drug alone or as a prodrug) in the absence of inhibitor such that, for example, ingestion of a selected number (e.g., 2, 3, 4 or more) of a single dose unit provides for a decrease in a PK parameter value compared to ingestion of the same number of doses in the absence of inhibitor.

Pharmaceutical compositions include those having an inhibitor to provide for protection of a therapeutic compound from degradation in the GI tract. Inhibitor can be combined with a drug (i.e., not a prodrug) to provide for protection of the drug from degradation in the GI system. In this example, the composition of inhibitor and drug provide for a modified PK profile by increasing a PK parameter. Inhibitor can also be combined with a prodrug that is susceptible to degradation by a GI enzyme and has a site of action outside the GI tract. In this composition, the inhibitor protects ingested prodrug in the GI tract prior to its distribution outside the GI tract and cleavage at a desired site of action.

Methods Used to Define Relative Amounts of Prodrug and Inhibitor in a Dose Unit

Dose units that provide for a desired PK profile, such as a desired concentration-time PK profile and/or a desired concentration-dose PK profile, can be made by combining a prodrug and an inhibitor in a dose unit in relative amounts effective to provide for release of drug that provides for a desired drug PK profile following ingestion by a patient.

Prodrugs can be selected as suitable for use in a dose unit by determining the trypsin-mediated drug release competency of the prodrug. This can be accomplished in vitro, in vivo or ex vivo.

In vitro assays can be conducted by combining a prodrug with trypsin in a reaction mixture. Trypsin can be provided in the reaction mixture in an amount sufficient to catalyze cleavage of the prodrug. Assays are conducted under suitable conditions, and optionally may be under conditions that mimic those found in a GI tract of a subject, e.g., human. "Prodrug conversion" refers to release of drug from prodrug. Prodrug conversion can be assessed by detecting a level of a product of prodrug conversion (e.g., released drug) and/or by detecting a level of prodrug that is maintained in the presence of trypsin. Prodrug conversion can also be assessed by detecting the rate at which a product of prodrug conversion occurs or the rate at which prodrug disappears. An increase in released drug, or a decrease in prodrug, indicate prodrug conversion has occurred. Prodrugs that exhibit an acceptable level of prodrug conversion in the presence of trypsin within an acceptable period of time are suitable for use in a dose unit in combination with a trypsin inhibitor.

In vivo assays can assess the suitability of a prodrug for use in a dose unit by administration of the prodrug to an animal (e.g., a human or non-human animal, e.g., rat, dog, pig, etc.). Such administration can be enteral (e.g., oral administration). Prodrug conversion can be detected by, for example, detecting a product of prodrug conversion (e.g., released drug or a metabolite of released drug) or detecting prodrug in blood or plasma of the animal at a desired time point(s) following administration.

Ex vivo assays, such as a gut loop or inverted gut loop assay, can assess the suitability of a prodrug for use in a dose unit by, for example, administration of the prodrug to a ligated section of the intestine of an animal. Prodrug conversion can be detected by, for example, detecting a product of prodrug conversion (e.g., released drug or a metabolite of released drug) or detecting prodrug in the ligated gut loop of the animal at a desired time point(s) following administration.

Inhibitors are generally selected based on, for example, activity in interacting with trypsin that mediates release of drug from a prodrug with which the inhibitor is to be co-dosed. Such assays can be conducted in the presence of enzyme either with or without prodrug. Inhibitors can also be selected according to properties such as half-life in the GI system, potency, avidity, affinity, molecular size and/or enzyme inhibition profile (e.g., steepness of inhibition curve in an enzyme activity assay, inhibition initiation rate). Inhibitors for use in prodrug-inhibitor combinations can be selected through use of in vitro, in vivo and/or ex vivo assays.

One embodiment is a method for identifying a prodrug and a trypsin inhibitor suitable for formulation in a dose unit wherein the method comprises combining a prodrug (e.g., Compound KC-8), a trypsin inhibitor, and trypsin in a reaction mixture and detecting prodrug conversion. Such a combination is tested for an interaction between the prodrug, inhibitor and enzyme, i.e., tested to determine how the inhibitor will interact with the enzyme that mediates enzymatically-controlled release of the drug from the prodrug. In one embodiment, a decrease in prodrug conversion in the presence of the trypsin inhibitor as compared to prodrug conversion in the absence of the trypsin inhibitor indicates the prodrug and trypsin inhibitor are suitable for formulation in a dose unit. Such a method can be an in vitro assay.

One embodiment is a method for identifying a prodrug and a trypsin inhibitor suitable for formulation in a dose unit wherein the method comprises administering to an animal a prodrug (e.g., Compound KC-8) and a trypsin inhibitor and detecting prodrug conversion. In one embodiment, a decrease in prodrug conversion in the presence of the trypsin inhibitor as compared to prodrug conversion in the absence of the trypsin inhibitor indicates the prodrug and trypsin inhibitor are suitable for formulation in a dose unit. Such a method can be an in vivo assay; for example, the prodrug and trypsin inhibitor can be administered orally. Such a method can also be an ex vivo assay; for example, the prodrug and trypsin inhibitor can be administered orally or to a tissue, such as an intestine, that is at least temporarily exposed. Detection can occur in the blood or plasma or respective tissue. As used herein, tissue refers to the tissue itself and can also refer to contents within the tissue.

One embodiment is a method for identifying a prodrug and a trypsin inhibitor suitable for formulation in a dose unit wherein the method comprises administering a prodrug and a trypsin inhibitor to an animal tissue that has removed from an animal and detecting prodrug conversion. In one embodiment, a decrease in prodrug conversion in the presence of the trypsin inhibitor as compared to prodrug conversion in the absence of the trypsin inhibitor indicates the prodrug and trypsin inhibitor are suitable for formulation in a dose unit.

In vitro assays can be conducted by combining a prodrug, a trypsin inhibitor and trypsin in a reaction mixture. Trypsin can be provided in the reaction mixture in an amount sufficient to catalyze cleavage of the prodrug, and assays conducted under suitable conditions, optionally under conditions that mimic those found in a GI tract of a subject, e.g., human. Prodrug conversion can be assessed by detecting a level of a product of prodrug conversion (e.g., released drug) and/or by detecting a level of prodrug maintained in the presence of trypsin. Prodrug conversion can also be assessed by detecting the rate at which a product of prodrug conversion occurs or the rate at which prodrug disappears. Prodrug conversion that is modified in the presence of inhibitor as compared to a level of prodrug conversion in the absence of inhibitor indicates the inhibitor is suitable for attenuation of prodrug conversion and for use in a dose unit. Reaction mixtures having a fixed amount of prodrug and increasing amounts of inhibitor, or a fixed amount of inhibitor and increasing amounts of prodrug, can be used to identify relative amounts of prodrug and inhibitor which provide for a desired modification of prodrug conversion.

In vivo assays can assess combinations of prodrugs and inhibitors by co-dosing of prodrug and inhibitor to an animal. Such co-dosing can be enteral. "Co-dosing" refers to administration of prodrug and inhibitor as separate doses or a combined dose (i.e., in the same formulation). Prodrug conversion can be detected by, for example, detecting a product of prodrug conversion (e.g., released drug or drug metabolite) or detecting prodrug in blood or plasma of the animal at a desired time point(s) following administration. Combinations of prodrug and inhibitor can be identified that provide for a prodrug conversion level that yields a desired PK profile as compared to, for example, prodrug without inhibitor.

Combinations of relative amounts of prodrug and inhibitor that provide for a desired PK profile can be identified by dosing animals with a fixed amount of prodrug and increasing amounts of inhibitor, or with a fixed amount of inhibitor and increasing amounts of prodrug. One or more PK parameters can then be assessed, e.g., drug Cmax, drug Tmax, and drug exposure. Relative amounts of prodrug and inhibitor that provide for a desired PK profile are identified as amounts of prodrug and inhibitor for use in a dose unit. The PK profile of the prodrug and inhibitor combination can be, for example, characterized by a decreased PK parameter value relative to prodrug without inhibitor. A decrease in the PK parameter value of an inhibitor-to-prodrug combination (e.g., a decrease in drug Cmax, a decrease in 1/drug Tmax (i.e., a delay in drug Tmax) or a decrease in drug exposure) relative to a corresponding PK parameter value following administration of prodrug without inhibitor can be indicative of an inhibitor-to-prodrug combination that can provide a desired PK profile. Assays can be conducted with different relative amounts of inhibitor and prodrug.

In vivo assays can be used to identify combinations of prodrug and inhibitor that provide for dose units that provide for a desired concentration-dose PK profile following ingestion of multiples of the dose unit (e.g., at least 2, at least 3, at least 4 or more). Ex vivo assays can be conducted by direct administration of prodrug and inhibitor into a tissue and/or its contents of an animal, such as the intestine, including by introduction by injection into the lumen of a ligated intestine (e.g., a gut loop, or intestinal loop, assay, or an inverted gut assay). An ex vivo assay can also be conducted by excising a tissue and/or its contents from an animal and introducing prodrug and inhibitor into such tissues and/or contents.

For example, a dose of prodrug that is desired for a single dose unit is selected (e.g., an amount that provides an efficacious plasma drug level). A multiple of single dose units for which a relationship between that multiple and a PK parameter to be tested is then selected. For example, if a concentration-dose PK profile is to be designed for ingestion of 2, 3, 4, 5, 6, 7, 8, 9 or 10 dose units, then the amount of prodrug equivalent to ingestion of that same number of dose units is determined (referred to as the "high dose"). The multiple of dose units can be selected based on the number of ingested pills at which drug Cmax is modified relative to ingestion of the single dose unit. If, for example, the profile is to provide for abuse deterrence, then a multiple of 10 can be selected, for example. A variety of different inhibitors (e.g., from a panel of inhibitors) can be tested using different relative amounts of inhibitor and prodrug. Assays can be used to identify suitable combination(s) of inhibitor and prodrug to obtain a single dose unit that is therapeutically effective, wherein such a combination, when ingested as a multiple of dose units, provides a modified PK parameter compared to ingestion of the same multiple of drug or prodrug alone (wherein a single dose of either drug or prodrug alone releases into blood or plasma the same amount of drug as is released by a single dose unit).

Increasing amounts of inhibitor are then co-dosed to animals with the high dose of prodrug. The dose level of inhibitor that provides a desired drug Cmax following ingestion of the high dose of prodrug is identified and the resultant inhibitor-to-prodrug ratio determined.

Prodrug and inhibitor are then co-dosed in amounts equivalent to the inhibitor-to-prodrug ratio that provided the desired result at the high dose of prodrug. The PK parameter value of interest (e.g., drug Cmax) is then assessed. If a desired PK parameter value results following ingestion of the single dose unit equivalent, then single dose units that provide for a desired concentration-dose PK profile are identified. For example, where a zero dose linear profile is desired, the drug Cmax following ingestion of a single dose unit does not increase significantly following ingestion of a multiple number of the single dose units.

Methods for Manufacturing, Formulating, and Packaging Dose Units

Dose units of the present disclosure can be made using manufacturing methods available in the art and can be of a variety of forms suitable for enteral (including oral, buccal and sublingual) administration, for example as a tablet, capsule, thin film, powder, suspension, solution, syrup, dispersion or emulsion. The dose unit can contain components conventional in pharmaceutical preparations, e.g. one or more carriers, binders, lubricants, excipients (e.g., to impart controlled release characteristics), pH modifiers, flavoring agents (e.g., sweeteners), bulking agents, coloring agents or further active agents. Dose units of the present disclosure can include can include an enteric coating or other component(s) to facilitate protection from stomach acid, where desired.

Dose units can be of any suitable size or shape. The dose unit can be of any shape suitable for enteral administration, e.g., ellipsoid, lenticular, circular, rectangular, cylindrical, and the like.

Dose units provided as dry dose units can have a total weight of from about 1 microgram to about 1 gram, and can be from about 5 micrograms to 1.5 grams, from about 50 micrograms to 1 gram, from about 100 micrograms to 1 gram, from 50 micrograms to 750 milligrams, and may be from about 1 microgram to 2 grams.

Dose units can comprise components in any relative amounts. For example, dose units can be from about 0.1% to 99% by weight of active ingredients (i.e., prodrug and inhibitor) per total weight of dose unit (0.1% to 99% total combined weight of prodrug and inhibitor per total weight of single dose unit). In some embodiments, dose units can be from 10% to 50%, from 20% to 40%, or about 30% by weight of active ingredients per total weight dose unit.

Dose units can be provided in a variety of different forms and optionally provided in a manner suitable for storage. For example, dose units can be disposed within a container suitable for containing a pharmaceutical composition. The container can be, for example, a bottle (e.g., with a closure device, such as a cap), a blister pack (e.g., which can provide for enclosure of one or more dose units per blister), a vial, flexible packaging (e.g., sealed Mylar or plastic bags), an ampule (for single dose units in solution), a dropper, thin film, a tube and the like.

Containers can include a cap (e.g., screw cap) that is removably connected to the container over an opening through which the dose units disposed within the container can be accessed.

Containers can include a seal which can serve as a tamper-evident and/or tamper-resistant element, which seal is disrupted upon access to a dose unit disposed within the container. Such seal elements can be, for example, a frangible element that is broken or otherwise modified upon access to a dose unit disposed within the container. Examples of such frangible seal elements include a seal positioned over a container opening such that access to a dose unit within the container requires disruption of the seal (e.g., by peeling and/or piercing the seal). Examples of frangible seal elements include a frangible ring disposed around a container opening and in connection with a cap such that the ring is broken upon opening of the cap to access the dose units in the container.

Dry and liquid dose units can be placed in a container (e.g., bottle or package, e.g., a flexible bag) of a size and configuration adapted to maintain stability of dose units over a period during which the dose units are dispensed into a prescription. For example, containers can be sized and configured to contain 10, 20, 30, 40, 50, 60, 70, 80, 90, 100 or more single dry or liquid dose units. The containers can be sealed or resealable. The containers can packaged in a carton (e.g., for shipment from a manufacturer to a pharmacy or other dispensary). Such cartons can be boxes, tubes, or of other configuration, and may be made of any material (e.g., cardboard, plastic, and the like). The packaging system and/or containers disposed therein can have one or more affixed labels (e.g., to provide information such as lot number, dose unit type, manufacturer, and the like).

The container can include a moisture barrier and/or light barrier, e.g., to facilitate maintenance of stability of the active ingredients in the dose units contained therein. Where the dose unit is a dry dose unit, the container can include a desiccant pack which is disposed within the container. The container can be adapted to contain a single dose unit or multiples of a dose unit. The container can include a dispensing control mechanism, such as a lock out mechanism that facilitates maintenance of dosing regimen.

The dose units can be provided in solid or semi-solid form, and can be a dry dose unit. "Dry dose unit" refers to a dose unit that is in other than in a completely liquid form. Examples of dry dose units include, for example, tablets, capsules (e.g., solid capsules, capsules containing liquid), thin film, microparticles, granules, powder and the like. Dose units can be provided as liquid dose units, where the dose units can be provided as single or multiple doses of a formulation containing prodrug and inhibitor in liquid form. Single doses of a dry or liquid dose unit can be disposed within a sealed container, and sealed containers optionally provided in a packaging system, e.g., to provide for a prescribed number of doses, to provide for shipment of dose units, and the like.

Dose units can be formulated such that the prodrug and inhibitor are present in the same carrier, e.g., solubilized or suspended within the same matrix. Alternatively, dose units can be composed of two or more portions, where the prodrug and inhibitor can be provided in the same or different portions, and can be provided in adjacent or non-adjacent portions.

Dose units can be provided in a container in which they are disposed, and may be provided as part of a packaging system (optionally with instructions for use). For example, dose units containing different amounts of prodrug can be provided in separate containers, which containers can be disposed with in a larger container (e.g., to facilitate protection of dose units for shipment). For example, one or more dose units as described herein can be provided in separate containers, where dose units of different composition are provided in separate containers, and the separate containers disposed within package for dispensing.

In another example, dose units can be provided in a double-chambered dispenser where a first chamber contains a prodrug formulation and a second chamber contains an inhibitor formulation. The dispenser can be adapted to provide for mixing of a prodrug formulation and an inhibitor formulation prior to ingestion. For example, the two chambers of the dispenser can be separated by a removable wall (e.g., frangible wall) that is broken or removed prior to administration to allow mixing of the formulations of the two chambers. The first and second chambers can terminate into a dispensing outlet, optionally through a common chamber. The formulations can be provided in dry or liquid form, or a combination thereof. For example, the formulation in the first chamber can be liquid and the formulation in the second chamber can be dry, both can be dry, or both can be liquid.

Dose units that provide for controlled release of prodrug, of inhibitor, or of both prodrug and inhibitor are contemplated by the present disclosure, where "controlled release" refers to release of one or both of prodrug and inhibitor from the dose unit over a selected period of time and/or in a pre-selected manner.

Methods of Use of Dose Units

Dose units are advantageous because they find use in methods to reduce side effects and/or improve tolerability of drugs to patients in need thereof by, for example, limiting a PK parameter as disclosed herein. The present disclosure thus provides methods to reduce side effects by administering a dose unit of the present disclosure to a patient in need so as to provide for a reduction of side effects as compared to those associated with administration of drug and/or as compared to administration of prodrug without inhibitor. The present disclosure also provides methods to improve tolerability of drugs by administering a dose unit of the present disclosure to a patient in need so as to provide for improvement in tolerability as compared to administration of drug and/or as compared to administration of prodrug without inhibitor.

Dose units find use in methods for increasing patient compliance of a patient with a therapy prescribed by a clinician, where such methods involve directing administration of a dose unit described herein to a patient in need of therapy so as to provide for increased patient compliance as compared to a therapy involving administration of drug and/or as compared to administrations of prodrug without inhibitor. Such methods can help increase the likelihood that a clinician-specified therapy occurs as prescribed.

Dose units can provide for enhanced patient compliance and clinician control. For example, by limiting a PK parameter (e.g., such as drug Cmax or drug exposure) when multiples (e.g., two or more, three or more, or four or more) dose units are ingested, a patient requiring a higher dose of drug must seek the assistance of a clinician. The dose units can provide for control of the degree to which a patient can readily "self-medicate", and further can provide for the patient to adjust dose to a dose within a permissible range. Dose units can provide for reduced side effects, by for example, providing for delivery of drug at an efficacious dose but with a modified PK profile over a period of treatment, e.g., as defined by a decreased PK parameter (e.g., decreased drug Cmax, decreased drug exposure).

Dose units find use in methods to reduce the risk of unintended overdose of drug that can follow ingestion of multiple doses taken at the same time or over a short period of time. Such methods of the present disclosure can provide for reduction of risk of unintended overdose as compared to risk of unintended overdose of drug and/or as compared to risk of unintended overdose of prodrug without inhibitor. Such methods involve directing administration of a dosage described herein to a patient in need of drug released by conversion of the prodrug. Such methods can help avoid unintended overdosing due to intentional or unintentional misuse of the dose unit.

The present disclosure provides methods to reduce misuse and abuse of a drug, as well as to reduce risk of overdose, that can accompany ingestion of multiples of doses of a drug, e.g., ingested at the same time. Such methods generally involve combining in a dose unit a prodrug and a trypsin inhibitor that mediates release of drug from the prodrug, where the inhibitor is present in the dose unit in an amount effective to attenuate release of drug from the prodrug, e.g., following ingestion of multiples of dose units by a patient. Such methods provide for a modified concentration-dose PK profile while providing therapeutically effective levels from a single dose unit, as directed by the prescribing clinician. Such methods can provide for, for example, reduction of risks that can accompany misuse and/or abuse of a prodrug, particularly where conversion of the prodrug provides for release of a narcotic or other drug of abuse (e.g., opioid). For example, when the prodrug provides for release of a drug of abuse, dose units can provide for reduction of reward that can follow ingestion of multiples of dose units of a drug of abuse.

Dose units can provide clinicians with enhanced flexibility in prescribing drug. For example, a clinician can prescribe a dosage regimen involving different dose strengths, which can involve two or more different dose units of prodrug and inhibitor having different relative amounts of prodrug, different amounts of inhibitor, or different amounts of both prodrug and inhibitor. Such different strength dose units can provide for delivery of drug according to different PK parameters (e.g., drug exposure, drug Cmax, and the like as described herein). For example, a first dose unit can provide for delivery of a first dose of drug following ingestion, and a second dose unit can provide for delivery of a second dose of drug following ingestion. The first and second prodrug doses of the dose units can be different strengths, e.g., the second dose can be greater than the first dose. A clinician can thus prescribe a collection of two or more, or three or more dose units of different strengths, which can be accompanied by instructions to facilitate a degree of self-medication, e.g., to increase delivery of an opioid drug according to a patient's needs to treat pain.

Thwarting Tampering by Trypsin Mediated Release of Oxycodone from Prodrug

The disclosure provides for a composition comprising Compound KC-8 and a trypsin inhibitor that reduces drug abuse potential. A trypsin inhibitor can thwart the ability of a user to apply trypsin to effect the release of oxycodone from the ketone-modified oxycodone prodrug, Compound KC-8, in vitro. For example, if an abuser attempts to incubate trypsin with a composition of the embodiments that includes Compound KC-8 and a trypsin inhibitor, the trypsin inhibitor can reduce the action of the added trypsin, thereby thwarting attempts to release oxycodone for purposes of abuse.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

Synthesis of Ketone-modified Opioid Prodrugs

Example 1

Synthesis of oxycodone 6-(N-methyl-N-(2-amino) ethylcarbamate (Compound KC-19)

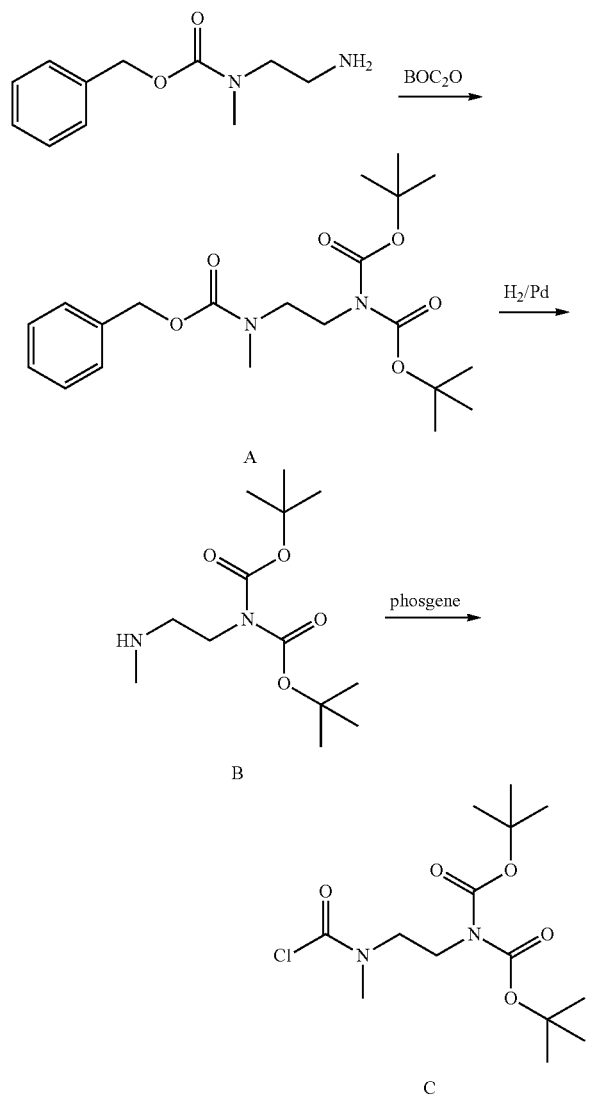

Preparation of Compound A 2-(Aminoethyl)-methyl-carbamic acid benzyl ester (2.0 g, 9.6 mmol) was dissolved in dichloroethene (DCE) (20 mL) at room temperature. Triethyl amine ($NEt_3$) (1.40 mL, 11.5 mmol) was added, followed by di-tert-butyl dicarbonate ($BOC_2O$) (10.5 g, 48 mmol) and dimethylaminopyridine (DMAP) (120 mg). The reaction mixture was stirred at room temperature under nitrogen ($N_2$) for 2 h and then heated at 60° C. for 16 h. The reaction mixture was then concentrated. The residue was purified by silica gel chromatography, using 4/1 hexanes/EtOAc, to give Compound A in 86% yield (3.4 g, 8.3 mmol). MS: (m/z) calc: 408.2, observed (M+Na$^+$) 431.9.

Preparation of Compound B

Compound A (1.3 g, 3.18 mmol) was dissolved in methanol/EtOAc (10 mL/3 mL respectively). The mixture was degassed and saturated with $N_2$. Palladium on carbon (Pd/C) (330 mg, 5% on carbon) was added. The mixture was shaken in a Parr hydrogenator flask (50 psi $H_2$) for 4 h. The mixture was then filtered through a celite pad, and the filtrate was concentrated to give Compound B (1.08 g, yield exceeded quantitative). Compound B was used without further purification.

Preparation of Compound C

Compound B (500 mg, 1.82 mmol) and $NEt_3$ (0.4 mL, 2.74 mmol) were mixed together in dichloromethane (4 mL). The mixture was added to a pre-chilled 0° C. solution of phosgene (5.5 mL, 0.5 M in toluene). The reaction mixture was stirred at 0° C. for 1 h, followed by dilution with ether (20 mL) and filtration through filter paper. The filtrate was concentrated and passed through a short silica gel column (10 cm×3 cm), and eluted with 3/1 hexanes/EtOAc. The fractions were concentrated to give N,N-Bis(tert-butyl)N'-2-(chlorocarbonyl (methyl)amino)ethylcarbamate (Compound C) as a colorless solid in quantitative yield (615 mg, 1.82 mmol). MS: (m/z) calc: 336.1, observed (M+Na$^+$) 359.8.

Synthesis of Oxycodone 6-(N-methyl-N-(2-amino) ethylcarbamate (Compound KC-19)

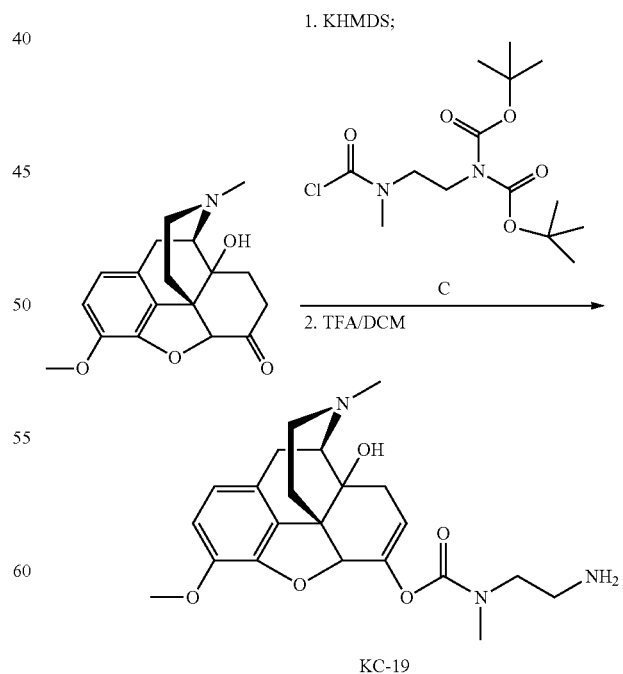

Oxycodone free base (6.5 g, 20.6 mmol) was dissolved in dry, degassed tetrahydrofuran (120 mL), and the mixture was cooled to −10° C. using a dry ice/acetone bath. Potassium bis(trimethylsilyl)amide (KHMDS) (103.0 mL, 51.6 mmol, 0.5 M in toluene) was added via cannula. The mixture was stirred under N₂ at below −5° C. for 30 min. N,N-Bis(tert-butyl)N'-2-(chlorocarbonyl(methyl)amino)ethylcarbamate (8.0 g, 23.7 mmol), (Compound C) in THF (30 mL) was then added via cannula over 15 min. The mixture was stirred at −5° C. for 30 min. Another portion of carbamoyl chloride (4.0 g, 11.9 mmol) in THF (10 mL) was added. The reaction was stirred at room temperature for 2 h. Sodium bicarbonate (10 mL, sat. aq.) was added. The mixture was concentrated in vacuo to half of its initial volume. EtOAc (50 mL) was added, and layers were separated. The organic phase was further washed with water (3×20 mL) and brine (40 mL), and then was concentrated. The residue was purified by silica gel chromatography, using DCM/MeOH (gradient 100/1 to 100/15) to afford a white foam in 55% yield (7.0 g, 13.4 mmol). This material was dissolved in a 1:1 mixture of DCM/trifluoroacetic acid (TFA) (20 mL/20 mL) at room temperature and stirred for 1 h. The solution was then concentrated in vacuo to afford a TFA salt of oxycodone 6-(N-methyl-N-(2-amino)ethylcarbamate (Compound KC-19) as a thick oil (7.3 g, 11.4 mmol, 99% purity). MS: (m/z) calc: 415.2, observed (M+H⁺) 416.5.

Example 2

Synthesis of N-1-[2-(oxycodone-6-enol-carbonyl-methyl-amino)-ethylamine]-arginine-malonic acid (Compound KC-3) [also named: N-{(S)-4-guanidino-1-[2-(methyl-[(5R,9R,13S,14S)-4,5a-epoxy-6,7-didehydro-14-hydroxy-3-methoxy-[7-methylmorphinan-6-oxy]carbonyl-amino)-ethylcarbamoyl]-butyl}-malonic acid]

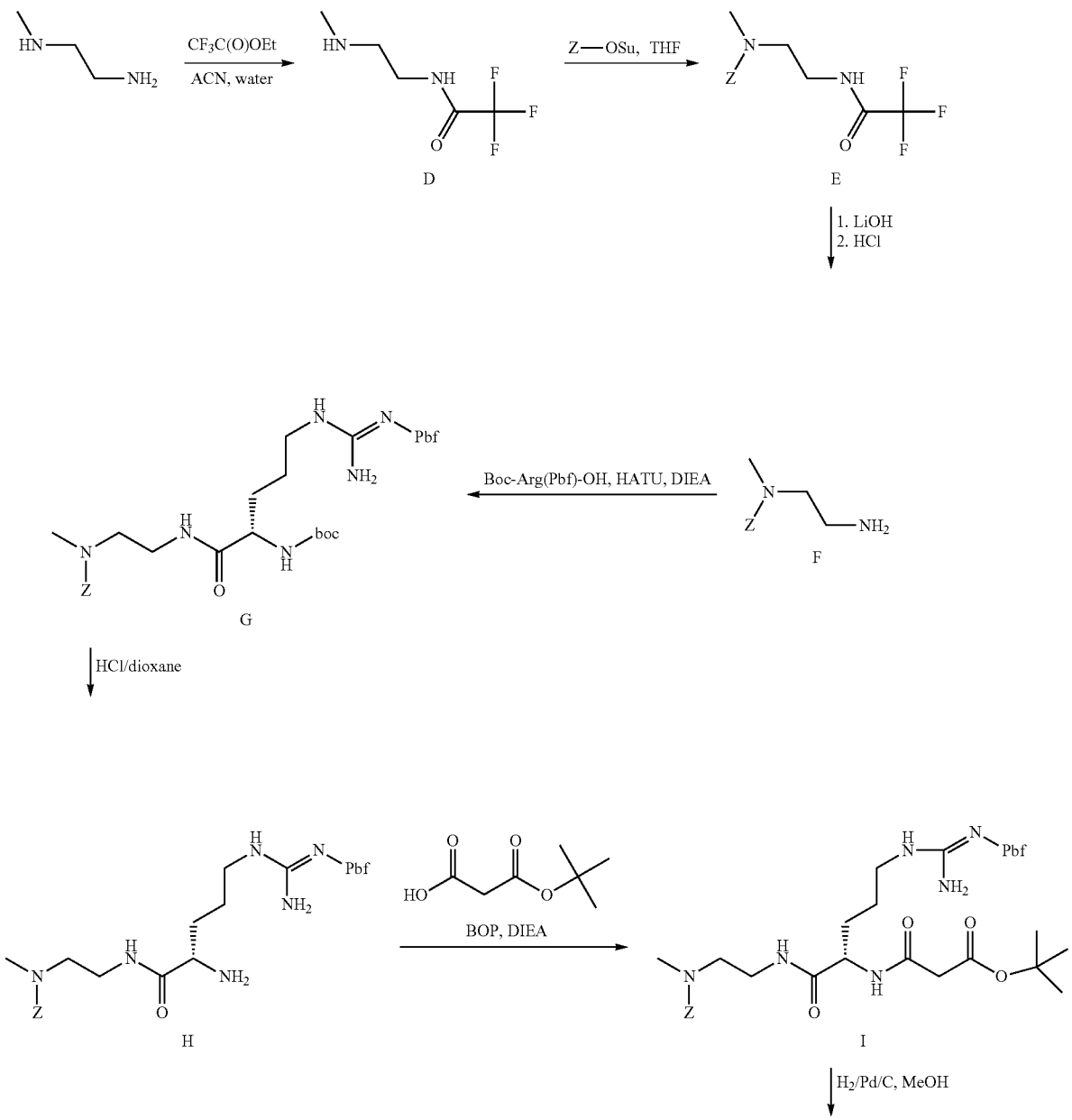

-continued

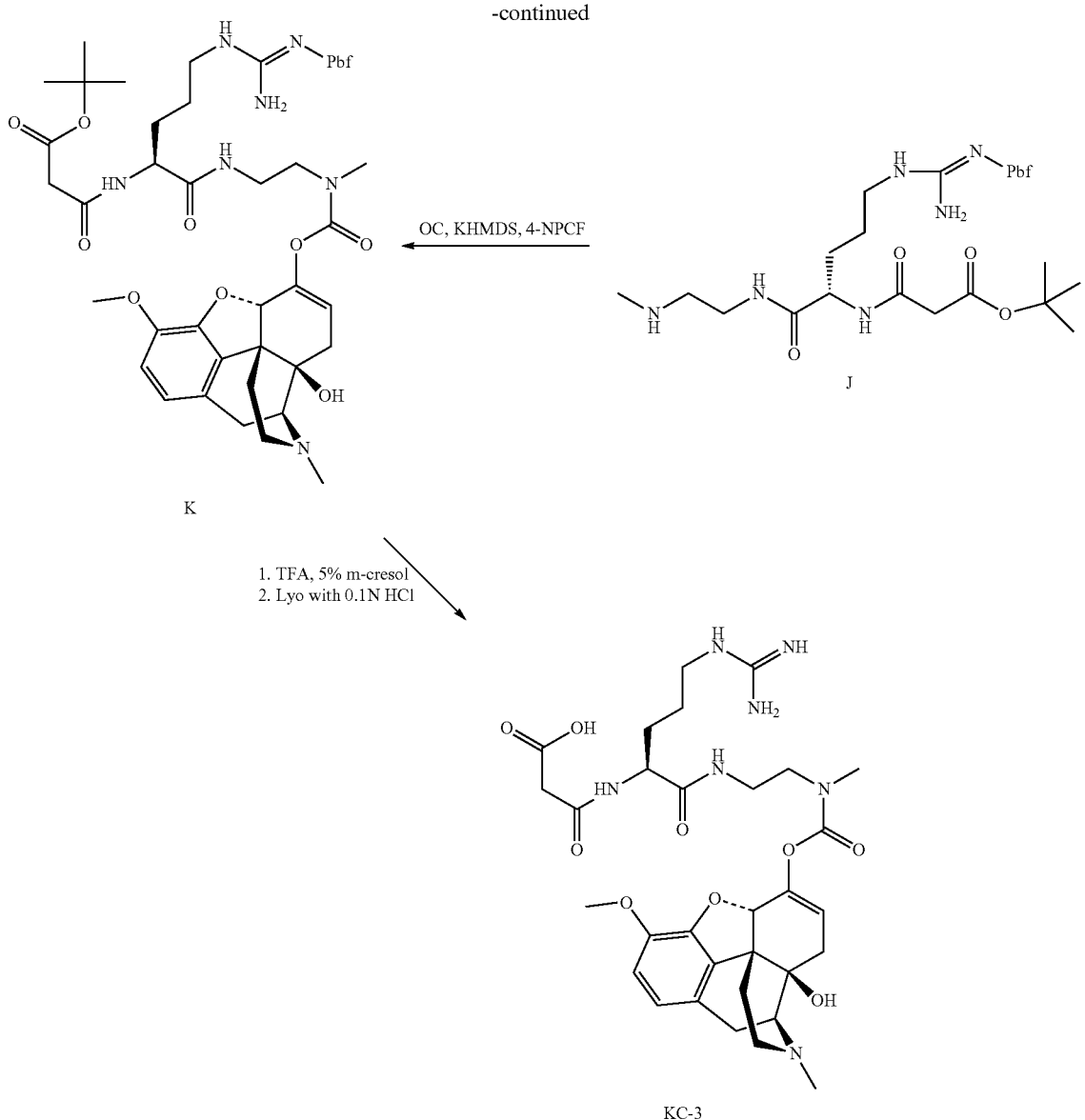

Preparation of Compound D

A solution of N-methylethylenediamine (27.0 g, 364 mmol) and ethyl trifluoroacetate (96.6 mL, 812 mmol) in a mixture of ACN (350 mL) and water (7.8 mL, 436 mmol) was refluxed with stifling overnight. Solvents were evaporated in vacuo. The residue was re-evaporated with i-PrOH (3×100 mL), followed by heat-cool crystallization from DCM (500 mL). Formed crystals were filtered, washed with DCM and dried in vacuo to provide Compound D (88.3 g, 85%) as white solid powder.

Preparation of Compound E

A solution of Compound D (88.2 g, 311 mmol) and DIEA (54.1 mL, 311 mmol) in THF (350 mL) was cooled in an ice bath, followed by the addition of a solution of N-(benzyloxycarbonyl)succinimide (76.6 g, 307 mmol) in THF (150 mL) dropwise over the period of 20 min. The temperature of the reaction mixture was raised to ambient temperature and stirring was continued for an additional 30 min. Solvents were then evaporated and the resulting residue was dissolved in EtOAc (600 mL). The organic layer was extracted with 5% aq. NaHCO$_3$ (2×150 mL) and brine (150 mL). The organic layer was evaporated to provide Compound E as yellowish oil. LC-MS [M+H] 305.1 ($C_{13}H_{15}F_3N_2O_3$+H, calc: 305.3). Compound E was used directly in the next reaction without purification as a MeOH solution.

Preparation of Compound F

To a solution of Compound E (~311 mmol) in MeOH (1.2 L) was added a solution of LiOH (14.9 g, 622 mmol) in water (120 mL). The reaction mixture was stirred at ambient temperature for 3 h. Solvents were evaporated to 75% of the initial volume followed by dilution with water (400 mL). The solution was extracted with EtOAc (2×300 mL). The organic layer was washed with brine (200 mL), dried over MgSO$_4$ and evaporated in vacuo. The residue was dissolved in ether (300 mL) and treated with 2 N HCl/ether (200 mL). Formed precipitate was filtrated, washed with ether and dried in vacuo to provide the hydrochloric salt of Compound F (67.8 g, 89%) as a white solid. LC-MS [M+H] 209.0 ($C_{11}H_{16}N_2O_2$+H, calc: 209.3). Compound F was used directly in the next reaction without purification as a DMF solution.

Preparation of Compound G

A solution of Boc-Arg(Pbf)-OH (16.0 g, ~30.4 mmol), Compound F hydrochloride (8.2 g, 33.4 mmol), and DIEA (16.9 mL, 97.2 mmol) in DMF (150 mL) was cooled in an ice bath followed by the addition of a solution of HATU (13.8 g, 36.4 mmol) dropwise over 20 min. The temperature of the reaction mixture was raised to ambient temperature, and stirring was continued for an additional 1 h. The reaction mixture was diluted with EtOAc (1 L) and extracted with water (3×200 mL) and brine (200 mL). The organic layer was dried over MgSO$_4$ and evaporated to provide Compound G (24.4 g, yield exceeded quantitative) as a yellowish oil. LC-MS [M+H] 717.4 ($C_{35}H_{52}N_6O_8S$+H, calc: 717.9). Compound G was used directly in the next reaction without purification as a dioxane solution.

Preparation of Compound H

Compound G (24.4 g, ~30.4 mmol) was dissolved in dioxane (150 mL) and treated with 4 N HCl/dioxane (150 mL, 600 mmol) at ambient temperature for 1 h. The solvent was then evaporated. The residue was suspended in i-PrOH (100 mL), and the mixture was evaporated (procedure was repeated twice). The residue was then dried in vacuo to provide Compound H (21.1 g, yield exceeded quantitative) as a yellowish solid. LC-MS [M+H] 617.5 ($C_{30}H_{44}N_6O_6S$+H, calc: 617.8). Compound H was used directly in the next reaction without purification as a DMF solution.

Preparation of Compound I

A solution of Compound H (21.1 g, ~30.4 mmol), mono-tert-butyl malonate (5.9 mL, 36.7 mmol), BOP (16.2 g, 36.7 mmol) and DIEA (14.9 mL, 83.5 mmol) in DMF (100 mL) was maintained at ambient temperature for 1 h. The reaction mixture was diluted with EtOAc (1 L) and extracted with water (500 mL), 5% aq. NaHCO$_3$ (500 mL), water (3×500 mL) and brine (500 mL). The organic layer was dried over MgSO$_4$, filtered, and then evaporated to provide Compound I (24.5 g, 97%) as a yellowish amorphous solid. LC-MS [M+H] 759.6 ($C_{37}H_{54}N_6O_9S$+H, calc: 759.9). Compound I was used without further purification.

Preparation of Compound J

Compound I (12.3 g, 16.7 mmol) was dissolved in methanol (100 mL) followed by the addition of a Pd/C (5% wt, 2.0 g) suspension in water (2 mL). The reaction mixture was subjected to hydrogenation (Parr apparatus, 70 psi H$_2$) at ambient temperature for 1 h. The catalyst was then filtered and washed with methanol. The filtrate was evaporated in vacuo to provide Compound J (10.0 g, 99%) as a colorless amorphous solid. LC-MS [M+H] 625.5 ($C_{29}H_{48}N_6O_7S$+H, calc: 625.8). Compound J was used without further purification.

Preparation of Oxycodone Free Base

Oxycodone hydrochloride (10.0 g, 28.5 mmol) was dissolved in chloroform (150 mL) and washed with 5% aq. NaHCO$_3$ (50 mL). The organic layer was dried over MgSO$_4$ and evaporated. The residue was dried in vacuo overnight to provide oxycodone free base (8.3 g, 93%) as a white solid.

Preparation of Compound K

A solution of oxycodone free base (6.6 g, 21.0 mmol) in THF (400 mL) was cooled to −20° C., followed by addition of a 0.5 M solution of KHMDS in toluene (46.3 mL, 23.1 mmol). The obtained solution was then added to a solution of 4-nitro-phenyl chloroformate (4.3 g, 21.0 mmol) in THF (100 mL) dropwise over the period of 20 min at −20° C. The reaction was maintained at −20° C. for an additional 1 h, followed by addition of a solution of Compound J (10.0 g, 16.1 mmol) in THF (200 mL) at −20° C. The reaction mixture was allowed to warm to ambient temperature and stirred overnight. Solvents were evaporated in vacuo. The resulting residue was dissolved in EtOAc (20 mL) and precipitated with ether (1 L). The formed precipitate was filtrated, washed with ether and dried in vacuo to provide Compound K (13.6 g, 87%) as an off-white solid. LC-MS [M+H] 966.9 ($C_{48}H_{67}N_7O_{12}S$+H, calc: 966.2).

Synthesis of N-1-[2-(oxycodone-6-enol-carbonyl-methyl-amino)-ethylamine]-arginine-malonic acid (Compound KC-3)

Compound K (13.6 g, 14.1 mmol) was dissolved in a mixture of 5% m-cresol/TFA (100 mL). The reaction mixture was maintained at ambient temperature for 1 h, followed by dilution with ethyl ether (1 L). The formed precipitate was filtered, washed with ether and hexane, and dried in vacuo to provide a TFA salt of Compound KC-3 (11.4 g, 81%) as an off-white solid. LC-MS [M+H] 658.6 ($C_{31}H_{43}N_7O_9$+H, calc: 658.7).

The TFA salt of crude Compound KC-3 (11.4 g, 11.4 mmol) was dissolved in water (50 mL). The obtained solution was subjected to HPLC purification. [Nanosyn-Pack YMC-GEL-ODS A (100-10) C-18 column (75×500 mm); flow rate: 250 mL/min; injection volume 50 mL; mobile phase A: 100% water, 0.1% TFA; mobile phase B: 100% ACN, 0.1% TFA; isocratic elution at 0% B in 4 min, gradient elution from 0% to 10% B in 20 min, isocratic elution at 10% B in 30 min, gradient elution from 10% B to 30% B in 41 min; detection at 254 nm]. Fractions containing Compound KC-3 were combined and concentrated in vacuo. The TFA counterion of the latter was replaced with an HCl counterion via lyophilization using 0.1N HCl to provide a HCl salt of Compound KC-3 (4.2 g, 41% yield) as a white solid. LC-MS [M+H] 658.6 ($C_{31}H_{43}N_7O_9$+H, calc: 658.7).

Example 3

Synthesis of N-1-[3-(oxycodone-6-enol-carbonyl-methyl-amino)-2,2-dimethyl-propylamine] (Compound KC-22) and N-1-[3-(oxycodone-6-enol-carbonyl-methyl-amino)-2,2-dimethyl-propylamine]-arginine-glycine-malonic acid (Compound KC-8)

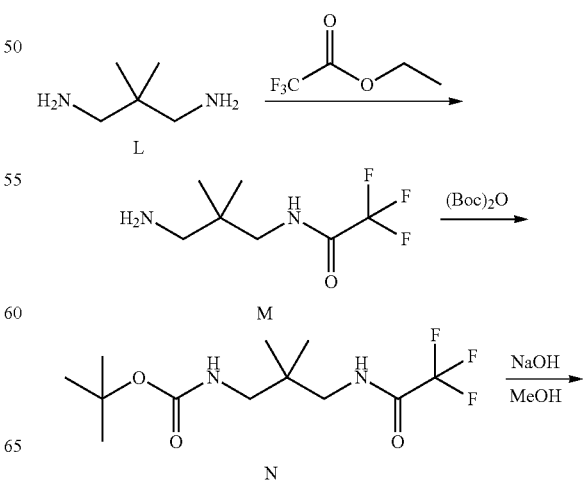

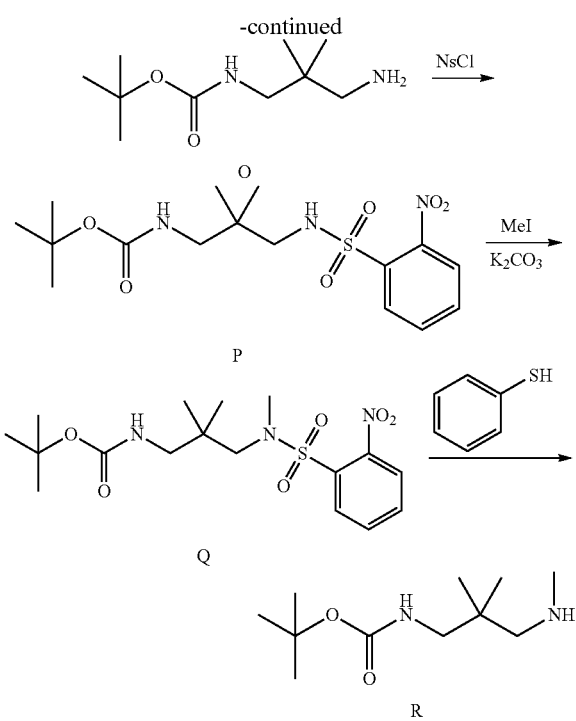

Preparation of Compound M

A solution of 2,2-dimethyl-1,3-diamino propane (Compound L) (48.0 g, 470.6 mmol) in THF (1.0 L) was cooled in an ice bath. Ethyl trifluoroacetate (56 mL, 471 mmol) was added over 30 min via syringe. The mixture was allowed to warm up to ambient temperature, and stifling was continued for 14 h. The mixture was then concentrated in vacuo to half of its original volume to give crude Compound M as a THF solution, which was used without further purification in the next reaction. LC-MS [M+H] 199.6 ($C_7H_{13}F_3N_2O$+H, calc: 199.1).

Preparation of Compound N

To a crude solution of Compound M (from previous step) in THF (500 mL) and chilled in an ice bath was added (Boc)$_2$O in small portions over 15 min. The mixture was stirred at ambient temperature for 15 h. The reaction was then concentrated in vacuo to give intermediate Compound N in 84% yield (over two steps) (120.0 g, 402.4 mmol) as a sticky oil. LC-MS [M+H] 299.2 ($C_{12}H_{21}F_3N_2O_3$+H, calc: 299.2). Compound N was used directly in the next reaction without further purification.

Preparation of Compound O

Compound N (120 g, 403 mmol) was dissolved in CH$_3$OH (500 mL) and stirred at ambient temperature. NaOH (100 mL, 10 N aq.) was added dropwise. The mixture was then stirred in a pre-heated oil bath at 50° C. for 3 h. The mixture was cooled to ambient temperature and diluted with water (500 mL). Solvents were then removed in vacuo. The residue was extracted with CHCl$_3$ (3×100 mL). The combined CHCl$_3$ solution was dried over Na$_2$SO$_4$, filtered and concentrated in vacuo to afford crude Compound O in 95% yield (77.0 g, 381 mmol). LC-MS [M+H] 203.8 ($C_{10}H_{22}N_2O_2$+H, calc: 203.2). Compound O was used directly in the next reaction without further purification.

Preparation of Compound P

Compound O (97.0 g, 480 mmol) was dissolved in CH$_2$Cl$_2$ (750 mL). To this was added K$_2$CO$_3$ (75.0 g, 542.6 mmol) in one portion, followed by portion wise addition of 2-nosyl chloride (108.0 g, 487.3 mmol). The reaction mixture was stirred at ambient temperature for 15 h. Water (200 mL) was then added, and the layers were separated. The aqueous layer was again extracted with CH$_2$Cl$_2$. The combined CH$_2$Cl$_2$ solution was dried over Na$_2$SO$_4$, filtered and concentrated in vacuo. The residue was purified by silica gel chromatography using 3/1 Hexanes/EtOAc to give intermediate Compound P in 83% yield (155.0 g, 400.5 mmol) as a white solid. LC-MS [M+H] 388.8 ($C_{16}H_{25}N_3O_6S$+H, calc: 388.1).

Preparation of Compound R

Compound P (155.0 g, 400.5 mmol) was dissolved in DMF (500 mL) at ambient temperature. K$_2$CO$_3$ (83.0 g, 600 mmol) was added in one portion. The mixture was then cooled in an ice water bath. MeI (37.0 mL, 593 mmol) was added in small portions via syringe over 10 min. The mixture was then warmed up to ambient temperature, and stifling was continued at this temperature for another 2 h. The mixture was concentrated in vacuo until ~50 mL remained. The remaining mixture containing intermediate Compound Q was cooled in an ice water bath. While stirring, thiophenol (100 mL, 978 mmol) was added via a syringe. The resulted mixture was stirred at ambient temperature for 6 h. Water (500 mL) was added. The mixture was extracted with EtOAc (100 mL, then 2×500 mL). The combined EtOAc extracts were extracted with 2N HCl (400 mL, then 2×200 mL). The HCl extracts were pooled and washed with DCM (500 mL). The acidic solution was then chilled in an ice water bath and basified by adding 10 N NaOH until pH ~13. CHCl$_3$ (400 mL, then 2×200 mL) was then used to extract the aqueous solution. The combined CHCl$_3$ solution was dried over Na$_2$SO$_4$ and filtered. Evaporation of solvents in vacuo afforded Compound R in 67% yield (58.0 g, 268.5 mmol) as a slightly yellowish oil. LC-MS [M+H] 217.6 ($C_{11}H_{24}N_2O_2$+H, calc: 217.2).

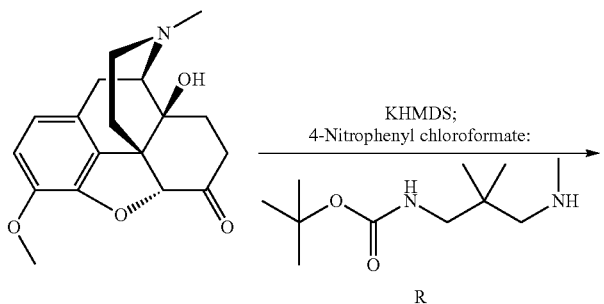

-continued
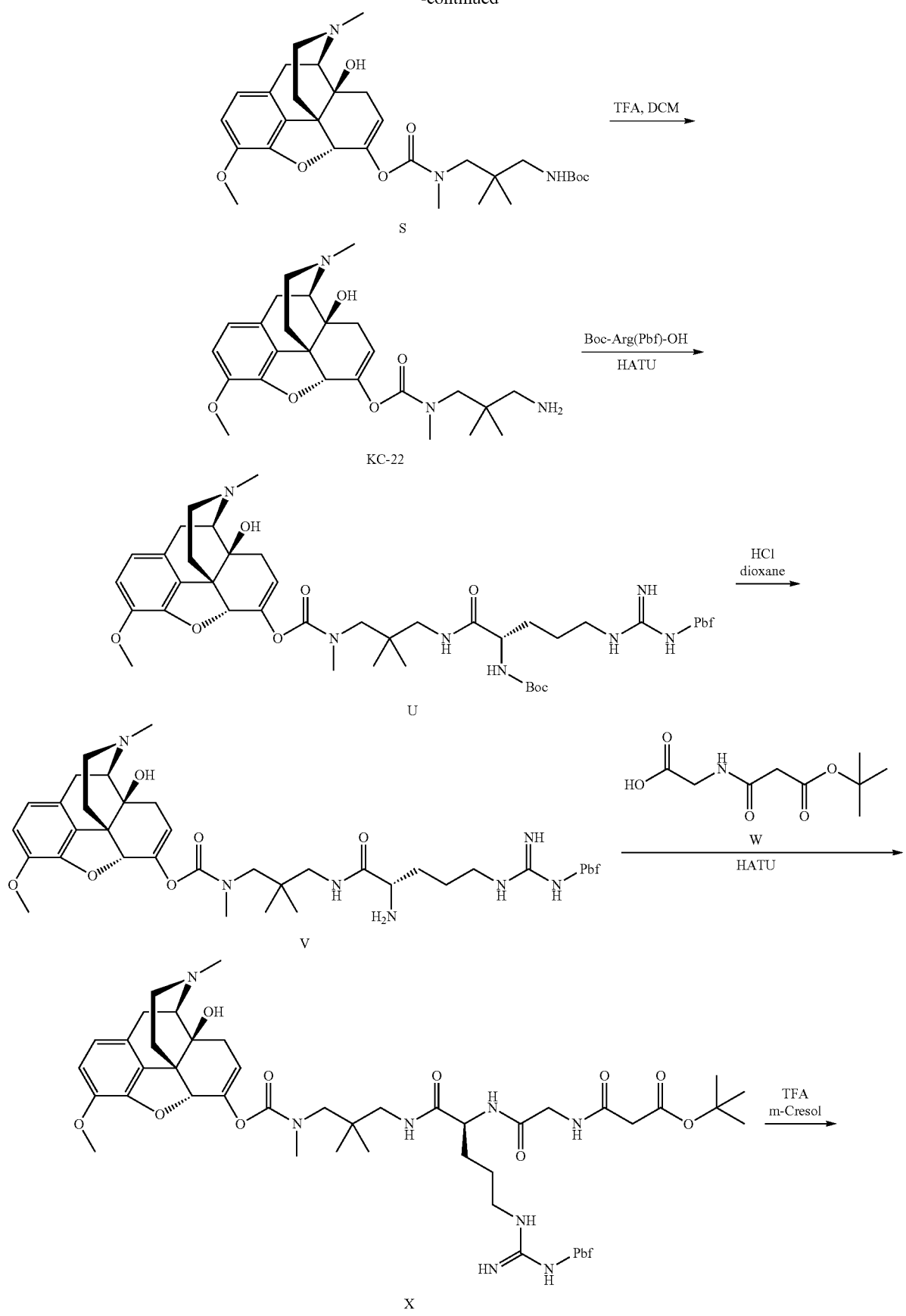

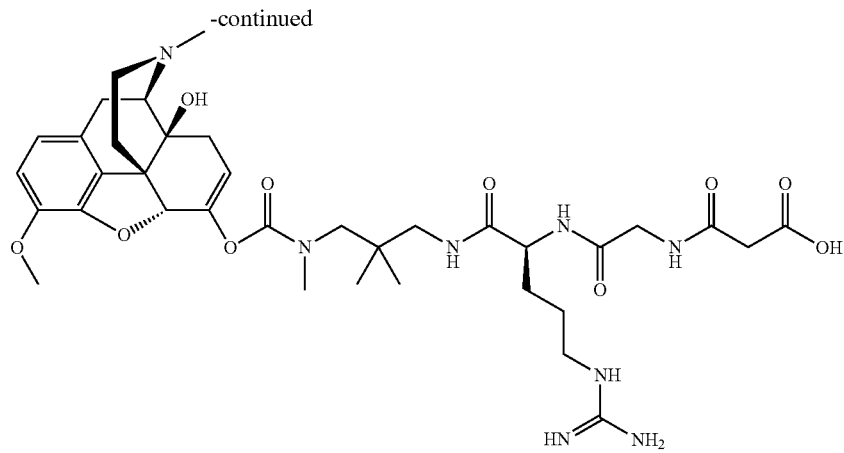

KC-8

Preparation of Compound S

Oxycodone free base (10.0 g, 31.75 mmol) was dissolved in dry THF (150 mL) and the mixture was cooled to −70° C. using a dry ice/acetone bath. KHMDS (64.0 mL, 128.0 mmol, 0.5 M in toluene) was added via syringe over 15 min. The mixture was stirred under $N_2$ for an additional 30 min (bath temperature −70° C.). In a separate flask was added 4-nitrophenyl chloroformate (6.4 g, 31.75 mmol) and THF (10 mL). This mixture was also chilled to −70° C. using a dry ice/acetone bath. The mixture in the first flask (containing deprotonated oxycodone) was then transferred via cannula to the second flask (containing 4-nitrophenyl chloroformate). The transfer occurred over ~30 min, with the temperature of both flasks being maintained at −70° C. during the course of the transfer. The resulted reaction mixture was further stirred at −70° C. for 30 min. A solution of Compound R (6.9 g, 31.94 mmol) in THF (15 mL) was then added via syringe. The mixture was allowed to stir at −70° C. for 30 min, and then concentrated in vacuo to afford a gel like residue (~90% solvent removal). The residue was let stand at ambient temperature for 15 h. It was then taken into EtOAc (200 mL) and washed with sat. aq. $NaHCO_3$ (5×50 mL), water (3×40 mL) and brine (50 mL). The residue from the concentrated EtOAc layer was then purified by silica gel chromatography, using 10/1 $CH_3Cl$/MeOH to give Compound S in 62% yield (11.0 g, 19.7 mmol). LC-MS [M+H] 559.1 ($C_{30}H_{43}N_3O_7$+H, calc: 558.3).

Preparation of N-1-[3-(oxycodone-6-enol-carbonyl-methyl-amino)-2,2-dimethyl-propylamine] (Compound KC-22)

A solution of Compound S (11.0 g, 19.7 mmol) was treated with a mixture of TFA and DCM (30 mL/30 mL) for 2 h at ambient temperature. Solvents were then removed in vacuo until a volume of ~5 mL remained. $Et_2O$ (250 mL) was added to precipitate out the product. The resulting precipitate was filtered, washed with $Et_2O$ (50 mL) and dried to afford crude Compound KC-22 in 97% yield (11.0 g, 19.2 mmol, 90% purity) as a white solid. LC-MS [M+H] 458.9 ($C_{25}H_{35}N_3O_5$+H, calc: 458.3). Compound KC-22 was used directly in the next reaction without further purification.

Preparation of Compound U

A solution of Boc-Arg(Pbf)-OH (9.4 g, 17.8 mmol), Compound KC-22 (11.0 g, 19.7 mmol, 90% pure) and $NEt_3$ (10.0 mL, 71.7 mmol) in DMF (80 mL) was cooled in an ice bath, followed by the addition of HATU (6.8 g, 17.9 mmol) in portions over 10 min. The ice bath was then removed, and the reaction mixture was stirred at ambient temperature for an additional 1 h. The mixture was diluted with EtOAc (150 mL) and extracted with water (3×50 mL) and brine (50 mL). The organic layer was dried over $Na_2SO_4$ and filtered; removal of solvents in vacuo provided crude Compound U. Compound U was purified by flash chromatography using $CH_2Cl_2$ and MeOH to afford Compound U in 79% yield (13.7 g, 14.2 mmol) as a foamy solid. LC-MS [M+H] 967.5 ($C_{49}H_{71}N_7O_{11}S$+H, calc: 966.5).

Preparation of Compound V

A solution of Compound U (13.7 g, 14.2 mmol) was treated with HCl (4.0M solution in 1,4-dioxane, 40 mL) at ambient temperature for 90 min. Solvents were removed in vacuo, and the residue was treated with $Et_2O$ (100 mL). The resulting precipitate was filtered off, washed with $Et_2O$ (2×25 mL), and dried to afford crude Compound V in 91% yield (12.1 g, 12.9 mmol) as a white solid. LC-MS [M+H] 867.8 ($C_{44}H_{63}N_7O_9S$+H, calc: 866.4). Compound V was used directly in the next reaction without further purification.

Preparation of Compound X

To a solution of Compound V (73.3 g, 78.14 mmol, as HCl salt), N-carboxymethylmalonic acid tert-butyl ester (Compound W) (17.0 g, 78.34 mmol), and $NEt_3$ (33.0 mL, 236.7 mmol) in DMF (500 mL) at 0° C. was added HATU (30.6 g, 80.47 mmol) in portions over 10 min. The reaction mixture was stirred at ambient temperature for 1 h. Water (500 mL) was added and the mixture was extracted with EtOAc (750 mL). The EtOAc extracts were washed with water (2×250 mL), $NaHCO_3$ (2×200 mL) and brine (250 mL). The organic layer was dried over $Na_2SO_4$ and filtered. The solution was concentrated, and the residue was purified by a silica gel column, using gradient 1-10% MeOH in $CH_2Cl_2$, to provide Compound X in 43% yield (36.0 g, 33.8 mmol) as a white solid. LC-MS [M+H] 1067.2 ($C_{53}H_{76}N_8O_{13}S$+H, calc: 1065.5).

Preparation of N-1-[3-(oxycodone-6-enol-carbonyl-methyl-amino)-2,2-dimethyl-propylamine]-arginine-glycine-malonic acid (Compound KC-8)

Compound X (36.0 g, 33.8 mmol) was treated with a mixture of TFA (60 mL) and m-cresol (2.0 mL) at ambient temperature. The reaction progress was monitored by LC/MS. After 4 h, the mixture was concentrated in vacuo to remove most of the volatiles (~90% solvent removed). The residue was treated with ethyl ether (1 L), and a white precipitate was formed. The clear supernatant was removed and the precipitate was washed with ethyl ether (1 L). The solid was then concentrated and subjected to HPLC purification. [Nanosyn-Pack Microsorb (100-10) C-18 column (50×300 mm); flow rate: 100 mL/min; injection volume 15 mL; mobile phase A: 100% water, 0.1% TFA; mobile phase B: 100% ACN, 0.1% TFA; gradient elution from 0% to 20% B in 30 min, isocratic elution at 20% B in 30 min, gradient elution from 20% B to 45% B in 35 min; detection at 254 nm]. Fractions containing the desired compound were combined and concentrated in vacuo. The residue was dissolved in ACN (60 mL) and 0.1 N HCl (200 mL), and lyophilized to provide Compound KC-8 in 69.6% yield (19.5 g, 23.5 mmol, 99.4% purity) as a white foam. LC-MS [M+H] 758.5 ($C_{36}H_{52}N_8O_{10}$+H, calc: 757.4).

Biological Data

Example 4

Pharmacokinetics of Compound KC-8 Following PO Administration to Rats

This Example demonstrates the release of oxycodone into plasma when Compound KC-8 is administered orally (PO) to rats.

Saline solutions of Compound KC-8 (which can be prepared as described in the examples herein) were dosed as indicated in Table 1 via oral gavage into jugular vein-cannulated male Sprague Dawley rats (4 per group) that had been fasted for 16-18 h prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice, and then stored in a −80° C. freezer until analysis by HPLC/MS.

Figure 4:
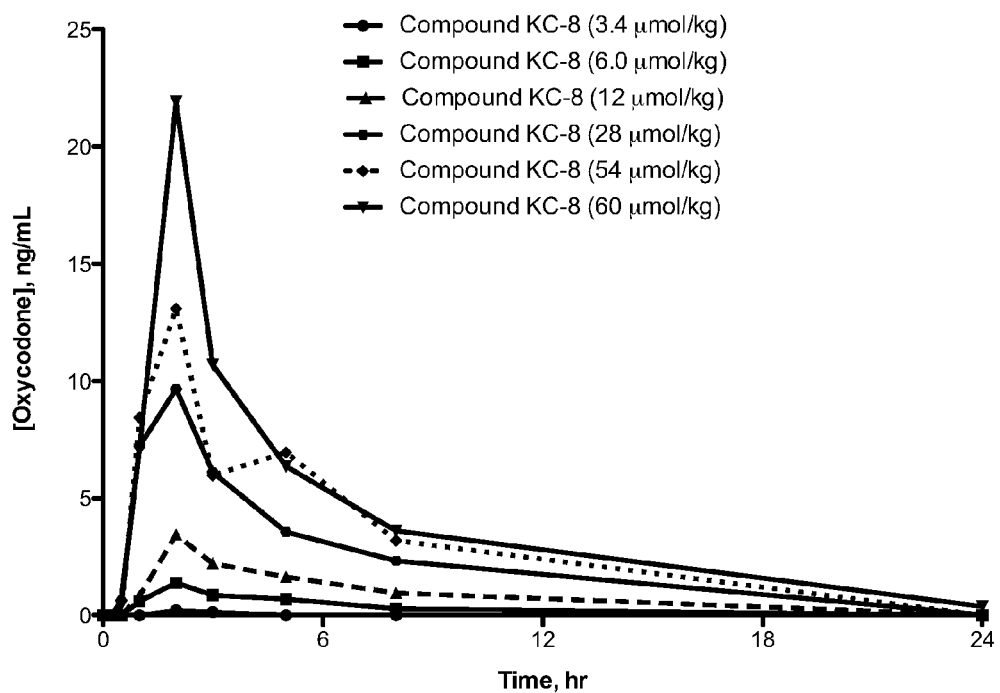
FIG. 4 compares mean plasma concentrations over time of oxycodone release following PO administration to rats of increasing doses of prodrug Compound KC-8.

Table 1 and FIG. 4 provide oxycodone exposure results for rats administered different doses of Compound KC-8. Results in Table 1 are reported, for each group of rats, as (a) maximum plasma concentration (Cmax) of oxycodone (OC) (average±standard deviation), (b) time after administration of Compound KC-8 to reach maximum oxycodone concentration (Tmax) (average±standard deviation) and (c) area under the curve (AUC) from 0 to 24 h (average±standard deviation).

TABLE 1

Cmax, Tmax and AUC values of oxycodone in rat plasma

| Dose, mg/kg | Dose μmol/kg | OC Cmax ± sd, ng/mL | Tmax ± sd, h | AUC ± sd, ng * h/mL |
|---|---|---|---|---|
| 2.8 | 3.4 | 0.281 ± 0.49* | 2.00 ± 0.0 | 0.373 ± 0.65 |
| 5 | 6.0 | 1.39 ± 0.84^ | 2.00 ± 0.0 | 5.34 ± 1.9 |
| 10 | 12 | 3.47 ± 1.6* | 2.25 ± 0.50 | 13.9 ± 3.2 |
| 23 | 28 | 10.4 ± 3.0^ | 1.75 ± 0.50 | 41.1 ± 18 |
| 45 | 54 | 14.7 ± 9.3* | 2.75 ± 1.5 | 52.9 ± 24 |
| 50 | 60 | 21.9 ± 5.3* | 2.00 ± 0.0 | 83.8 ± 24 |

*Lower limit of quantitation was 0.500 ng/mL
^Lower limit of quantitation was 0.100 ng/mL FIG. 4 compares mean plasma concentrations over time of oxycodone release following PO administration of increasing doses of Compound KC-8 to rats.

The results in Table 1 and FIG. 4 indicate that plasma concentrations of oxycodone increase proportionally with Compound KC-8 dose in rats.

Example 5

Pharmacokinetics of Compound KC-8 Following PO Administration to Dogs

This Example demonstrates the release of oxycodone into plasma when Compound KC-8 was administered orally (PO) to dogs. This Example also compares such release to that of Compound KC-3, an oxycodone prodrug that, unlike Compound KC-8, does not contain geminal dimethyl groups in its cyclizable spacer leaving group and lacks glycine in its trypsin-cleavable moiety. Also compared are oxycodone plasma levels in dogs administered oxycodone or OxyContin® tablets.

Study A.

Purebred male young adult/adult beagles were fasted overnight. Increasing doses of Compound KC-8 (as indicated in Table 2A), 4.15 mg/kg (5.7 μmol/kg) of Compound KC-3 (each of which can be prepared as described in the examples herein), or 2 mg/kg (5.7 μmol/kg) oxycodone HCl (Johnson Matthey Pharmaceutical Materials, West Deptford, N.J., USA) were administered in water via oral gavage (Table 2A indicates the number of dogs per group). In addition, one group of 4 dogs was administered one 20-mg OxyContin® Tablet (oxycodone HCl controlled-release) C-II per dog (NDC 59011-420-10, Purdue Pharma, Stamford, Conn., USA). The tablet dose was followed by approximately 5 mL of water to facilitate swallowing. The doses of oxycodone and of OxyContin® tablets were selected to provide approximately equimole amounts. Blood was collected from each animal via a jugular vein at various times over a 24-h period, centrifuged, and 0.8 mL plasma transferred to a fresh tube containing 8 μL formic acid; samples were vortexed, then immediately placed in dry ice, and stored in a −80° C. freezer until analysis by HPLC/MS.

Figure 5:
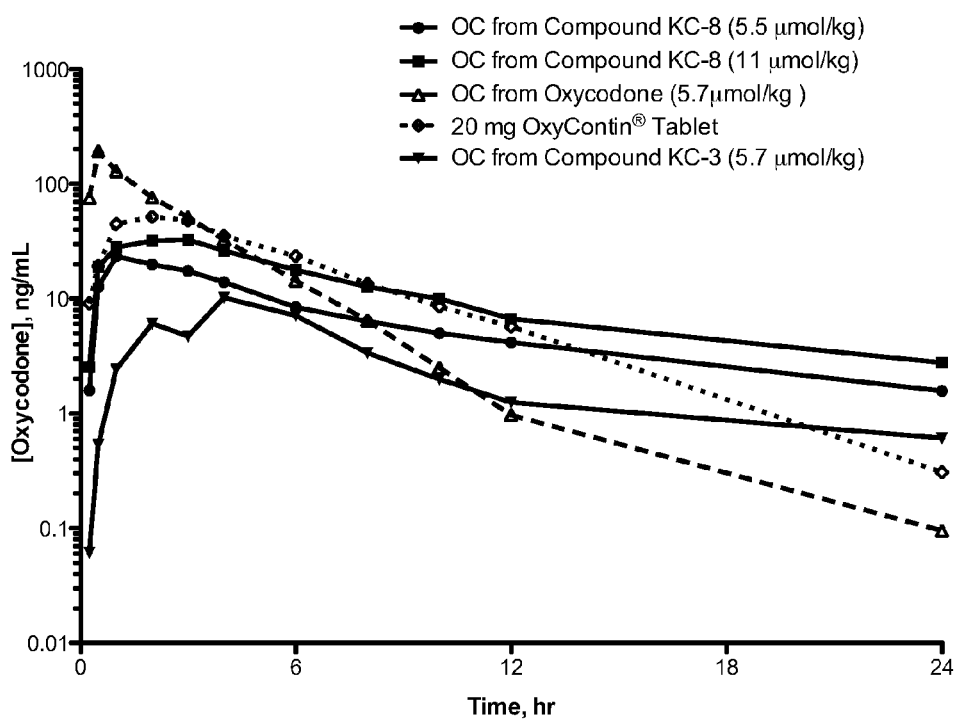
FIG. 5 compares mean plasma concentrations over time of oxycodone following PO administration to dogs of prodrug Compound KC-8, prodrug Compound KC-3, OxyContin® tablets, or oxycodone HCl.

Table 2A and FIG. 5 provide oxycodone exposure results for dogs administered the indicated compounds. Results in Table 2A are reported, for each group of dogs, as (a) maximum plasma concentration (Cmax) of oxycodone (OC) (average±standard deviation), (b) time after administration of compound to reach maximum oxycodone concentration (Tmax) (average±standard deviation) and (c) area under the curve (AUC) from 0 to 24 h (average±standard deviation).

TABLE 2A

Cmax, Tmax and AUC values of oxycodone in dog plasma

| Compound | Dose, mg/kg | Dose, μmol/kg | OC Cmax ± sd, ng/mL | Tmax ± sd, h | AUC ± sd (ng × h)/mL 0-24 h | Number of dogs |
|---|---|---|---|---|---|---|
| KC-8 | 4.55 | 5.5 | 23.5 ± 1.8 | 1.00 ± 0.0 | 159 ± 12 | 3 |
|  | 9.1 | 11 | 36.2 ± 4.4 | 2.33 ± 1.2 | 277 ± 20 | 3 |
| KC-3 | 4.15 | 5.7 | 10.2 ± 3.3 | 4.00 ± 0.00 | 65.6 ± 22 | 4 |
| Oxycodone | 2 | 5.7 | 193 ± 69 | 0.50 ± 0.00 | 418 ± 54 | 4 |
| OxyContin ® | 20 mg Tablet |  | 64.7 ± 8.8 | 2.75 ± 0.96 | 329 ± 160 | 4 |

Lower limit of quantitation was 0.0250 ng/mL

FIG. 5 compares mean plasma concentrations over time of oxycodone following PO administration of Compound KC-8, Compound KC-3, OxyContin® Tablets or oxycodone HCl to dogs.

The results in Table 2A and FIG. 5 indicate that oral administration of Compound KC-8 to dogs leads to a suppressed oxycodone Cmax, delayed oxycodone Tmax and extended oxycodone exposure time (AUC) compared to administration of oxycodone. Compound KC-8 also provides for significantly enhanced release of oxycodone into dog plasma (higher Cmax and AUC) than does Compound KC-3. The plasma PK profile of oxycodone release by Compound KC-8 administered orally to dogs resembles that of OxyContin® tablets more than that of oxycodone; duration of drug exposure is at least as long for Compound KC-8 as for OxyContin® tablets.

Study B.

Compound KC-8 was also dosed to dogs in a separate experiment at the doses indicated in Table 2B, and samples were collected at various times over a 48-h period. Otherwise, the procedures were the same as that described for Study A.

Table 2B provide oxycodone exposure results for dogs administered increasing doses of Compound KC-8. Results are reported as described for Table 2A, except AUC is calculated from 0 to 48 h.

TABLE 2B

Cmax, Tmax and AUC values of oxycodone in dog plasma

| Compound | Dose, mg/kg | Dose, μmol/kg | OC Cmax ± sd, ng/mL | Tmax ± sd, h | AUC ± sd (ng × h)/mL 0-48 h | Number of dogs |
|---|---|---|---|---|---|---|
| KC-8 | 4.55 | 5.48 | 17.2 ± 9.8** | 2.00 ± 1.4 | 123 ± 42 | 4 |
| KC-8 | 9.1# | 11.0 | 29.8 ± 9.1§ | 2.00 ± 0.0 | 264 ± 71 | 4 |
| KC-8 | 18.2 | 21.9 | 63.1 ± 5.4** | 3.50 ± 1.7 | 589 ± 56 | 4 |

§Lower limit of quantitation was 0.100 ng/mL
**Lower limit of quantitation was 0.0125 ng/mL
Dosed on a different day The results in Table 2B show that Compound KC-8 has a reproducible oral PK profile in dogs that is dose proportional.

Example 6

In Vitro Trypsin-Mediated Prodrug Cleavage and Spacer Leaving Group Cyclization Rate of Compound KC-8

This Example assesses the ability of trypsin to cleave oxycodone prodrug Compound KC-8. This Example also assesses the rate of cyclization and release of oxycodone by Compound KC-22, which is identical to Compound KC-8 except that Compound KC-22 lacks the trypsin-cleavable moiety.

Compound KC-8 was incubated with trypsin from bovine pancreas (Catalog No. T8003, Type I, ~10,000 BAEE units/mg protein, Sigma-Aldrich, St. Louis, Mo., USA). Specifically, the reactions included 0.761 mM of Compound KC-8•2HCl, 22.5 mM calcium chloride, 40 to 172 mM Tris pH 8 and 0.25% DMSO with variable activities of trypsin. The reactions were conducted at 37° C. for 24 h. Samples were collected at specified time points, transferred into 0.5% formic acid in acetonitrile to stop trypsin activity and stored at less than −70° C. until analysis by LC-MS/MS.

Cyclization release rates were measured by following the rate of disappearance of Compound KC-22 (2.18 mM initial concentration) in a 50 mM pH 7.4 phosphate buffer at 20° C.

Table 3 indicates the results of exposure of Compound KC-8 to trypsin. The results are expressed as half-life of prodrug when exposed to trypsin (i.e., Prodrug trypsin half-life) in hours and rate of oxycodone formation in μ moles per hour per BAEE unit (μmol/h/BAEE U) trypsin. Table 3 also indicates the cyclization rate of the cyclizable spacer leaving group of Compound KC-22. The results are expressed as half-life of compound disappearance.

TABLE 3

In vitro trypsin cleavage of Compound KC-8, and cyclization rate of Compound KC-22

| Prodrug | Prodrug trypsin half-life, h | OC formation rate, μmol/h/BAEE U | Compound | Disappearance half-life, h |
|---|---|---|---|---|
| KC-8 | 0.188 ± 0.0080 | 0.296 ± 0.044 | KC-22 | 10.4 ± 0.0060 |

* Adjusted to 4815 BAEE U/mL trypsin

The results in Table 3 indicate that Compound KC-8 can be cleaved by trypsin, and that the spacer leaving group of Compound KC-8 can cyclize, the latter result being shown directly by the cyclization rate of Compound KC-22.

Example 7

Oral Administration of Compound KC-8 Co-Dosed with Trypsin Inhibitor Compound 109 to Rats This Example demonstrates the ability of a trypsin inhibitor to affect the ability of Compound KC-8 to release oxycodone into plasma when Compound KC-8 is administered orally to rats.

Saline solutions of prodrug Compound KC-8 (which can be prepared as described in the examples herein) were dosed as indicated in Table 4. The rats were co-dosed with increasing concentrations of trypsin inhibitor Compound 109 (Catalog No. 3081, Tocris Bioscience, Ellisville, Mo., USA, or Catalog No. WS38665, Waterstone Technology, Cannel, 1N, USA) via oral gavage into jugular vein-cannulated male Sprague Dawley rats (4 per group) that had been fasted for 16-18 h prior to oral dosing. At specified time points, blood samples were drawn, harvested for plasma via centrifugation at 5,400 rpm at 4° C. for 5 min, and 100 microliters (μl) plasma transferred from each sample into a fresh tube containing 2 μl of 50% formic acid. The tubes were vortexed for 5-10 seconds, immediately placed in dry ice, and then stored in a −80° C. freezer until analysis by HPLC/MS.

TABLE 4

Co-dosing of prodrug Compound KC-8 and trypsin inhibitor Compound 109

| Compound KC-8 Dose, mg/kg | Compound KC-8 Dose, μmol/kg | Compound 109 Dose, mg/kg | Compound 109 Dose, μmol/kg |
|---|---|---|---|
| 5 | 6 | 0 | 0 |
| 5 | 6 | 0.1 | 0.2 |
| 5 | 6 | 0.5 | 0.9 |
| 5 | 6 | 1 | 1.9 |
| 50 | 60 | 0 | 0 |
| 50 | 60 | 1 | 1.9 |
| 50 | 60 | 5 | 9 |
| 50 | 60 | 10 | 19 |

Figure 6A:
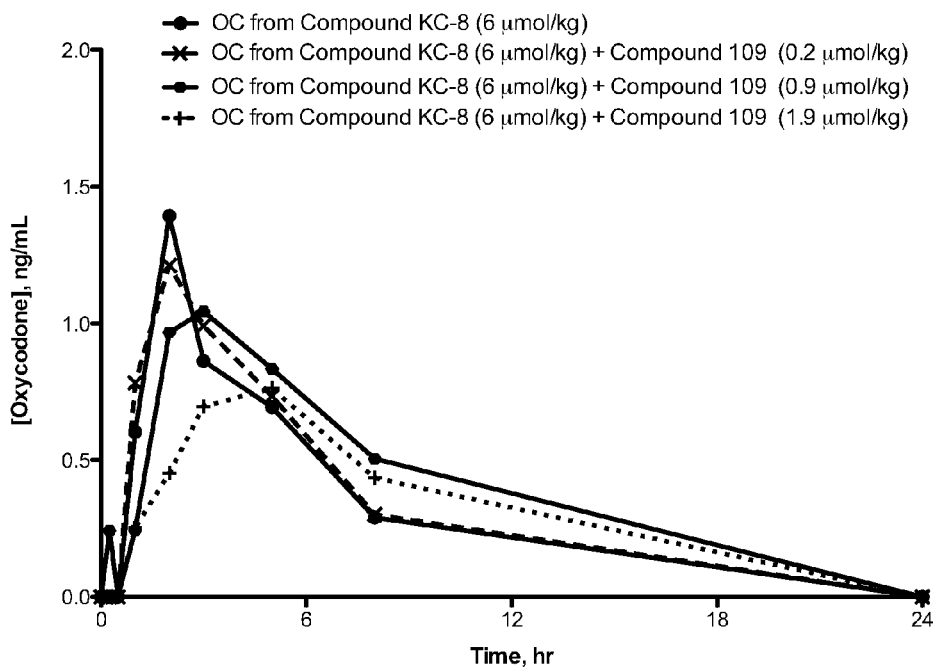
FIG. 6A and FIG. 6B compare mean plasma concentrations over time of oxycodone release following PO administration to rats of two doses of Compound KC-8, each co-dosed with increasing amounts of trypsin inhibitor Compound 109.
Figure 6B:
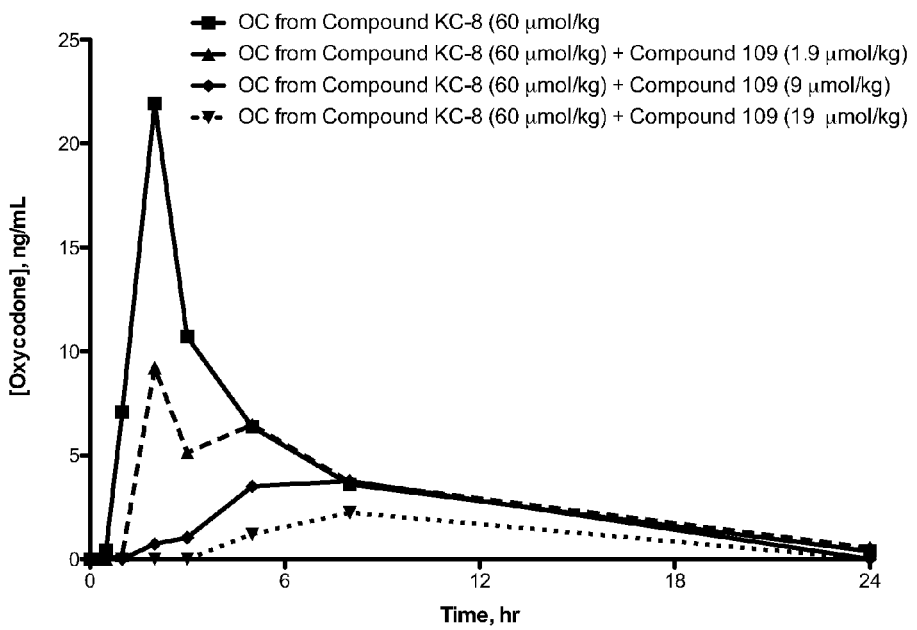

FIG. 6A and FIG. 6B provide oxycodone exposure results for rats administered with different doses of Compound KC-8 in the presence or absence of Compound 109.

FIG. 6A compares mean plasma concentrations over time of oxycodone release following PO administration of 5 mg/kg (6 μmol/kg) prodrug Compound KC-8 with increasing amounts of co-dosed trypsin inhibitor Compound 109 to rats.

FIG. 6B compares mean plasma concentrations over time of oxycodone release following PO administration of 50 mg/kg (60 μmol/kg) prodrug Compound KC-8 with increasing amounts of co-dosed trypsin inhibitor Compound 109 to rats.

The results in FIG. 6A and FIG. 6B indicate Compound 109's ability to attenuate Compound KC-8's ability to release oxycodone in rats in a dose dependent manner, as indicated by suppressed Cmax and/or delayed Tmax.

Example 8

Oral Administration of a Single Dose Unit and of Multiple Dose Units of a Composition Comprising Prodrug Compound KC-8 and Trypsin Inhibitor Compound 109 in Rats This Example demonstrates the effect of oral administration of single and multiple dose units comprising prodrug Compound KC-8 and trypsin inhibitor Compound 109 to rats.

Saline solutions of Compound KC-8 (which can be prepared as described in the examples herein) were dosed orally to rats (4 rats per group) at increasing concentrations ranging from 5 to 50 mg/kg (from 6 to 60 μmol/kg), wherein a single dose was represented as 5 mg/kg (6 μmol/kg) Compound KC-8 in the absence of trypsin inhibitor.

A second set of rats (4 rats per group) were co-dosed orally with prodrug Compound KC-8 and trypsin inhibitor Compound 109 (Catalog No. 3081, Tocris Bioscience, or Catalog No. WS38665, Waterstone Technology) as described below and indicated in Table 5. Specifically, a saline solution of a composition comprising 5 mg/kg (6 μmol/kg) Compound KC-8 and 0.5 mg/kg (1 μmol/kg) Compound 109, representative of a single dose unit, was administered via oral gavage to a group of 4 rats. It is to be noted that the mole-to-mole ratio of trypsin inhibitor-to-prodrug (109-to-KC-8) is 0.17-to-1; as such this dose unit is referred to herein as a 109-to-KC-8 (0.17-to-1) dose unit. Saline solutions representative of 2 dose units, 3 dose units, 4 dose units, 6 dose units, 8 dose units, and 10 dose units (i.e., as indicated in Table 5) of the 109-to-KC-8 (0.17- to 1) dose unit were similarly administered to additional groups of 4 rats.

All rats were jugular vein-cannulated male Sprague Dawley rats that had been fasted for 16-18 h prior to oral dosing. Dosing, sampling and analysis procedures were similar to those described in Example 4.

Figure 7A:
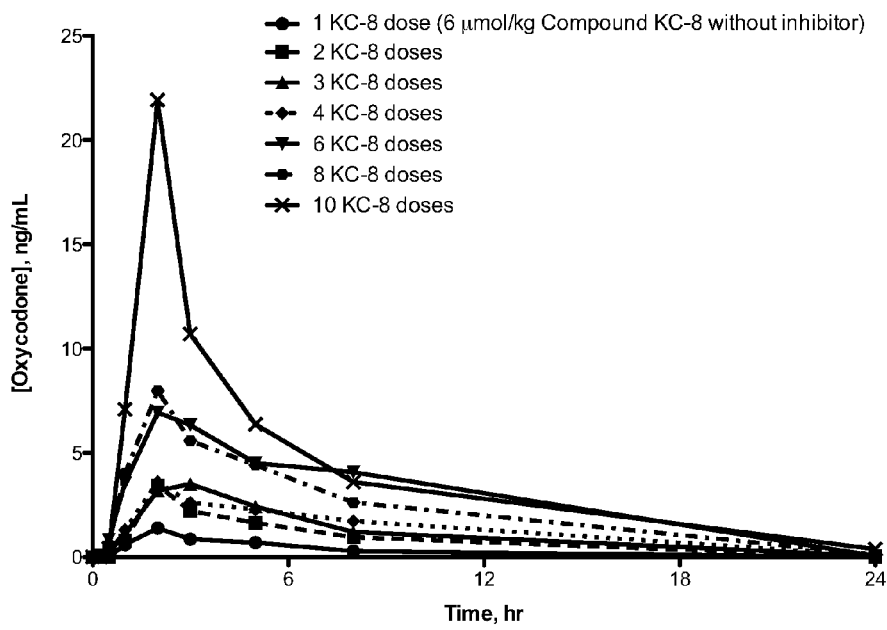
FIG. 7A compares mean plasma concentrations over time of oxycodone release following PO administration to rats of single and multiple doses of prodrug Compound KC-8 in the absence of trypsin inhibitor.
Figure 7B:
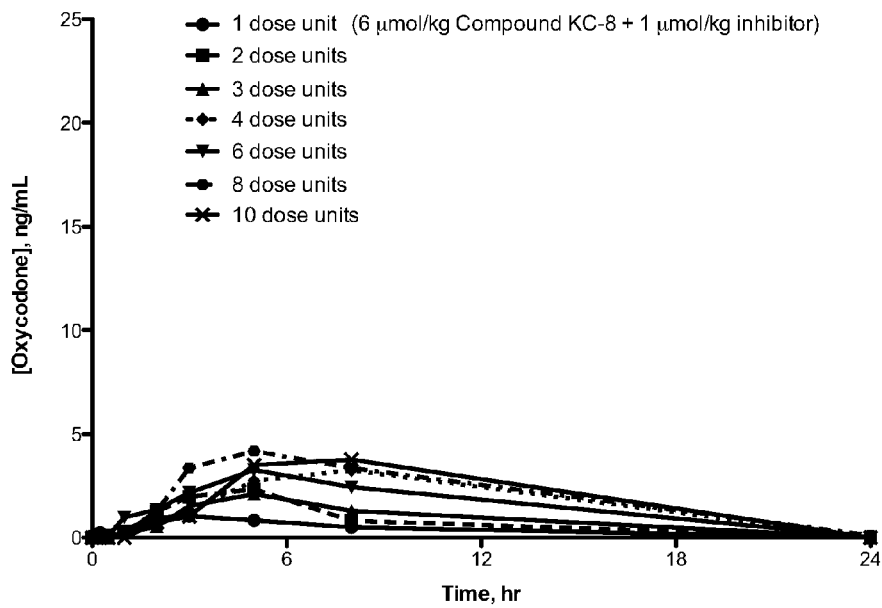
FIG. 7B compares mean plasma concentrations over time of oxycodone release following PO administration to rats of single and multiple dose units comprising prodrug Compound KC-8 and trypsin inhibitor Compound 109.

Table 5 (top half) and FIG. 7A provide oxycodone exposure results in plasma for rats administered 1, 2, 3, 4, 6, 8 and 10 doses of Compound KC-8 in the absence of trypsin inhibitor. Table 5 (bottom half) and FIG. 7B provide oxycodone exposure results in plasma for rats administered 1, 2, 3, 4, 6, 8 and 10 dose units of the 109-to-KC-8 (0.17-to-1) dose unit. Oxycodone Cmax, Tmax and AUC values are reported as described in Example 4.

TABLE 5

Cmax, Tmax and AUC values of oxycodone in rat plasma

| Amount (Multiple) | KC-8 Dose, mg/kg | KC-8 Dose, μmol/kg | 109 Dose, mg/kg | 109 Dose, μmol/kg | OC Cmax ± sd, ng/mL | Tmax ± sd, h | AUC ± sd, ng * h/mL |
|---|---|---|---|---|---|---|---|
| 1 KC-8 dose | 5 | 6 | 0 | 0* | 1.39 ± 0.84 | 2.00 ± 0.0 | 5.34 ± 1.9 |
| 2 KC-8 doses | 10 | 12 | 0 | 0# | 3.47 ± 1.6 | 2.25 ± 0.50 | 13.9 ± 3.2 |
| 3 KC-8 doses | 15 | 18 | 0 | 0^ | 4.23 ± 2.2 | 2.50 ± 0.58 | 24.3 ± 16 |
| 4 KC-8 doses | 20 | 24 | 0 | 0^ | 3.68 ± 1.7 | 2.25 ± 0.50 | 25.2 ± 14 |
| 6 KC-8 doses | 30 | 36 | 0 | 0^ | 7.42 ± 1.7 | 3.50 ± 3.0 | 65.1 ± 25 |
| 8 KC-8 doses | 40 | 48 | 0 | 0^ | 9.16 ± 5.3 | 2.25 ± 0.50 | 45.1 ± 26 |
| 10 KC-8 doses | 50 | 60 | 0 | 0# | 21.9 ± 5.3 | 2.00 ± 0.0 | 83.8 ± 24 |
| 1 dose unit | 5 | 6 | 0.5 | 1* | 1.09 ± 0.55 | 3.25 ± 1.3 | 5.66 ± 2.0 |
| 2 dose units | 10 | 12 | 1 | 2^ | 2.82 ± 0.97 | 3.50± 1.0 | 11.6 ± 1.5 |
| 3 dose units | 15 | 18 | 1.5 | 3^ | 2.13 ± 0.75 | 4.50 ± 1.0 | 10.3 ± 4.3 |
| 4 dose units | 20 | 24 | 2 | 4^ | 3.34 ± 2.1 | 7.25 ± 1.5 | 14.6 ± 9.1 |
| 6 dose units | 30 | 36 | 3 | 6^ | 3.27 ± 1.2 | 5.00 ± 0.0 | 28.6 ± 19 |
| 8 dose units | 40 | 48 | 4 | 7^ | 4.63 ± 3.3 | 4.50 ± 1.0 | 45.2 ± 39 |
| 10 dose units | 50 | 60 | 5 | 9# | 4.24 ± 0.71 | 6.50 ± 1.7 | 20.0 ± 3.5 |

*Lower limit of quantitation was 0.100 ng/mL
^Lower limit of quantitation was 0.0500 ng/mL
Lower limit of quantitation was 0.500 ng/mL FIG. 7A compares mean plasma concentrations over time of oxycodone release following PO administration of a single dose and of multiple doses of Compound KC-8 dosed in the absence of trypsin inhibitor.

FIG. 7B compares mean plasma concentrations over time of oxycodone release following PO administration of a single dose unit and of multiple dose units of a composition comprising prodrug Compound KC-8 and trypsin inhibitor Compound 109.

The results in Table 5, FIG. 7A and FIG. 7B indicate that administration of multiple dose units (as exemplified by 1, 2, 3, 4, 6, 8 and 10 dose units of the 109-to-KC-8 (0.17- to 1) dose unit) results in a plasma oxycodone concentration-time PK profile that is not dose proportional to the plasma oxycodone concentration-time PK profile of the single dose unit. In addition, the PK profile of the multiple dose units (e.g., FIG. 7B) was modified compared to the PK profile of the equivalent dosage of prodrug in the absence of trypsin inhibitor (e.g., FIG. 7A).

Example 9

Oral Administration of Compound KC-8 Co-Dosed with Trypsin Inhibitor Compound 109 to Dogs This Example demonstrates the ability of a trypsin inhibitor to affect the ability of Compound KC-8 to release oxycodone into plasma when Compound KC-8 is administered orally (PO) to dogs.

Purebred male young adult/adult beagles were fasted overnight. Compound KC-8 (which can be prepared as described in the examples herein) was administered at 18.2 mg/kg (22 µmol/kg) with or without a co-dose of 1.8 mg/kg (3.3 µmol/kg) Compound 109 (Catalog No. 3081, Tocris Bioscience, or Catalog No. WS38665, Waterstone Technology) in water via oral gavage as indicated in Table 6. Blood was collected, treated and analyzed as in Example 5.

Figure 8:
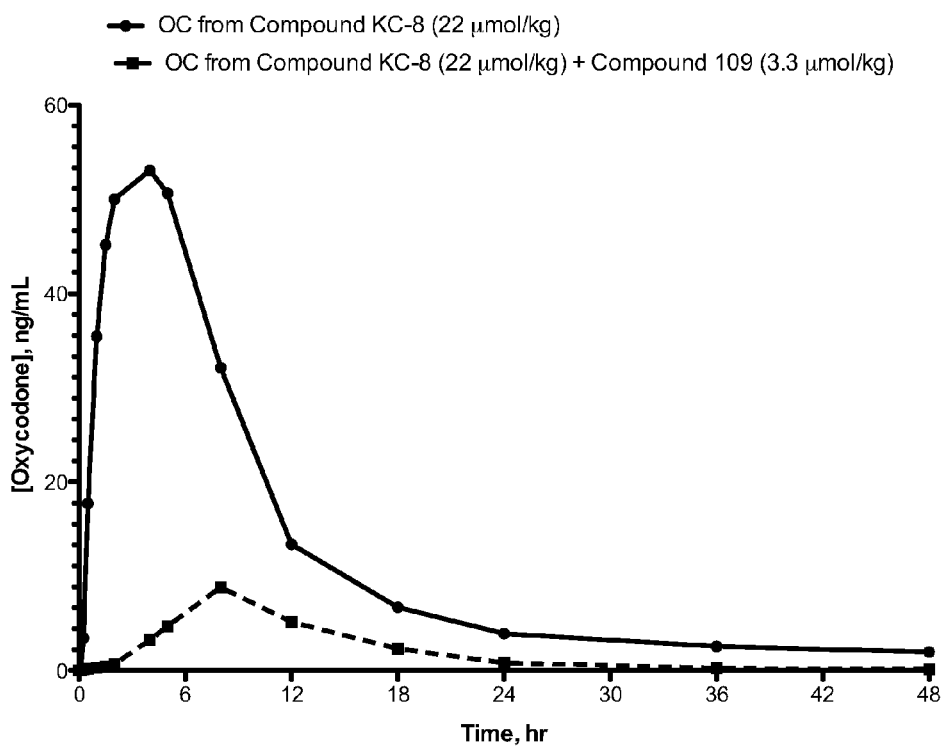
FIG. 8 compares mean plasma concentrations over time of oxycodone release following PO administration to dogs of prodrug Compound KC-8 in the absence or presence of trypsin inhibitor Compound 109.

Table 6 and FIG. 8 provide oxycodone exposure results for dogs administered Compound KC-8, in the presence or absence of Compound 109. Results in Table 6 are reported for each group of four dogs, as described in Example 5.

TABLE 6

| | | | Dog dosing PO with Compound KC-8 in the absence or presence of Compound 109 | | | |
|---|---|---|---|---|---|---|
| KC-8 Dose, mg/kg | KC-8 Dose, µmol/kg | Compound 109 Dose, mg/kg | Compound 109 Dose, µmol/kg | OC Cmax ± sd, ng/mL | Tmax ± sd, h | AUC ± sd, ng * h/mL |
| 18.2 | 22 | 0 | 0 | 63.1 ± 5.4 | 3.50 ± 1.7 | 589 ± 56 |
| 18.2 | 22 | 1.8 | 3.3 | 8.86 ± 1.8 | 8.00 ± 0.0 | 98.4 ± 25 |

Lower limit of quantitation was 0.0125 ng/mL

FIG. 8 compares mean plasma concentrations over time of oxycodone release following PO administration to dogs of Compound KC-8 with or without a co-dose of trypsin inhibitor Compound 109.

The results in Table 6 and FIG. 8 indicate Compound 109's ability to attenuate Compound KC-8's ability to release oxycodone, both by suppressing Cmax and AUC and by delaying Tmax.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising a trypsin inhibitor and N-1-[3-(oxycodone-6-enol-carbonyl-methyl-amino)-2,2-dimethyl-propylamine]-arginine-glycine-malonic acid, Compound KC-8, shown below:

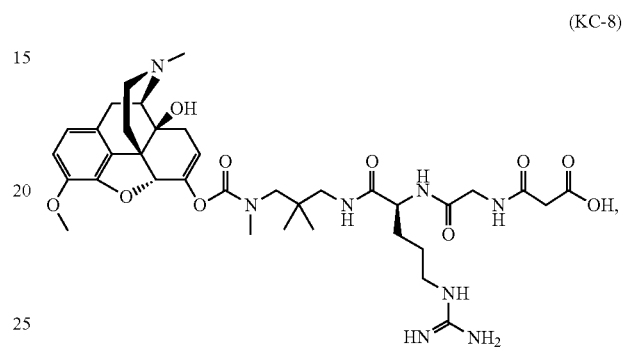

(KC-8)

or acceptable salts thereof.

2. The composition of claim 1, wherein the trypsin inhibitor is an arginine mimic or a lysine mimic.

3. The composition of claim 2, wherein the arginine mimic or lysine mimic is a synthetic compound.

4. The composition of claim 1, wherein the trypsin inhibitor is a compound of formula:

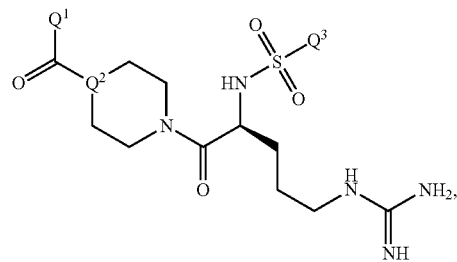

wherein:
$Q^1$ is selected from —O-$Q^4$ or -$Q^4$-COOH, where $Q^4$ is $C_1$-$C_4$ alkyl;
$Q^2$ is N or CH; and
$Q^3$ is aryl or substituted aryl.

5. The composition of claim 1, wherein the trypsin inhibitor is a compound of formula:

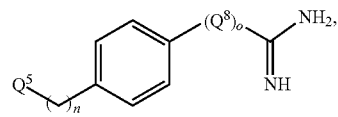

wherein:
$Q^5$ is —C(O)—COOH or —NH-$Q^6$-$Q^7$-$SO_2$—$C_6H_5$, where
$Q^6$ is —$(CH_2)_p$—COOH;
$Q^7$ is —$(CH_2)_r$—$C_6H_5$;

Q⁸ is NH;
n is a number from zero to two;
o is zero or one;
p is an integer from one to three; and
r is an integer from one to three.

6. The composition of claim 1, wherein the trypsin inhibitor is a compound of formula:

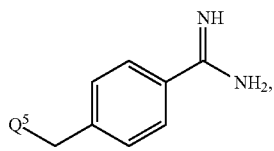

wherein:
Q⁵ is —C(O)—COOH or —NH-Q⁶-Q⁷-SO₂—C₆H₅, where
Q⁶ is —(CH₂)$_p$—COOH;
Q⁷ is —(CH₂)$_r$—C₆H₅; and
p is an integer from one to three; and
r is an integer from one to three.

7. The composition of claim 1, wherein the trypsin inhibitor is a compound of formula:

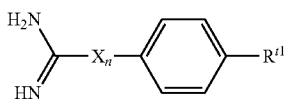
(T-II)

wherein
X is NH;
n is zero or one; and
R$^{t1}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH₂)$_m$—C(O)—O—(CH₂)$_m$—C(O)—N—R$^{n1}$R$^{n2}$, wherein each m is independently zero to 2; and R$^{n1}$ and R$^{n2}$ are independently selected from hydrogen and C$_{1-4}$ alkyl.

8. The composition of claim 1, wherein the trypsin inhibitor is a compound of formula:

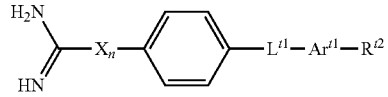
(T-III)

wherein
X is NH;
n is zero or one;
L$^{t1}$ is selected from —C(O)—O—; —O—C(O)—; —O—(CH₂)$_m$—O—; —OCH₂—Ar$^{t2}$-CH₂O—; —C(O)—NR$^{t3}$—; and —NR$^{t3}$—C(O)—;
R$^{t3}$ is selected from hydrogen, C$_{1-6}$ alkyl, and substituted C$_{1-6}$ alkyl;

Ar$^{t1}$ and Ar$^{t2}$ are independently a substituted or unsubstituted aryl group;
m is a number from 1 to 3; and
R$^{t2}$ is selected from hydrogen, halogen, nitro, alkyl, substituted alkyl, alkoxy, carboxyl, alkoxycarbonyl, acyl, aminoacyl, guanidine, amidino, carbamide, amino, substituted amino, hydroxyl, cyano and —(CH₂)$_m$—C(O)—O—(CH₂)$_m$—C(O)—N—R$^{n1}$R$^{n2}$, wherein each m is independently zero to 2; and R$^{n1}$ and R$^{n2}$ are independently selected from hydrogen and C$_{1-4}$ alkyl.

9. The composition of claim 1, wherein the trypsin inhibitor is a compound of formula:

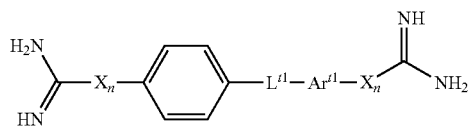
(T-IV)

wherein
each X is NH;
each n is independently zero or one;
L$^{t1}$ is selected from —C(O)—O—; —O—C(O)—; —O—(CH₂)$_m$—O—; —OCH₂—Ar$^{t2}$-CH₂O—; —C(O)—NR$^{t3}$—; and —NR$^{t3}$—C(O)—;
R$^{t3}$ is selected from hydrogen, C$_{1-6}$ alkyl, and substituted C$_{1-6}$ alkyl;
Ar$^{t1}$ and Ar$^{t2}$ are independently a substituted or unsubstituted aryl group; and
m is a number from 1 to 3.

10. The composition of claim 1, wherein the trypsin inhibitor is selected from
(S)-ethyl 4-(5-guanidino-2-(naphthalene-2-sulfonamido)pentanoyl)piperazine-1-carboxylate;
(S)-ethyl 4-(5-guanidino-2-(2,4,6-triisopropylphenylsulfonamido)pentanoyl)piperazine-1-carboxylate;
(S)-ethyl 1-(5-guanidino-2-(naphthalene-2-sulfonamido)pentanoyl)piperidine-4-carboxylate;
(S)-ethyl 1-(5-guanidino-2-(2,4,6-triisopropylphenylsulfonamido)pentanoyl)piperidine-4-carboxylate;
(S)-6-(4-(5-guanidino-2-(naphthalene-2-sulfonamido)pentanoyl)piperazin-1-yl)-6-oxohexanoic acid;
4-aminobenzimidamide;
3-(4-carbamimidoylphenyl)-2-oxopropanoic acid;
(S)-5-(4-carbamimidoylbenzylamino)-5-oxo-4-((R)-4-phenyl-2-(phenylmethylsulfonamido)butanamido)pentanoic acid;
6-carbamimidoylnaphthalen-2-yl-4-(diaminomethyleneamino)benzoate; and
4,4'-(pentane-1,5-diylbis(oxy))dibenzimidamide.

11. The composition of claim 1, wherein the trypsin inhibitor is 6-carbamimidoylnaphthalen-2-yl-4-(diaminomethyleneamino)benzoate (Compound 109).

12. A method of treating or preventing pain in a patient in need thereof, which comprises administering an effective amount of a composition of claim 1 to the patient.

* * * * *